US010513691B2

(12) United States Patent
Matheu et al.

(10) Patent No.: US 10,513,691 B2
(45) Date of Patent: *Dec. 24, 2019

(54) METHODS FOR PRINTING ORGANS AND ORGANOIDS

(71) Applicant: Prellis Biologics, Inc., Hayward, CA (US)

(72) Inventors: Melanie P. Matheu, San Francisco, CA (US); Kathryn J. Parkinson, Palo Alto, CA (US); Emma R. Moulton, Hayward, CA (US)

(73) Assignee: PRELLIS BIOLOGICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,413

(22) Filed: Jul. 24, 2018

(65) Prior Publication Data

US 2019/0010463 A1    Jan. 10, 2019

Related U.S. Application Data

(63) Continuation of application No. PCT/US2018/034489, filed on May 24, 2018.

(60) Provisional application No. 62/556,242, filed on Sep. 8, 2017, provisional application No. 62/511,275, filed on May 25, 2017, provisional application No. 62/511,205, filed on May 25, 2017.

(51) Int. Cl.
| | | |
|---|---|---|
| *C12N 5/07* | (2010.01) | |
| *C12N 5/078* | (2010.01) | |
| *C12N 5/071* | (2010.01) | |
| *C12M 3/04* | (2006.01) | |
| *C12N 5/077* | (2010.01) | |
| *C12N 5/0775* | (2010.01) | |
| *C12N 5/0781* | (2010.01) | |
| *C12N 5/00* | (2006.01) | |
| *C12N 5/0783* | (2010.01) | |
| *C12N 5/0784* | (2010.01) | |
| *C07K 16/00* | (2006.01) | |
| *C07K 16/10* | (2006.01) | |

(52) U.S. Cl.
CPC ............ *C12N 5/0671* (2013.01); *C07K 16/00* (2013.01); *C07K 16/1081* (2013.01); *C12M 3/04* (2013.01); *C12N 5/0018* (2013.01); *C12N 5/0062* (2013.01); *C12N 5/064* (2013.01); *C12N 5/0635* (2013.01); *C12N 5/0637* (2013.01); *C12N 5/0638* (2013.01); *C12N 5/0667* (2013.01); *C12N 5/0669* (2013.01); *C12N 5/0691* (2013.01); *C12N 5/0697* (2013.01); *C12N 5/0698* (2013.01); *C07K 2317/21* (2013.01); *C07K 2317/76* (2013.01); *C12N 2502/09* (2013.01); *C12N 2502/094* (2013.01); *C12N 2502/1114* (2013.01); *C12N 2502/1121* (2013.01); *C12N 2502/1323* (2013.01); *C12N 2502/45* (2013.01); *C12N 2506/1384* (2013.01); *C12N 2506/28* (2013.01); *C12N 2510/02* (2013.01); *C12N 2513/00* (2013.01); *C12N 2527/00* (2013.01); *C12N 2533/30* (2013.01); *C12N 2533/54* (2013.01); *C12N 2533/74* (2013.01); *C12N 2533/76* (2013.01); *C12N 2533/80* (2013.01); *C12N 2539/10* (2013.01)

(58) Field of Classification Search
None
See application file for complete search history.

(56) References Cited

U.S. PATENT DOCUMENTS

| | | | |
|---|---|---|---|
| 4,669,812 | A | 6/1987 | Hoebing |
| 5,024,508 | A | 6/1991 | Horner et al. |
| 5,194,971 | A | 3/1993 | Haines et al. |
| 5,561,537 | A | 10/1996 | Aritake et al. |
| 6,139,574 | A | 10/2000 | Vacanti et al. |
| 6,259,450 | B1 | 7/2001 | Chiabrera et al. |
| 6,304,263 | B1 | 10/2001 | Chiabrera et al. |
| 6,608,228 | B1 | 8/2003 | Cumpston et al. |
| 6,819,469 | B1 | 11/2004 | Koba |
| 7,535,607 | B2 | 5/2009 | Schwerdtner et al. |
| 8,339,695 | B2 | 12/2012 | Haussler et al. |
| 9,114,032 | B1 | 8/2015 | Pulugurtha |
| 9,631,171 | B2 | 4/2017 | Soman et al. |
| 2004/0067433 | A1 | 4/2004 | Nirmal et al. |
| 2004/0089804 | A1 | 5/2004 | Dantus et al. |
| 2004/0126694 | A1 | 7/2004 | Devoe et al. |
| 2004/0196524 | A1 | 10/2004 | Hughes et al. |
| 2004/0263930 | A1 | 12/2004 | Payne et al. |
| 2005/0208431 | A1 | 9/2005 | Devoe et al. |
| 2005/0226856 | A1 | 10/2005 | Ahlfors |
| 2005/0286101 | A1 | 12/2005 | Garner et al. |
| 2006/0050340 | A1 | 3/2006 | Schwerdtner et al. |
| 2008/0194721 | A1 | 8/2008 | Arney et al. |
| 2008/0286482 | A1 | 11/2008 | Cheung et al. |
| 2009/0323508 | A1 | 12/2009 | Tomura et al. |
| 2010/0296148 | A1 | 11/2010 | Reichelt et al. |

(Continued)

FOREIGN PATENT DOCUMENTS

| | | |
|---|---|---|
| EP | 3096171 A1 | 11/2016 |
| WO | WO-2016083784 A1 | 6/2016 |

(Continued)

OTHER PUBLICATIONS

Suematsu et al., "Generation of a synthetic lymphoid tissue-like organoid in mice", Nature Biotechnology, vol. 22, pp. 1539-1545. (Year: 2004).*

(Continued)

*Primary Examiner* — Michelle F. Paguio Frising
(74) *Attorney, Agent, or Firm* — Wilson Sonsini Goodrich & Rosati

(57) ABSTRACT

Provided herein are methods and systems for bio-printing of three-dimensional organs and organoids. Also provided herein are bio-printed three-dimensional organs and organoids for use in the generation and/or the assessment of immunological products and/or immune responses. Also provided herein are methods and system for bio-printing three-dimensional matrices.

29 Claims, 37 Drawing Sheets

(56) References Cited

U.S. PATENT DOCUMENTS

| | | |
|---|---|---|
| 2011/0033887 A1 | 2/2011 | Fang et al. |
| 2011/0128555 A1 | 6/2011 | Rotschild et al. |
| 2011/0149359 A1 | 6/2011 | Leister |
| 2011/0171689 A1 | 7/2011 | Warren et al. |
| 2011/0318528 A1 | 12/2011 | Cho et al. |
| 2013/0012612 A1 | 1/2013 | Houbertz-Krauss et al. |
| 2013/0203146 A1 | 8/2013 | Ying et al. |
| 2013/0234372 A1 | 9/2013 | Almutairi et al. |
| 2013/0304233 A1 | 11/2013 | Dean et al. |
| 2014/0017651 A1 | 1/2014 | Sugimoto et al. |
| 2014/0028663 A1 | 1/2014 | Smithwick et al. |
| 2014/0113373 A1 | 4/2014 | Chien et al. |
| 2014/0126029 A1 | 5/2014 | Fuetterer |
| 2015/0097315 A1 | 4/2015 | Desimone et al. |
| 2015/0165020 A1 | 6/2015 | Jaklenec et al. |
| 2015/0375453 A1 | 12/2015 | Yost et al. |
| 2016/0033874 A1 | 2/2016 | Tang et al. |
| 2016/0107380 A1 | 4/2016 | Smoot et al. |
| 2016/0298087 A1 | 10/2016 | Qu et al. |
| 2016/0303797 A1 | 10/2016 | Moran |
| 2016/0322560 A1 | 11/2016 | Sirbuly et al. |
| 2017/0087766 A1 | 3/2017 | Chung et al. |
| 2017/0120337 A1 | 5/2017 | Kanko et al. |
| 2017/0136692 A1 | 5/2017 | Zheng et al. |
| 2017/0281828 A1 | 10/2017 | Zhang et al. |
| 2017/0283766 A1 | 10/2017 | Hribar et al. |
| 2017/0348907 A1 | 12/2017 | Melde et al. |
| 2017/0371248 A1 | 12/2017 | Tang et al. |
| 2018/0117219 A1 | 5/2018 | Yang et al. |
| 2018/0126630 A1 | 5/2018 | Panzer et al. |
| 2018/0147776 A1 | 5/2018 | Kotani et al. |
| 2018/0370144 A1 | 12/2018 | Revanur et al. |
| 2018/0371389 A1 | 12/2018 | Delrot et al. |
| 2019/0016052 A1 | 1/2019 | Clark |
| 2019/0031911 A1 | 1/2019 | Rolland et al. |

FOREIGN PATENT DOCUMENTS

| | | |
|---|---|---|
| WO | WO-2018165613 A1 | 9/2018 |
| WO | WO-2018218085 A2 | 11/2018 |

OTHER PUBLICATIONS

Allen et al. Imaging of Germinal Center Selection Events During Affinity Maturation. Science 315:528-531 (2007).
Bajaj et al. 3D Biofabrication Strategies for Tissue Engineering and Regenerative Medicine. Annu rev Biomed Eng 16:247-276 (2014).
Billiet et al. A review of trends and limitations in hydrogel-rapid prototyping for tissue engineering. Biomaterials 33:6020-6041 (2012).
Collins. Bioprinting Is Changing Regenerative Medicine Forever. Stem Cells Dev 23 Suppl 1:79-82 (2014).
Co-pending U.S. Appl. No. 15/925,582, filed Mar. 19, 2018.
Cuchiara et al. Integration of Self-Assembled Microvascular Networks with Microfabricated PEG-Based Hydrogels. Adv Funct Mater 22(21):4511-4518 (2012 ).
Culver et al. Three-dimensional biomimetic patterning in hydrogels to guide cellular organization. Adv Mater 24(17):2344-2348 (2012).
Farsari et al. Two-photon polymerization of an Eosin Y-sensitized acrylate composite. Journal of Photochemistry and Photobiology A: Chemistry 181(1):132-135 (2006).
Hernandez et al. Three-dimensional spatiotemporal focusing of holographic patterns. Nat Commun 7:11928 (2016).
Huh et al. Reconstituting Organ-Level Lung Functions on a Chip. Science 328(5986):1662-1668 (2010).
Itoh et al. Scaffold-Free Tubular Tissues Created by a Bio-3D Printer Undergo Remodeling and Endothelialization when Implanted in Rat Aortae. PLoS One 10(9):e0136681 (2015).
Jang et al. Human kidney proximal tubule-on-a-chip for drug transport and nephrotoxicity assessment. Integrative Biology 5(9):1089-1198 (2013).
King et al. 3D Proximal Tubule Tissues Recapitulate Key Aspects of Renal Physiology to Enable Nephrotoxicity Testing. Front Physiol 8:123 (2017).
Linnenberger. Live cell lithography and non-invasive mapping of neural networks. Univ of Colorado. Thesis (127 pgs) (2014).
Murphy et al. 3D bioprinting of tissues and organs. Nat Biotech 32:773-785 (2014).
Pereira et al. 3D Photo-Fabrication for Tissue Engineering and Drug Delivery. Engineering 1(1):90-112 (2015).
Sistare et al. The Promise of New Technologies to Reduce, Refine, or Replace Animal Use while Reducing Risks of Drug Induced Liver Injury in Pharmaceutical Development. ILAR J 57(2):186-211 (2016).
Stankevicius et al. Holographic lithography for biomedical applications. Proc. Of SPIE 8433:843312-1 to 843312-7 (May 11, 2012).
Tas et al. Visualizing antibody affinity maturation in germinal centers. Science 10.1126/science.aad3439 (2016).
U.S. Appl. No. 15/925,582 Office Action dated Jun. 29, 2018.
Yanagawa et al. Hydrogel microfabrication technology toward three dimensional tissue engineering. Regenerative Therapy 3:45-57 (2016).
Yuan et al. Laser Scanning Holographic Lithography for Flexible 3D Fabrication of Multi-Scale Integrated Nano-structures and Optical Biosensors. Sci Rep 6:22294 (2016).
Zhang et al. Optimized holographic femtosecond laser patterning method towards rapid integration of high-quality functional devices in microchannels. Sci Rep 6:33281 (2016).
Zheren et al. 3D Micro-concrete Hybrid Structures Fabricated by Femtosecond Laser Two-Photon Polymerization for Biomedical and Photonic Applications. 2016 IEEE International Conference on Industrial Technology (ICIT), Taipei, Taiwan (pp. 1108-1114) (2016).
Zhu et al. Direct 3D bioprinting of prevascularized tissue constructs with complex microarchitecture. Biomaterials 124:106-115 (2017).
PCT/US2018034489 International Search Report and Written Opinion dated Jan. 17, 2019.
U.S. Appl. No. 15/925,582 Office Action dated Jan. 11, 2019.
Koo et al. Laser-assisted biofabrication in tissue engineering and regenerative medicine. J Mat Res 32(1):128-142 (2017).
Ovsianikov et al. Laser photofabrication of cell-containing hydrogel constructs. Langmuir 30:3787-3794 (2013).
PCT/US2018/021850 International Search Report and Written Opinion dated Jul. 24, 2018.
Shusteff et al. Additive fabrication of 3D structures by holographic lithography/ In: Solid Freeform Fabrication 2016: Proceedings of the 27th Annual International Solid Freeform Fabrication Symposium—An additive Manufacturing Conference, Edited by Bourell, David L. et al., University of Texas, 2016, pp. 1183-1192.
Suematsu et al. Generation of a synthetic lymphoid tissue-like organoid in mice. Nat Biotech 22(12):1539-1545 (2004).
U.S. Appl. No. 15/925,582 Office Action dated Sep. 5, 2019.

\* cited by examiner

SINGLE FIBER CABLE

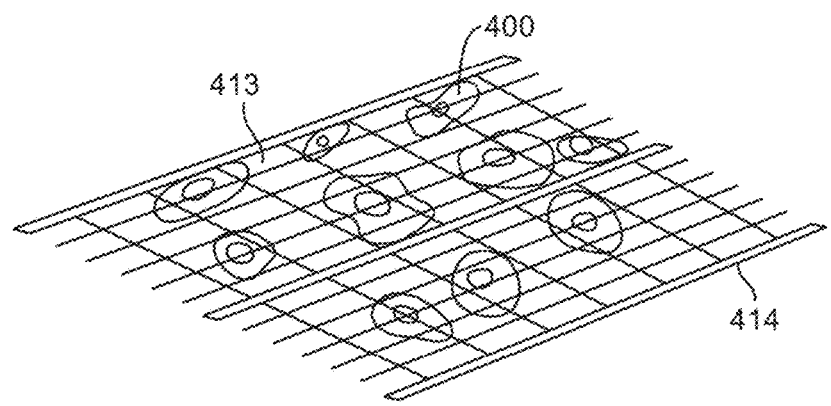
FIG. 27
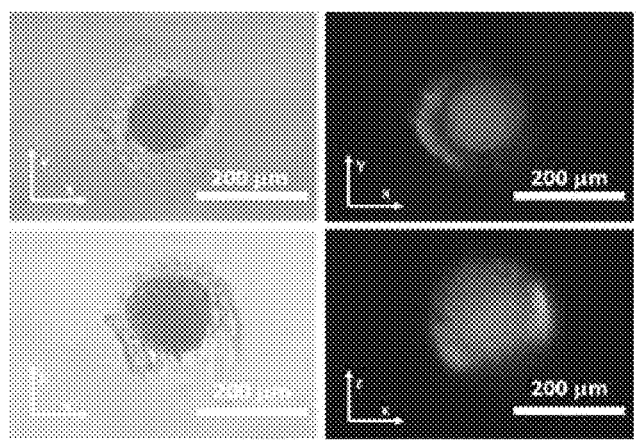
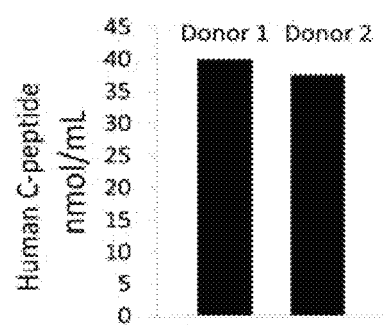
FIG. 28A
FIG. 28B

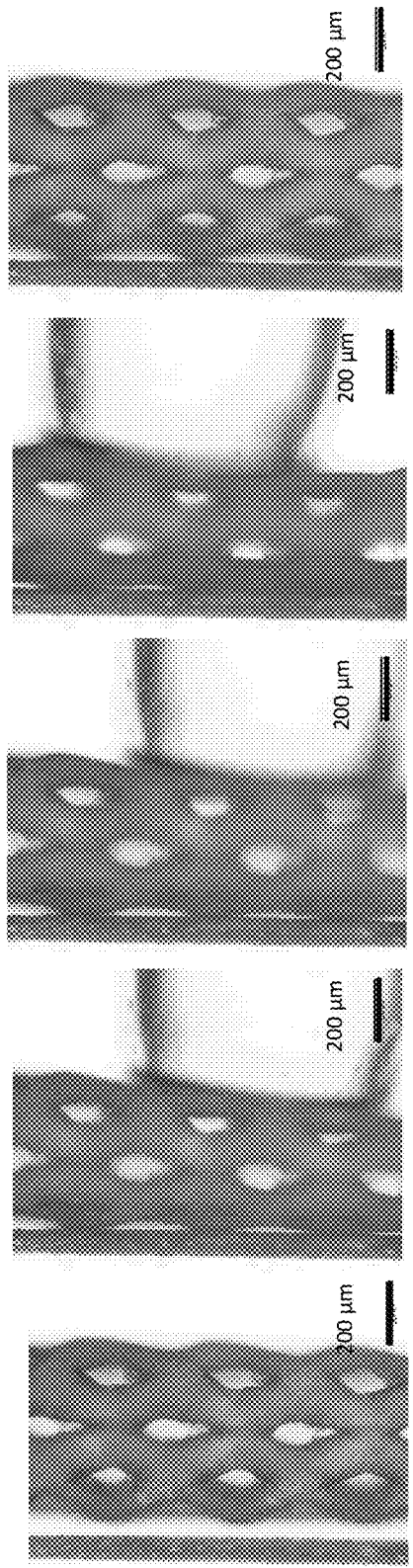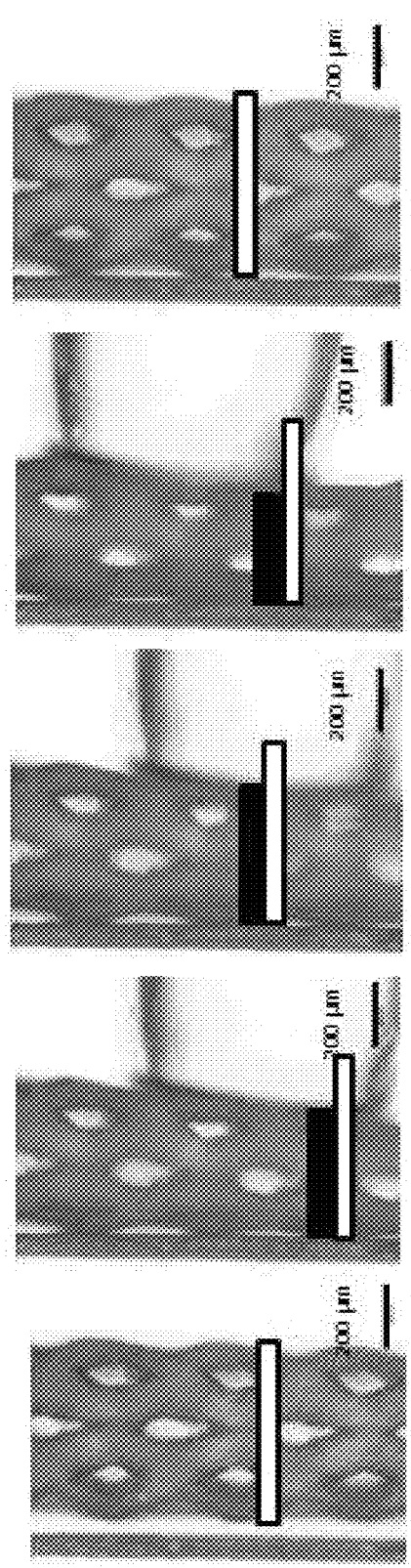
FIG. 30A
FIG. 30B

METHODS FOR PRINTING ORGANS AND ORGANOIDS

CROSS-REFERENCE

This application is a continuation of International Application No. PCT/US2018/034489, filed on May 24, 2017, which claims the benefit of U.S. Provisional Patent Application No. 62/511,205, filed May 25, 2017, U.S. Provisional Patent Application No. 62/511,275, filed May 25, 2017, U.S. Provisional Patent Application No. 62/556,242, filed Sep. 8, 2017, each of which are entirely incorporated herein by reference.

BACKGROUND

Despite significant advances in the fields of cell biology, microfluidics, engineering, and three-dimensional printing, to date, conventional approaches have failed to re-create functional capillaries that feed and support the thick tissue necessary to construct a human organ. To date, these approaches in tissue engineering have relied on the ingrowth of blood vessels into tissue-engineered devices to achieve permanent vascularization. This strategy has worked for some tissues that are either very thin such as a bladder wall replacement or tissues such as bone replacements that do not require vasculature to function. However, current tissue engineering techniques fall short in the creation of complex tissues such as large vital organs, including liver, kidney, thick skin, and heart. Larger tissues may also be thought of as an organization of smaller tissue sub-units; for example, the kidney is comprised of hundreds of thousands of nephron units, the functional unit of the lungs, i.e., the alveolar spaces, have a combined surface area of 70 to 80 meters squared ($m^2$), but are only 1 cell wall, 5 to 10 micrometers ($\mu m$), thick. Current tissue printing methodology not only fails to re-create the fine microvasculature necessary to support tissues thicker than 300 micrometers ($\mu m$), but cannot organize cells into the structural orientations and niches that are necessary for organ function.

Antibodies are proteins produced and secreted by B cells during an immune response. Antibodies may have high binding specificity and affinity to potential infectious agents and thus may be used to bind to and isolate, neutralize, or alter the effects of other proteins, viruses, bacteria, chemical-protein combinations, or carbohydrate molecules. This makes antibodies a valuable protein in protection from pathogens and isolation or neutralization of infectious or otherwise pathologic agents or proteins. In addition, antibodies may be used to redirect immune responses, by modulation through either disruption or enhancement of other protein-protein interactions, by opsonization of phagocytosis, substantially increasing the likelihood of immune recognition and destruction of pathogenic or pathologic agents.

For a B cell to produce a high affinity or high avidity antibody, a multi-step process called affinity maturation is required. During affinity maturation, genetic changes in the B cell receptor (BCR) occur. Following these genetic changes, a guess-and-check, evolutionary-like process occurs. This is a competitive process in which high binding strength leads to more contact with accessory cells that give positive survival signals. Accessory cells include, but are not limited to: T cells, B cells, monocytes, macrophages, dendritic cells, natural killer cells, etc. A null BCR rearrangement ends the process of affinity maturation, and it no longer receives survival signals from accessory cells that are presenting the antigen or cross-linking of its own BCR that can provide additional positive feedback. Therefore, a higher affinity BCR rearrangement and random mutation give the B cell positive feedback, encouraging B cell division, more receptor rearrangement, and more random mutation, while a lower affinity BCR rearrangement may result in cell death or anergy. After several rounds of selection in this guess-and-check sequence, a high affinity B cell differentially survives and transitions into a plasma cell. Plasma cells circulate in the blood stream and secrete high amounts of antibody to assist an immune response. Affinity maturation occurs mostly in lymph node organs over the period of several days.

The lymph node consists of a large collection of immune cells, primarily B cells, T cells, and follicular dendritic cells (FDCs) within a reticular network. Lymph nodes enable the widespread intercellular interaction required for a full-scale immune response by increasing the proximity of cells to one another. B cell receptor rearrangement is supported by secondary survival signals from accessory cells. These proximity-based cellular interactions require or are significantly improved by a particular three-dimensional (3D) spatiotemporal arrangement of immune cells, found within the lymph node.

Three-dimensional cell movement and spatiotemporal arrangement of cells is critical for several cell-based processes, including cell differentiation and cellular responses to external or internal stimuli. During affinity maturation of B cells, the immune cells involved physically compartmentalize in the lymph node into regions that contain dividing B cells (i.e., dark zone), non-dividing B cells (i.e., light zone), and supporting accessory cells, as shown in FIG. 16. Compartmentalization of the immune cells, followed by rearrangement during activation, indicates a dependence upon this organization for the proper development of high-affinity antibodies. While B cells undergo affinity maturation, they move between compartments in the lymph node, crawling across other cells and collagen networks, as shown in FIG. 17. This disclosure describes a non-toxic, printing process of cell-containing collagen networks at a millimeter, micron, or sub-micron resolution such that a lymphoid organ or organoid containing other cell types with finite cell compartmentalization may be created for purposes including, but not limited to, antibody generation.

Development of an antigen-specific antibody in a synthetic tissue de novo after antigen challenge or vaccination of the organoid indicates functional cell-cell interactions and a functionally responsive tissue that can support complex cell-cell interactions over the course of days to weeks to months.

Antibodies have been leveraged for therapeutic purposes owing to their high efficacy and versatility in targeting, neutralizing, and/or opsonizing biological agents relevant to a number of disease states including cancer, autoimmune disease, and infectious disease. However, current methods for the discovery and production of antibodies for therapeutic or research uses are time-consuming and costly. The standard method of antibody production requires the use of animals, often mice or other rodents, rabbits, chickens, horses, or non-human primates, which are injected with an antigen and exsanguinated for B cell collection after exhibiting an immune response. Antibodies produced by this method that are intended for use against human targets (e.g., for therapeutic purposes) require an additionally laborious humanization step, which may change the binding affinity of the target, while providing no guarantee of safety or efficacy in humans. Other methods, such as phage display, use a predefined antibody library or set of sequences coupled with some method of selection for the protein of interest. Often these libraries do not yield unique or high-affinity sequences. Furthermore, as a pre-defined group of proteins, they may not yield the ability to respond to a novel infectious agent. Our technology solves the dual problems of (a) the reliance on animal models for antibody discovery and (b) the inability to produce high-affinity, unique antibodies using a high-throughput model derived from humans.

The described method involves the use of a light source, including, but not limited to, white light, blue light, green light, and single- or multi-photon laser sources of any wavelength. Light may be projected in two or three dimensions.

Two-dimensional (2D) projection is achieved by two-dimensional projection of a single axial plane with a digital micromirror device (DMD) or spatial light modulator (SLM) that has light placed only in specific regions where polymerization of a material is desired.

Three-dimensional projection, if used, may be achieved by holographic projection of light through use of a two light modulating systems in series, as disclosed in commonly invented U.S. Provisional Patent Appl. No. 62/469,948, entitled MULTI-PHOTON TISSUE PRINTING, which is incorporated herein by reference. Polymerization of biomaterials has been described and implemented for use in bioprinting of materials for cell scaffolds. The method described herein involves projecting a light source into a bath containing polymerizable material to encapsulate cells as polymerization occurs. By comparison, alternate in-media polymerization-based tissue engineering approaches use light projection to produce a 3D scaffold that may later be seeded with cells. Encapsulating cells during the polymerization process rather than seeding increases the precision with which cells may be placed; resolution that may be achieved within the polymerized space is further increased by using a two-photon light source rather than a standard single-photon light source. The use of two-photon light sources to induce polymerization both eliminates or substantially reduces the toxicity of light to cells and speeds printing to improve cell viability and growth. Multiphoton and single-photon laser methods are superior to extrusion printing in terms of resolution that may be attained and speed at which large or complex structures may be printed. Alternatively, photons of longer wavelength may be used to reduce damage to cells, and/or less intense light or shorter light exposure time may be used. Additionally, printing simultaneously in three-dimensions by holographic projection of the light source in the desired polymerization pattern substantially reduces print time, also reducing stress to cells as a result of light exposure or time outside of an incubator.

The most commonly used medical devices for wound closure, wound patching as in a stent, knitting, or fusing of tissues including bone and skin, are created from biologically inert materials. Many of these materials may dissolve over time, but many remain permanent features for many years after surgery and may induce complications or hinder the healing process.

Some more advanced materials and medical devices used for surgical wound closure or tissue repair are cell-seeded after three-dimensional extrusion printing to introduce stem cells or other cell types that might be beneficial to wound healing or closure. However, cell seeding into biologically inert materials have low viability and low survival profiles for cells and thus, incomplete delivery of beneficial cells.

Tissue implants for the promotion of tissue healing or improvement of function are often in the form of cell suspension injections or small devices that do not breach the 200-300 micrometer limit of diffusion for oxygen, nutrients and waste products, or are mostly a-cellular. Furthermore, tissue implants do not contain cells printed in place that may remodel the print material and grow within the printed material, a significant hindrance to the development of a functional tissue insert that may incorporate into the implant environment.

The engineering of medical devices that contain cells able to remodel and growth within the implanted device are limited by print resolution, lack of structurally resilient biomaterials that may be used in extrusion printing, cytotoxicity of high-resolution extrusion printing, and techniques to introduce cells into the 3D printed medical devices after printing. In addition, 3-dimensional extrusion printing of high-complexity devices is slow, often taking hours or days to complete a single print cycle. This makes production and scale-up of on-demand cell-containing devices difficult to achieve.

This disclosure describes the development and use of three-dimensional lithography enabled by holographic light projection using a technique called optical wave-front shaping for the purpose of bioprinting cell containing structures and materials. The cell containing structures and materials are designed specifically to maintain structural properties such as tensile strength, shear and compression force resistance, compressibility or other properties that allow for compatibility with surgical techniques, specifications, and native tissue and organ structures while being fully biologically compatible. Hardening or polymerization of the biomaterials may be actuated by light or laser interactions with the printing materials at specific points in three dimensional space. Printing materials include both biomaterials that are monomeric and doping or actuating agents that are non-cytotoxic but react to light or specific wavelengths of light. Biologically compatible devices or structures printed containing embedded or trapped cells allow for remodeling and break-down or resorption of the implanted device that is used to deliver cells to the desired site for the purpose of, though not limited to, healing or augmentation, or replacement of tissue function.

SUMMARY

In an aspect, the present disclosure provides a method for producing one or more immunological proteins, comprising: (a) providing a media chamber comprising a medium comprising (i) a plurality of cells and (ii) one or more polymer precursors; (b) directing at least one energy beam to the medium in the media chamber along at least one energy beam path that is patterned into a three-dimensional (3D) projection in accordance with computer instructions for printing a 3D lymphoid organoid in computer memory, to form at least a portion of the 3D lymphoid organoid comprising (i) at least a subset of the plurality of cells, and (ii) a polymer formed from the one or more polymer precursors; and (c) subjecting the at least the portion of the 3D lymphoid organoid to conditions sufficient to stimulate production of the one or more immunological proteins.

In some embodiments, the conditions comprise exposing the at least the portion of the 3D lymphoid organoid to an antigen in order to stimulate production of the one or more immunological proteins. In some embodiments, the method further comprises: (d) extracting one or more immunological proteins from the at least portion of the 3D lymphoid organoid. In some embodiments, the immunological proteins are selected from the list consisting of antibodies, T-cell receptors and cancer immunotherapeutics. In some embodiments, the plurality of cells is from a subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of the 3D lymphoid organoid is selected from the list consisting of spherical, oval, ovate, ovoid, square, rectangular, cuboid, any polygonal shape, free-form, and tear-drop shape. In some embodiments, the polymer of the at least of the portion of 3D lymphoid organoid forms a network. In some embodiments, the network is reticular, amorphous or a net. In some embodiments, the amorphous network is designed to facilitate cellular interactions. In some embodiments, the amorphous network is designed to facilitate movement between or within cellular niches.

In another aspect, the present disclosure provides a method for producing one or more immunological proteins, comprising (i) printing a three-dimensional (3D) lymphoid organoid comprising a matrix containing a plurality of cells, and (ii) treating the 3D lymphoid organoid to produce the one or more immunological proteins.

In some embodiments, the immunological proteins are selected from the list consisting of antibodies, T-cell receptors and cancer immunotherapeutics. In some embodiments, the plurality of cells is from the subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In another aspect, the present disclosure provides a method for producing one or more immunological proteins, comprising: (a) providing a media chamber comprising a first medium, wherein the first medium comprises a first plurality of cells and a first polymeric precursor; (b) directing at least one energy beam to the first medium in the media chamber along at least one energy beam path in accordance with computer instructions for printing a three-dimensional (3D) lymphoid organoid in computer memory, to subject at least a portion of the first medium in the media chamber to form a first portion of the 3D lymphoid organoid; (c) providing a second medium in the media chamber, wherein the second medium comprises a second plurality of cells and a second polymeric precursor, wherein the second plurality of cells is of a different type than the first plurality of cells; (d) directing at least one energy beam to the second medium in the media chamber along at least one energy beam path in accordance with the computer instructions, to subject at least a portion of the second medium in the media chamber to form a second portion of the 3D lymphoid organoid; and (e) subjecting the first and second portions of the 3D lymphoid organoid to conditions sufficient to stimulate production of the one or more immunological proteins.

In some embodiments, the conditions comprise exposing the first and second portions of the 3D lymphoid organoid to an antigen in order to stimulate production of the one or more immunological proteins. In some embodiments, the method further comprises: (f) extracting one or more immunological proteins from the first and second portions of the 3D lymphoid organoid. In some embodiments, the immunological proteins are selected from antibodies, T-cell receptors and cancer immunotherapeutics. In some embodiments, the first plurality of cells and the second plurality of cells are from a subject. In some embodiments, the first plurality of cells and the second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of the 3D lymphoid organoid is selected from the list consisting of spherical, oval, ovate, ovoid, square, rectangular, cuboid, any polygonal shape, free-form, and tear-drop shape. In some embodiments, the polymer of the at least of the portion of 3D lymphoid organoid forms a network. In some embodiments, the network is reticular, amorphous or a net. In some embodiments, the amorphous network is designed to facilitate cellular interactions. In some embodiments, the amorphous network is designed to facilitate movement between or within cellular niches.

In another aspect, the present disclosure provides a method of producing one or more immunological proteins, comprising (i) printing a three-dimensional (3D) lymphoid organoid comprising a matrix containing a first plurality of cells and a second plurality of cells, and (ii) treating the 3D lymphoid organoid to produce the one or more immunological proteins. In some embodiments, the immunological proteins are selected from the list consisting of antibodies, T-cell receptors and cancer immunotherapeutics. In some embodiments, the first and the second plurality of cells are from the subject. In some embodiments, the first and the second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ.

In another aspect, the present disclosure provides a method for using a three-dimensional (3D) cell-containing matrix, comprising: (a) providing a media chamber comprising a medium comprising (i) a plurality of cells and (ii) one or more polymer precursors; (b) directing at least one energy beam to the medium in the media chamber along at least one energy beam path that is patterned into a three-dimensional (3D) projection in accordance with computer instructions for printing the 3D cell-containing medical device in computer memory, to form at least a portion of the 3D cell-containing matrix comprising (i) at least a subset of the plurality of cells, and (ii) a polymer formed from the one or more polymer precursors; and (c) positioning the 3D cell-containing matrix in a subject.

In some embodiments, the plurality of cells is from the subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D cell-containing matrix forms suture, stent, staple, clip, strand, patch, graft, sheet, tube, pin, or screws. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a method for using a three-dimensional (3D) cell-containing matrix, comprising (i) printing the 3D cell-containing matrix comprising a plurality of cells, and (ii) positioning the 3D cell-containing matrix in a subject.

In some embodiments, the plurality of cells is from the subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a method for using a three-dimensional (3D) cell-containing matrix, comprising: (a) providing a media chamber comprising a first medium, wherein the first medium comprises a first plurality of cells and a first polymeric precursor; (b) directing at least one energy beam to the first medium in the media chamber along at least one energy beam path in accordance with computer instructions for printing the 3D cell-containing matrix in computer memory, to subject at least a portion of the first medium in the media chamber to form a first portion of the 3D cell-containing matrix; (c) providing a second medium in the media chamber, wherein the second medium comprises a second plurality of cells and a second polymeric precursor, wherein the second plurality of cells is of a different type than the first plurality of cells; (d) directing at least one energy beam to the second medium in the media chamber along at least one energy beam path in accordance with the computer instructions, to subject at least a portion of the second medium in the media chamber to form a second portion of the 3D cell-containing matrix; and (e) positioning the first and second portions of the 3D cell-containing matrix in a subject.

In some embodiments, the first and the second plurality of cells is from the subject. In some embodiments, the first and the second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a method of using a three-dimensional (3D) cell-containing matrix, comprising (i) printing the 3D cell-containing matrix comprising a first plurality of cells and a second plurality of cells, wherein the first plurality of cells is different from the second plurality of cells, and (ii) positioning the 3D cell-containing matrix in a subject.

In some embodiments, the first and second plurality of cells are from the subject. In some embodiments, the first and second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a system for producing one or more immunological proteins, comprising: (a) a media chamber configured to contain a medium comprising a plurality of cells and one or more polymer precursors; (b) at least one energy source configured to direct at least one energy beam to the media chamber; and (c) one or more computer processors operatively coupled to the at least one energy source, wherein the one or more computer processors are individually or collectively programmed to (i) receive computer instructions for printing a three-dimensional (3D) lymphoid organoid from computer memory; (ii) direct the at least one energy source to direct the at least one energy beam to the medium in the media chamber along at least one energy beam path in accordance with the computer instructions, to subject at least a portion of the polymer precursors to form at least a portion of the 3D lymphoid organoid, and (iii) subject the at least portion of the 3D lymphoid organoid to conditions sufficient to stimulate production of the one or more immunological proteins.

In some embodiments, the conditions sufficient to stimulate production of the one or more immunological proteins comprises exposing the at least the portion of the 3D lymphoid organoid to an antigen in order to stimulate production of the one or more immunological proteins.

In another aspect, the present disclosure provides a system for producing one or more immunological proteins, comprising: (a) a media chamber configured to contain a first medium comprising a first plurality of cells and a first plurality of polymer precursors; (b) at least one energy source configured to direct at least one energy beam to the media chamber; and (c) one or more computer processors operatively coupled to the at least one energy source, wherein the one or more computer processors are individually or collectively programmed to (i) receive computer instructions for printing a three-dimensional (3D) lymphoid organoid from computer memory, (ii) direct the at least one energy source to direct the at least one energy beam to the first medium in the media chamber along at least one energy beam path in accordance with the computer instruction, to subject at least a portion of the first polymer precursors to form at least a portion of the 3D lymphoid organoid; (iii) direct the at least one energy source to direct the at least one energy beam to a second medium in the media chamber along at least one energy beam path in accordance with the computer instructions, to subject at least a portion of the second medium in the media chamber to form at least a second portion of the 3D lymphoid organoid, wherein the second medium comprises a second plurality of cells and a second plurality of polymeric precursors, wherein the second plurality of cells is of a different type than the first plurality of cell; and (iv) subject the first and second portions of the 3D lymphoid organoid to conditions sufficient to stimulate production of the one or more immunological proteins.

In some embodiments, the conditions sufficient to stimulate production of the one or more immunological proteins comprises exposing the first and second portions of the 3D lymphoid organoid to an antigen in order to stimulate production of the one or more immunological proteins.

In another aspect, the present disclosure provides a method of producing a population of human immunological proteins, comprising: using a multi-photon laser bio-printing system to bio-print a three-dimensional lymphoid organoid; exposing the three-dimensional lymphoid organoid to an antigen in order to stimulate production of the population of human immunological proteins; and extracting the population of human immunological proteins from the three-dimensional lymphoid organoid.

In another aspect, the present disclosure provides a method of producing a population of human immunological proteins, comprising: (a) providing a medium comprising (i) a plurality of cells and (ii) one or more polymer precursors; (b) depositing at least one layer of the medium onto a substrate; (c) subjecting the at least one layer of the medium to an energy source to form at least a portion of the 3D lymphoid organoid comprising (i) at least a subset of the plurality of cells, and (ii) a biogel formed from the one or more polymer precursors; and (d) subjecting the at least the portion of the 3D lymphoid organoid to conditions sufficient to stimulate production of the one or more immunological proteins.

In some embodiments, the conditions comprise exposing the at least the portion of the 3D lymphoid organoid to an antigen in order to stimulate production of the one or more immunological proteins. In some embodiments, the the method further comprises: (d) extracting one or more immunological proteins from the at least portion of the 3D lymphoid organoid. In some embodiments, the immunological proteins are selected from the list consisting of antibodies, T-cell receptors and cancer immunotherapeutics. In some embodiments, the plurality of cells is from a subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the medium comprises a photoinitiator, a cross-linker, collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof. In some embodiments, the energy source is a laser, a heat source, a light source, or any combination thereof.

The present disclosure provides methods and systems for rapid generation of cell-containing structures using spatial light modulation of multi-photon excitation sources. In some embodiments, the cell-containing structures may be multi-layered vascularized tissues, cell-containing devices, or cell-containing materials. Using this approach, a method for rapid creation of cell-containing structures is provided by layering cell-size specific nets with embedded mechanical and, or biological elements such as microvasculature. The deposition of cells contained in nets of collagen or another biologically compatible, or inert material, is a rapid, iterative, process based on a three dimensional (holographic) projection, a two-dimensional projection, and/or in any planar axis such as x, y, x, z, or y, z, which may be combined with scanning of the multi-photon laser excitation. Three dimensional scanning, two-dimensional scanning, and raster scanning may be used simultaneously in various combinations to achieve rapid creation of a complete structure. The dynamic shifts between modes of laser projection allows for rapid generation of complex structures in a large field of view, while maintaining fine micrometer to nanometer resolution. This method allows for rapid production of large (e.g., up to about 5 centimeters (cm)) multi-layered and small vasculature (e.g. 1-10 micrometers (μm)) single-cell layered vasculature.

The present disclosure permits layering of multiple cell types in two dimensions and/or three dimensions such that tissue may be constructed in a manner that is not limited by multiple cell types, sizes, or complexities. In some cases, this is achieved using multiphoton (e.g., two-photon) excitation light, as may be provided, for example, by a laser.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Another aspect of the present disclosure provides for the generation of lymphoid organs and organoids by photolithography, using white light, single photon excitation, or multiphoton laser excitation projected in two-dimensional sequential planes or three-dimensional holograms. Lymph node organs and organoids may be printed from collagen or other biologically compatible materials. Active, responsive synthetic human immune tissues may be produced by the methods disclosed herein Immunologically responsive tissues may be produced by the methods disclosed herein. The synthetic immunologically responsive tissues, produced by the methods disclosed herein, may be used to develop novel products and query immune responses of living individuals. Using this approach, a method for rapid generation of novel antibodies is provided by exposing the lymphoid organ to an antigen of choice and allowing physiologic processes of antibody clonal selection and expansion to occur. The synthetic immunologically responsive tissues, produced by the methods disclosed herein, may be used to create novel antibodies from a single blood donation, replacing hundreds of animal or human surrogates for antibody production in a single set of 96 well plates. The synthetic immunologically responsive tissues, produced by the methods disclosed herein, generate antibody libraries or queries of immune system responses in a high throughput manner. The synthetic organoids, produced by the methods disclosed herein, may pharmaceutically test biologic and/or non-biologic drug compounds or drug combinations.

Another aspect of the present disclosure provides for methods of producing a range of cell-containing devices or materials for medical purposes that are 3 dimensionally printed with multi-photon and, or single photon, or white-light lithography, including, but not limited to, surgical wound closure and tissue repair. Devices and materials may include sutures, staples, clips, strands, patches, grafts, sheets, tubes, pins, screws, and similar structures intended to be used in a living subject. Such devices and materials allow for the delivery of cells, including stem cells, into a living subject, potentially expediting wound healing and/or tissue repair or altering cell composition at the site of use in some desired manner.

Another aspect of the present disclosure, provides for methods for implantation of a multi-photon 3 dimensionally printed cell-containing device or structure with a desired physiological function, including functions that replicate those of native organs and organoids, to supplement naturally-occurring function in a living subject. In this iteration, the device is not intended for cell delivery or regeneration of native structure or function, but rather to recapitulate the native function of a tissue in of itself, whether in conjunction with native function to augment or assist in function or operate independently replacing native tissue function.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which:

FIG. 2A illustrates the media chamber containing media comprising a first cell group. FIG. 2B illustrates the media chamber containing media comprising a second cell group.

FIG. 2C illustrates delivery of pulses of the multi-photon laser beam to the media. FIG. 2D illustrates an embodiment wherein the cell-containing scaffolding is printed along the bottom of the media chamber containing media.

FIG. 3A illustrates an embodiment of a laser system having a single multi-photon laser source. FIG. 3B illustrates an embodiment of a laser system having multiple laser lines. FIG. 3C illustrates an embodiment of a laser system comprising multiple laser lines, photomultipliers (PMTs), and an objective lens.

FIG. 4A illustrates an embodiment of the printing system comprising a beam expander, an optical focusing lens, an additional beam focusing lens, and no axicon or TAG lens. FIG. 4B illustrates an embodiment of the printing system comprising a beam expander, an optical focusing lens, an additional laser focusing lens, and an axicon or TAG lens. FIG. 4C illustrates a Z-step projection printing setup comprising a single SLM or DMD for 2D, x, y sheet or hologram projection for printing around cells and resultant structures printed with given Z-steps.

FIG. 5A illustrates an embodiment of the multi-photon tissue print head comprising a single, upright objective lens. FIG. 5B illustrates an embodiment of the multi-photon tissue print head having inverted optics for imaging structures.

FIG. 6A illustrates the fiber optic cable accessory and fiber optic cable. FIG. 6B illustrates the fiber optic cable accessory being used to print the desired complex tissue structure.

FIG. 18A illustrates a B cell germinal center responding to antigen where B cells move between compartmentalized zones known as dark and light zones as part of the maturation and selection process for development of high-affinity antibodies. FIG. 18B illustrates a thymic-like development niche in which T cells undergo selection and maturation in a series of sequential steps as they move from the cortex-like thymic tissue to the medullary-like thymic tissue.

FIG. 27 illustrates cells printed onto a lattice structure.

FIGS. 28A-28E show clusters of human pluripotent stem cell-derived insulin-producing cells encapsulated by holographic printing. FIG. 28A shows images of clusters of encapsulated cells expressing enhanced green fluorescence protein (eGFP). FIG. 28B shows a graph corresponding to the amount of human C-peptide produced by the encapsulated cells. FIG. 28C shows a first image of the encapsulated cells expressing eGFP, five days post-encapsulation. FIG. 28D shows a second image of the encapsulated cells expressing eGFP, five days post-encapsulation.

FIG. 28E shows an image of the encapsulating structure.

FIG. 29A shows a representative, computer-generated rendering of the micro-stent. FIG. 29B shows an image of a side view of the printed micro-stent. FIG. 29C shows an image of a cross-sectional view of the printed micro-stent.

FIGS. 30A-30B show images of compressibility and resiliency testing of the holographically printed micro-stent. FIG. 30A shows a series of images demonstrating repeated compression of the micro-stent against a solid surface. FIG. 30B shows a series of images demonstrating the resiliency of the micro-stent.

FIG. 31A shows a computer-generated image of the micromesh network. FIG. 31B shows an image of the micromesh network. FIG. 31C shows a close up image of the micromesh network.

FIG. 31D shows a series of images of the micromesh network subjected to lateral compression.

FIG. 31E shows a series of images of the micromesh network during handling with tweezers.

FIG. 32A shows an image of a printed collagen matrix containing B cells, T cells, and antigen presenting cells (APCs). FIG. 32B shows an image representing a mixed cell population of B cells, T cells, and APCs in the printed collagen matrix.

FIG. 32C shows an image of the population of B cells, T cells, and APCs in a tissue culture well, not in the printed collagen matrix. FIG. 32D shows an image of LNO and clusters of cells 24 hours after the addition of antigen. FIG. 32E shows an image of the printed lymph node organoids and cells clusters 72 hours after addition of the antigen pulse. FIG. 32F shows an image of the printed LNO and cells clusters 120 hours after addition of the antigen. FIG. 32G shows a graph representing the production of interleukin-4 (IL-4) by the LNO. FIG. 32H shows a graph representing the production of IL-2 by LNO.

FIG. 33A shows a graph representing the concentration of protein in LNO samples. FIG. 33B shows an image of an SDS-PAGE gel containing purified human IgG isolated from the printed LNO media. FIG. 33C shows an image of an SDS-PAGE gel containing unpurified human IgG isolated from the printed LNO media.

FIG. 34A shows a graph representing the absorbance at 450 nanometers (nm) and 570 nm of the samples tested using an ELISA. FIG. 34B shows two graphs representing sub-cloned unique hybridomas that were further assayed for the presence of specific antigen-reactive human IgG.

DETAILED DESCRIPTION

Figure 1:
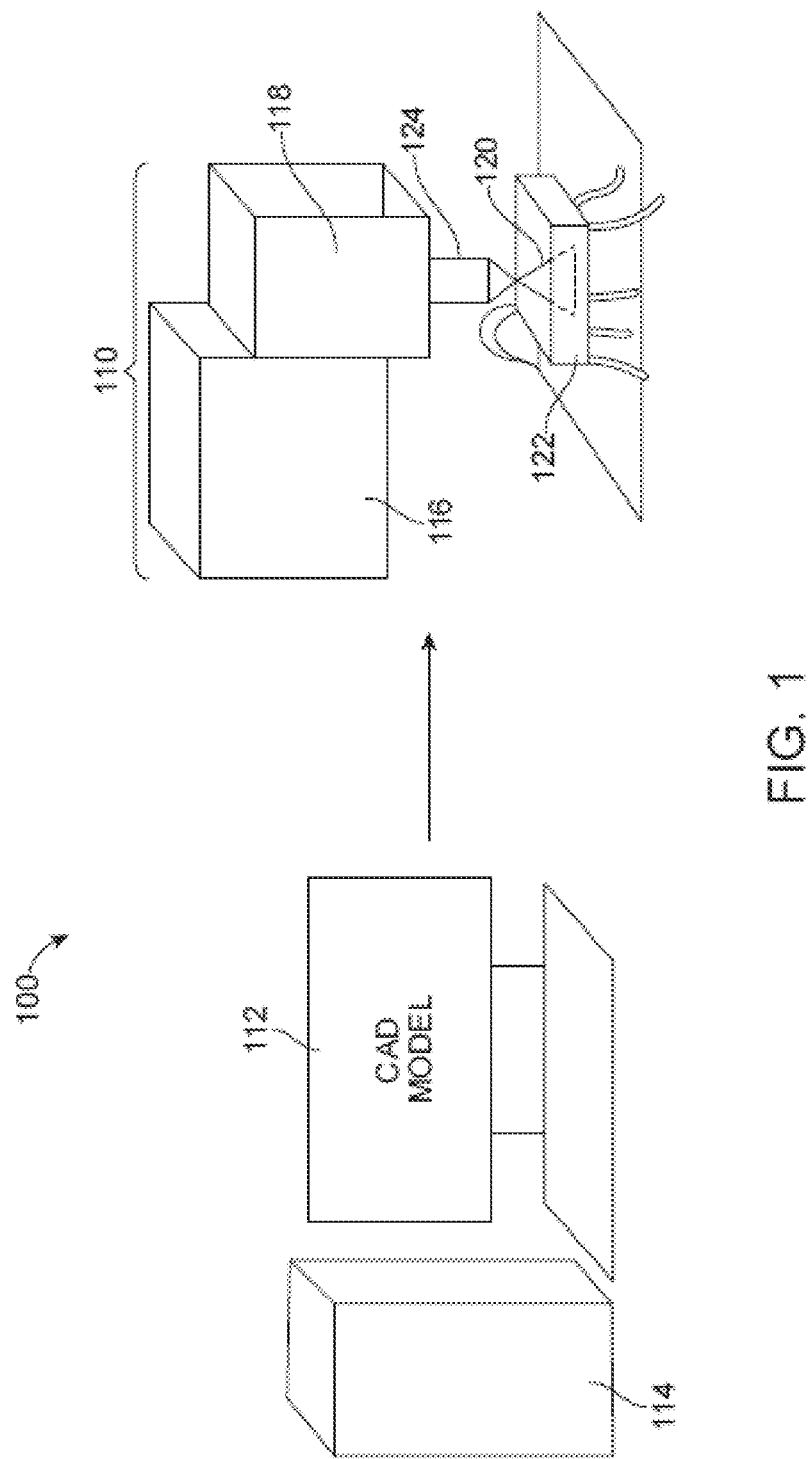
FIG. 1 illustrates an embodiment of a system for rapid multi-photon printing of a desired tissue is illustrated.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" refers to an amount that is near the stated amount by about 10%, 5%, or 1%, including increments therein. For example, "about" or "approximately" may mean a range including the particular value and ranging from 10% below that particular value and spanning to 10% above that particular value.

The term "biological material," as used herein, generally refers to any material that may serve a chemical or biological function. Biological material may be biologically functional tissue or functional tissue, which may be a biological structure that is capable of serving, or serving, a biomechanical or biological function. Biologically functional tissue may comprise cells that are within diffusion distance from each other, comprises at least one cell type wherein each cell is within diffusion distance of a capillary or vascular network component, facilitates and/or inhibits the fulfillment of protein function, or any combination thereof. Biologically functional tissue may be at least a portion of tissue or an organ, such as a vital organ. In some examples, the biological material may advance drug development; for example, by screening multiple cells or tissue with different therapeutic agents.

Biological material may include a matrix, such as a polymeric matrix, biogel, hydrogel, or polymeric scaffold, including one or more other types of material, such as cells. Biological material may include lymphoid organs and organoids. Biological material may be derived from human or animal sources of primary cells, cell lines, stem cells, stem cell lines, differentiated stem cells, transdifferentiated stem cells, autologous cells, allogeneic cells, pluripotent stem cells, embryonic stem cells, induced pluripotent stem cells, or any combination thereof. Biological material may be in various shapes, sizes or configurations. In some instances, biological material may be consumable by a subject (e.g., an animal), such as meat or meat-like material.

The term "three-dimensional printing" (also "3D printing"), as used herein, generally refers to a process or method for generating a 3D part (or object). Such process may be used to form a 3D part (or object), such as a 3D biological material.

The term "energy beam," as used herein, generally refers to a beam of energy. The energy beam may be a beam of electromagnetic energy or electromagnetic radiation. The energy beam may be a particle beam. An energy beam may be a light beam (e.g., gamma waves, x-ray, ultraviolet, visible light, infrared light, microwaves, or radio waves). The light beam may be a coherent light beam, as may be provided by light amplification by stimulated emission of radiation ("laser"). In some examples, the light beam is generated by a laser diode or a multiple diode laser.

The term "allogenic," as used herein, refers to the plurality of cells are obtained from a genetically non-identical donor. For example, allogenic cells are extracted from a donor and returned back to a different, genetically non-identical recipient.

The term "autologous," as used herein, refers to the plurality of cells are obtained from a genetically identical donor. For example, autologous cells are extracted from a patient and returned back to the same, genetically identical individual (e.g., the donor).

The term "pluripotent stem cells" (PSCs), as used herein, refers to cells capable, under appropriate conditions, of producing different cell types that are derivatives of all of the 3 germinal layers (i.e. endoderm, mesoderm, and ectoderm). Included in the definition of pluripotent stem cells are embryonic stem cells of various types including human embryonic stem (hES) cells, human embryonic germ (hEG) cells; non-human embryonic stem cells, such as embryonic stem cells from other primates, such as Rhesus stem cells, marmoset stem cells; murine stem cells; stem cells created by nuclear transfer technology, as well as induced pluripotent stem cells (iPSCs).

The term "embryonic stem cells" (ESCs), as used herein, refers to pluripotent stem cells that are derived from a blastocyst before substantial differentiation of the cells into the three germ layers (i.e. endoderm, mesoderm, and ectoderm). ESCs include any commercially available or well established ESC cell line such as H9, H1, H7, or SA002.

The term "induced pluripotent stem cells" or "iPSCs," as used herein, refers to somatic cells that have been reprogrammed into a pluripotent state resembling that of embryonic stem cells. Included in the definition of iPSCs are iPSCs of various types including human iPSCs and non-human iPSCs, such as iPSCs derived from somatic cells that are primate somatic cells or murine somatic cells.

The term "energy source," as used herein, refers to a laser, such as a fiber laser, a short-pulsed laser, or a femto-second pulsed laser; a heat source, such as a thermal plate, a lamp, an oven, a heated water bath, a cell culture incubator, a heat chamber, a furnace, or a drying oven; a light source, such as white light, infrared light, ultraviolet (UV) light, near infrared (NIR) light, visible light, or a light emitting diode (LED); a sound energy source, such as an ultrasound probe, a sonicator, or an ultrasound bath; an electromagnetic radiation source, such as a microwave source; or any combination thereof.

The term "biogel," as used herein, refers to a hydrogel, a biocompatible hydrogel, a polymeric hydrogel, a hydrogel bead, a hydrogel nanoparticle, a hydrogel microdroplet, a solution with a viscosity ranging from at least about $10\times10^{-4}$ Pascal-second (Pa·s) to about 100 Pa·s or more when measured at 25 degrees Celsius (° C.), a hydrogel comprising non-hydrogel beads, nanoparticles, microparticles, nanorods, nanoshells, liposomes, nanowires, nanotubes, or a combination thereof; a gel in which the liquid component is water; a degradable hydrogel; a non-degradable hydrogel; a resorbable hydrogel; a hydrogel comprising naturally-derived polymers; or any combination thereof.

The present disclosure provides methods and systems for printing a three-dimensional (3D) biological material. In an aspect, a method for printing the 3D biological material comprises providing a media chamber comprising a medium comprising (i) a plurality of cells and (ii) one or more polymer precursors. Next, at least one energy beam may be directed to the medium in the media chamber along at least one energy beam path that is patterned into a 3D projection in accordance with computer instructions for printing the 3D biological material in computer memory. This may form at least a portion of the 3D biological material comprising (i) at least a subset of the plurality of cells, which at least the subset of the plurality of cells comprises cells of at least two different types, and (ii) a polymer formed from the one or more polymer precursors.

Methods and systems of the present disclosure may be used to print multiple layers of a 3D object, such as a 3D biological material, at the same time. Such 3D object may be formed of a polymeric material, a metal, metal alloy, composite material, or any combination thereof. In some examples, the 3D object is formed of a polymeric material, in some cases including biological material (e.g., one or more cells or cellular components). In some cases, the 3D object may be formed by directing an energy beam (e.g., a laser) as a 3D projection (e.g., hologram) to one or more precursors of the polymeric material, to induce polymerization and/or cross-linking to form at least a portion of the 3D object. This may be used to form multiple layers of the 3D object at the same time.

As an alternative, the 3D object may be formed of a metal or metal alloy, such as, e.g., gold, silver, platinum, tungsten, titanium, or any combination thereof. In such a case, the 3D object may be formed by sintering or melting metal particles, as may be achieved, for example, by directing an energy beam (e.g., a laser beam) at a powder bed comprising particles of a metal or metal alloy. In some cases, the 3D object may be formed by directing such energy beam as a 3D projection (e.g., hologram) into the powder bed to facilitate sintering or melting of particles. This may be used to form multiple layers of the 3D object at the same time. The 3D object may be formed of an organic material such as graphene. The 3D object may be formed of an inorganic material such as silicone. In such cases, the 3D object may be formed by sintering or melting organic and/or inorganic particles, as may be achieved, for example, by directing an energy beam (e.g., a laser beam) at a powder bed comprising particles of an organic and/or inorganic material. In some cases, the 3D object may be formed by directing such energy beam as a 3D projection (e.g., hologram) into the powder bed to facilitate sintering or melting of organic and/or inorganic particles.

The depth of the energy beam penetration may be dictated by the interaction of the beam wavelength and the electron field of a given metal, metal alloy, inorganic material, and/or organic material. The organic material may be graphene. The inorganic material may be silicone. These particles may be functionalized or combined in to allow for greater interaction or less interaction with a given energy beam.

In some examples, the at least one energy beam is at least 1, 2, 3, 4, 5, 6, 7, 8, 9, 10, 20, 30, 40, 50, 100, or more energy beams. The at least one energy beam may be or include coherent light. In some cases, the at least one energy beam is a laser beam.

The at least one energy beam may be directed as an image or image set. The image may be fixed with time or changed with time. The at least one energy beam may be directed as a video.

The computer instructions may correspond to a computer model or representation of the 3D biological material. The computer instructions may be part of the computer model. The computer instructions may comprise a set of images corresponding to the 3D biological material.

The at least one energy beam may be directed as a holographic image or video. This may enable different points in the medium to be exposed to the at least one energy beam at the same time, to, for example, induce formation of a polymer matrix (e.g., by polymerization) at multiple layers at the same time. In some cases, a 3D image or video may be projected into the medium at different focal points using, e.g., a spatial light modulator (SLM).

The computer instructions may include and/or direct adjustment of one or more parameters of the at least one energy beam as a function of time during formation of the 3D biological material, such as, for example, application of power to a source of the at least one energy beam (e.g., laser on/off). Such adjustment may be made in accordance with an image or video (e.g., holographic image or video) corresponding to the 3D biological material. Alternatively, or in addition to, the computer instructions may include and/or direct adjustment of a location of a stage upon which the 3D biological material is formed.

In some cases, during or subsequent to formation of the 3D biological material, at least a portion of the at least the subset of the plurality of cells may be subjected to differentiation to form the cells of the at least two different types. This may be employed, for example, by exposing the cells to an agent or subjecting the cells to a condition that induces differentiation. Alternatively, or in addition to, the cells may be subjected to de-differentiation or induction of cell quiescence.

Another aspect of the present disclosure provides a method for printing a 3D biological material, providing a media chamber comprising a first medium. The first medium may comprise a first plurality of cells and a first polymeric precursor. At least one energy beam may be directed to the first medium in the media chamber along at least one energy beam path in accordance with computer instructions for printing the 3D biological material, to subject at least a portion of the first medium in the media chamber to form a first portion of the 3D biological material. Next, a second medium may be provided in the media chamber. The second medium may comprise a second plurality of cells and a second polymeric precursor. The second plurality of cells may be of a different type than the first plurality of cells. Next, at least one energy beam may be directed to the second medium in the media chamber along at least one energy beam path in accordance with the computer instructions, to subject at least a portion of the second medium in the media chamber to form at least a second portion of the 3D biological material.

In another aspect of the present disclosure, a system for printing a 3D biological material comprises a media chamber configured to contain a medium comprising a plurality of cells comprising cells of at least two different types and one or more polymer precursors; at least one energy source configured to direct at least one energy beam to the media chamber; and one or more computer processors operatively coupled to the at least one energy source, wherein the one or more computer processors are individually or collectively programmed to (i) receive computer instructions for printing the 3D biological material from computer memory; and (ii) direct the at least one energy source to direct the at least one energy beam to the medium in the media chamber along at least one energy beam path in accordance with the computer instructions, to subject at least a portion of the polymer precursors to form at least a portion of the 3D biological material.

In another aspect, a system for printing a 3D biological material, comprising: a media chamber configured to contain a medium comprising a plurality of cells and a plurality of polymer precursors; at least one energy source configured to direct at least one energy beam to the media chamber; and one or more computer processors operatively coupled to the at least one energy source, wherein the one or more computer processors are individually or collectively programmed to (i) receive computer instructions for printing the 3D biological material from computer memory; (ii) direct the at least one energy source to direct the at least one energy beam to the medium in the media chamber along at least one energy beam path in accordance with the computer instructions, to subject at least a portion of the polymer precursors to form at least a portion of the 3D biological material; and (iii) direct the at least one energy source to direct the at least one energy beam to a second medium in the media chamber along at least one energy beam path in accordance with the computer instructions, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

In another aspect of the present disclosure, methods for printing a three-dimensional (3D) object, may comprise directing at least one energy beam into a medium comprising one or more precursors, to generate the 3D object comprising a material formed from the one or more precursors, wherein the at least one energy beam is directed into the medium as a 3D projection corresponding to the 3D object.

In another aspect, methods for printing a three-dimensional (3D) biological material, may comprise directing at least one energy beam to: 1) a first medium comprising a first plurality of cells and a first polymeric precursor, and 2) a second medium comprising a second plurality of cells and a second polymeric precursor, to generate a first portion of the 3D biological material and a second portion of the 3D biological material.

In another aspect, the present disclosure provides methods of producing a population of human immunological proteins, comprising: (a) providing a medium comprising (i) a plurality of cells and (ii) one or more polymer precursors; (b) depositing at least one layer of the medium onto a substrate; (c) subjecting the at least one layer of the medium to an energy source to form at least a portion of the 3D lymphoid organoid comprising (i) at least a subset of the plurality of cells, and (ii) a biogel formed from the one or more polymer precursors; and (d) subjecting the at least the portion of the 3D lymphoid organoid to conditions sufficient to stimulate production of the one or more immunological proteins.

Referring to FIG. 1, an embodiment of a system 100 for rapid multi-photon printing of a desired tissue is illustrated. Here, the system 100 comprises a laser printing system 110 driven by a solid-model computer-aided design (CAD) modeling system 112. In this embodiment, the CAD modeling system 112 comprises a computer 114 which controls the laser printing system 110 based on a CAD model of the desired tissue and additional parameters. The laser printing system 110 comprises a laser system 116 in communication with a multi-photon tissue printing print-head 118 which projects waveforms of a multi-photon laser beam 120 into a media chamber 122 to match the desired structure in complete or in specific parts. The multi-photon tissue print-head 118 includes at least one objective lens 124 that delivers the multi-photon laser beam 120 in the lateral and axial planes of the media chamber 122 to provide a two-dimensional and/or three dimensional and thus holographic projection of the CAD modeled tissue within the media chamber 122. The objective lens 124 may be a water-immersion objective lens, an air objective lens, or an oil-immersion objective lens. Two dimensional and three dimensional holographic projections may be generated simultaneously and projected into different regions by lens control. The media chamber 122 contains media comprised of cells, polymerizable material, and culture medium. The polymerizable material may comprise polymerizable monomeric units that are biologically compatible, dissolvable, and, in some cases, biologically inert. The monomeric units (or subunits) may polymerize, cross-link, or react in response to the multi-photon laser beam 120 to create cell containing structures, such as cell matrices and basement membrane structures, specific to the tissue to be generated. The monomeric units may polymerize and/or cross-link to form a matrix. In some cases, the polymerizable monomeric units may comprise mixtures of collagen with other extracellular matrix components including but not limited to elastin and hyaluronic acid to varying percentages depending on the desired tissue matrix.

Non-limiting examples of extracellular matrix components used to create cell containing structures may include proteoglycans such as heparan sulfate, chondroitin sulfate, and keratan sulfate, non-proteoglycan polysaccharide such as hyaluronic acid, collagen, and elastin, fibronectin, laminin, nidogen, or any combination thereof. These extracellular matrix components may be functionalized with acrylate, diacrylate, methacrylate, cinnamoyl, coumarin, thymine, or other side-group or chemically reactive moiety to facilitate cross-linking induced directly by multi-photon excitation or by multi-photon excitation of one or more chemical doping agents. In some cases, photopolymerizable macromers and/or photopolymerizable monomers may be used in conjunction with the extracellular matrix components to create cell-containing structures. Non-limiting examples of photopolymerizable macromers may include polyethylene glycol (PEG) acrylate derivatives, PEG methacrylate derivatives, and polyvinyl alcohol (PVA) derivatives. In some instances, collagen used to create cell containing structure may be fibrillar collagen such as type I, II, III, V, and XI collagen, facit collagen such as type IX, XII, and XIV collagen, short chain collagen such as type VIII and X collagen, basement membrane collagen such as type IV collagen, type VI collagen, type VII collagen, type XIII collagen, or any combination thereof.

Specific mixtures of monomeric units may be created to alter the final properties of the polymerized biogel. This base print mixture may contain other polymerizable monomers that are synthesized and not native to mammalian tissues, comprising a hybrid of biologic and synthetic materials. An example mixture may comprise about 0.4% w/v collagen methacrylate plus the addition of about 50% w/v polyethylene glycol diacrylate (PEGDA). Photoinitiators to induce polymerization may be reactive in the ultraviolet (UV), infrared (IR), or visible light range.

Examples of two such photo initiators are Eosin Y (EY) and triethanolamine (TEA), that when combined may polymerize in response to exposure to visible light (e.g., wavelengths of about 390 to 700 nanometers). Non-limiting examples of photoinitiators may include azobisisobutyronitrile (AIBN), benzoin derivatives, benziketals, hydroxyalkylphenones, acetophenone derivatives, trimethylolpropane triacrylate (TPT), acryloyl chloride, benzoyl peroxide, camphorquinone, benzophenone, thioxanthones, and 2-hydroxy-1-[4-(hydroxyethoxy)phenyl]-2-methyl-1-propanone. Hydroxyalkylphenones may include 4-(2-hydroxyethylethoxy)-phenyl-(2-hydroxy-2-methyl propyl) ketone (Irgacure® 295), 1-hidroxycyclohexyl-1-phenyl ketone (Irgacure® 184) and 2,2-dimethoxy-2-phenylacetophenone (Irgacure® 651). Acetophenone derivatives may include 2,2-dimethoxy-2-phenylacetophenone (DMPA). Thioxanthones may include isopropyl thioxanthone.

Specific mixtures of monomeric units of biological materials may be created to alter the final properties of the polymerized biogel, an example mixture may include about 1 mg/mL type I collagen-methacrylate, about 0.5 mg/mL type III collagen, about 0.2 mg/mL methacrylated hyaluronic acid, about 0.1% Eosin Y, and about 0.1% triethanolamine.

In some cases, the polymerized biogel may comprise at least about 0.01% of a photoinitiator. In some cases, the polymerized biogel may comprise about 10% of a photoinitiator or more. In some cases, the polymerized biogel comprises about 0.1% of a photoinitiator. In some cases, the polymerized biogel may comprise about 0.01% to about 0.05%, about 0.01% to about 0.1%, about 0.01% to about 0.2%, about 0.01% to about 0.3%, about 0.01% to about 0.4%, about 0.01% to about 0.5%, about 0.01% to about 0.6%, about 0.7% to about 0.8%, about 0.9% to about 1%, about 0.01% to about 2%, about 0.01% to about 3%, about 0.01%% to about 4%, about 0.01% to about 5%, about 0.01% to about 6%, about 0.01% to about 7%, about 0.01% to about 8%, about 0.01% to about 9%, or about 0.01% to about 10% of a photoinitiator.

The polymerized biogel may comprise about 0.05% of a photoinitiator. The polymerized biogel may comprise 0.1% of a photoinitiator. The polymerized biogel may comprise about 0.2% of a photoinitiator. The polymerized biogel may comprise about 0.3% of a photoinitiator. The polymerized biogel may comprise about 0.4% of a photoinitiator. The polymerized biogel may comprise about 0.5% of a photoinitiator. The polymerized biogel may comprise about 0.6% of a photoinitiator. The polymerized biogel may comprise about 0.7% of a photoinitiator. The polymerized biogel may comprise about 0.8% of a photoinitiator. The polymerized biogel may comprise about 0.9% of a photoinitiator. The polymerized biogel may comprise about 1% of a photoinitiator. The polymerized biogel may comprise about 1.1% of a photoinitiator. The polymerized biogel may comprise about 1.2% of a photoinitiator. The polymerized biogel may comprise about 1.3% of a photoinitiator. The polymerized biogel may comprise about 1.4% of a photoinitiator. The polymerized biogel may comprise about 1.5% of a photoinitiator. The polymerized biogel may comprise about 1.6% of a photoinitiator. The polymerized biogel may comprise about 1.7% of a photoinitiator. The polymerized biogel may comprise about 1.8% of a photoinitiator. The polymerized biogel may comprise about 1.9% of a photoinitiator. The polymerized biogel may comprise about 2% of a photoinitiator. The polymerized biogel may comprise about 2.5% of a photoinitiator. The polymerized biogel may comprise about 3% of a photoinitiator. The polymerized biogel may comprise about 3.5% of a photoinitiator. The polymerized biogel may comprise about 4% of a photoinitiator. The polymerized biogel may comprise about 4.5% of a photoinitiator. The polymerized biogel may comprise about 5% of a photoinitiator. The polymerized biogel may comprise about 5.5% of a photoinitiator. The polymerized biogel may comprise about 6% of a photoinitiator. The polymerized biogel may comprise about 6.5% of a photoinitiator. The polymerized biogel may comprise about 7% of a photoinitiator. The polymerized biogel may comprise about 7.5% of a photoinitiator. The polymerized biogel may comprise about 8% of a photoinitiator. The polymerized biogel may comprise about 8.5% of a photoinitiator. The polymerized biogel may comprise about 9% of a photoinitiator. The polymerized biogel may comprise about 9.5% of a photoinitiator. The polymerized biogel may comprise about 10% of a photoinitiator.

In some cases, the polymerized biogel may comprise at least about 10% of a photopolymerizable macromer and/or photopolymerizable monomer. In some cases, the polymerized biogel may comprise about 99% or more of a photopolymerizable macromer and/or photopolymerizable monomer. In some cases, the polymerized biogel may comprise about 50% of a photopolymerizable macromer and/or photopolymerizable monomer. In some cases, the polymerized biogel may comprise about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 10% to about 80%, about 10% to about 85%, about 10% to about 90%, about 10% to about 95%, or about 10% to about 99% of a photopolymerizable macromer and/or photopolymerizable monomer.

The polymerized biogel may comprise about 10% of a photopolymerizable macromer and/or photopolymerizable monomer. The polymerized biogel may comprise about 15% of a photopolymerizable macromer and/or photopolymerizable monomer. The polymerized biogel may comprise about 20% of a photopolymerizable macromer and/or photopolymerizable monomer. The polymerized biogel may comprise about 25% of a photopolymerizable macromer and/or photopolymerizable monomer. The polymerized biogel may comprise about 30% of a photopolymerizable macromer and/or photopolymerizable monomer. The polymerized biogel may comprise about 35% of a photopolymerizable macromer and/or photopolymerizable monomer. The polymerized biogel may comprise about 40% photopolymerizable macromer and/or photopolymerizable monomer. The polymerized biogel may comprise about 45% of a photopolymerizable macromer and/or photopolymerizable monomer. The polymerized biogel may comprise about 50% of a photopolymerizable macromer and/or photopolymerizable monomer. The polymerized biogel may comprise about 55% of a photopolymerizable macromer and/or photopolymerizable monomer. The polymerized biogel may comprise about 60% of a photopolymerizable macromer and/or photopolymerizable monomer. The polymerized biogel may comprise about 65% of a photopolymerizable macromer and/or photopolymerizable monomer. The polymerized biogel may comprise about 70% of a photopolymerizable macromer and/or photopolymerizable monomer. The polymerized biogel may comprise about 75% of a photopolymerizable macromer and/or photopolymerizable monomer. The polymerized biogel may comprise about 80% of a photopolymerizable macromer and/or photopolymerizable monomer. The polymerized biogel may comprise about 85% of a photopolymerizable macromer and/or photopolymerizable monomer. The polymerized biogel may comprise about 90% of a photopolymerizable macromer and/or photopolymerizable monomer. The polymerized biogel may comprise about 95% of a photopolymerizable macromer and/or photopolymerizable monomer. The polymerized biogel may comprise about 96% of a photopolymerizable macromer and/or photopolymerizable monomer. The polymerized biogel may comprise about 97% of a photopolymerizable macromer and/or photopolymerizable monomer. The polymerized biogel may comprise about 98% of a photopolymerizable macromer and/or photopolymerizable monomer. The polymerized biogel may comprise about 99% of a photopolymerizable macromer and/or photopolymerizable monomer.

Two-photon absorption is non-linear and cannot be accurately predicted or calculated based on single photon absorption properties of a chemical. A photo-reactive chemical may have a peak, two-photon absorption at or around double the single photon absorption or be slightly-redshifted in absorption spectra. Therefore, wavelengths at or about 900 nanometers through about 1400 nanometers may be used for polymerization of monomeric materials by exciting mixtures of catalysts of the polymerization reaction, for example EY or TEA. Single wavelength polymerization may be sufficient for creating all structural elements, however to further speed up the printing process, multiple wavelengths may be employed simultaneously through the same printing apparatus and into the same printing chamber.

Premixing or pre-reacting of polymerizable monomeric units with catalysts comprising differing absorption bands may allow for printing at different wavelengths to form different substrate-based structural elements simultaneously within the media chamber 122. Thus, certain structural elements may be generated by tuning the excitation wavelength of the laser to a particular wavelength, and then other structural elements may be generated around the existing elements by tuning another or the same laser to a different excitation wavelength that may interact with a distinct photoinitiator that initiates polymerization of one material base with greater efficiency. Likewise, different wavelengths may be used for different structural elements, wherein increased rigidity is desired in some locations and soft or elastic structures are desired in other locations. Because of the different physical properties of polymerizable materials this may allow for potentially more rigid, soft, or elastic structures to be created in the same print step with the same cells by simply tuning the excitation wavelength of the laser electronically, by switching between different lasers, or by simultaneously projecting two different wavelengths.

Figure 2A:
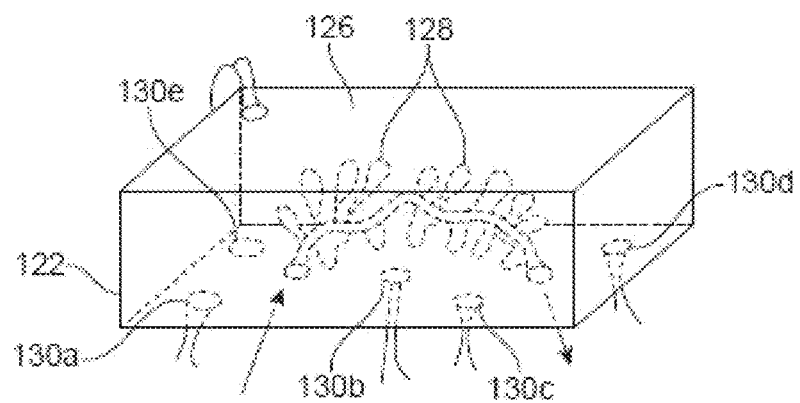
FIGS. 2A-2D illustrate example stages of the generation of a desired tissue within the media chamber.
Figure 2B:
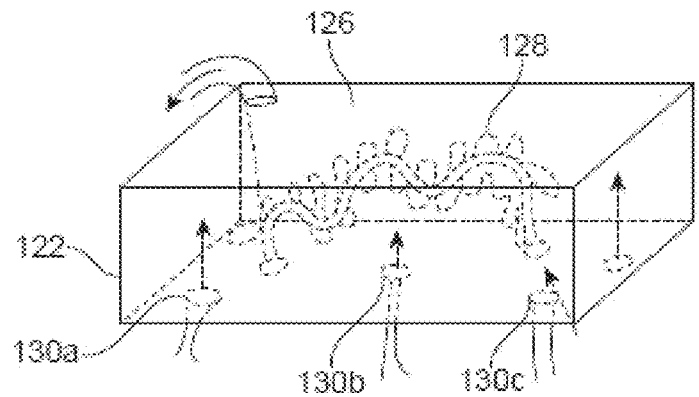
Figure 2C:
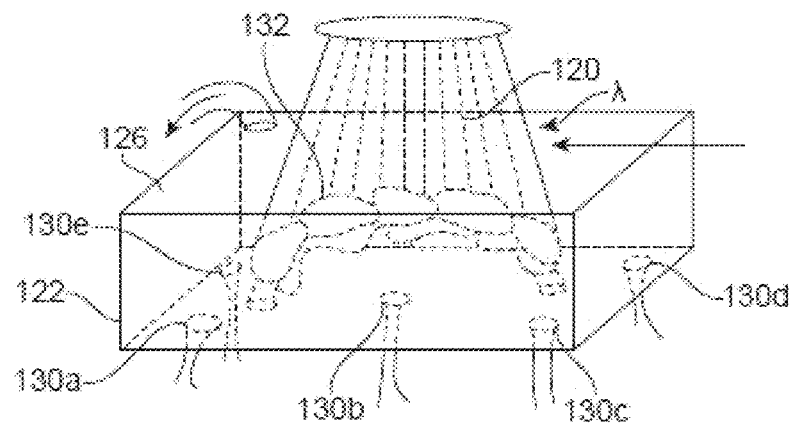

FIGS. 2A-2C illustrate example stages of the generation of a desired tissue within the media chamber 122. FIG. 2A illustrates the media chamber 122 containing media 126 comprised of a first cell group, polymerizable material and culture medium. In this embodiment, pulses of the multiphoton laser beam 120 may be delivered to the media 126 according to the CAD model corresponding to the vascular structure and microvasculature of the desired tissue. In some instances, the first cell group may comprise vascular and/or microvascular cells including but not limited to endothelial cells, microvascular endothelial cells, pericytes, smooth muscle cells, fibroblasts, endothelial progenitor cells, stem cells, or any combination thereof. Thus, portions of the media 126 may polymerize, cross-link or react to form cell-containing scaffolding 128 representing the vasculature and microvasculature of the desired tissue. In this embodiment, the media 126 may then be drained through a first port 130a, a second port 130b, a third port 130c, a fourth port 130d, and a fifth port 130e to remove the first cell group and associated media. In some instances, the media chamber 122 may comprise at least one port. In some instances, the media chamber 122 may comprise a plurality of ports ranging from at least one port to 100 ports at most. The media chamber 122 may comprise at least two ports. The media chamber 122 may comprise at least three ports. The media chamber 122 may comprise at least four ports. The media chamber 122 may comprise at least five ports.

Referring to FIG. 2B, the media chamber 122 may be filled with media 126 containing a second cell group, polymerizable material and culture medium through ports 130. This second cell group may be used to generate tissue structures around the existing cell-containing scaffolding 128. In some instances, the cell-containing scaffolding 128 may be a vascular scaffold. The printed vascular scaffolding may comprise endothelial cells, vascular endothelial cells, pericytes, smooth muscle cells, fibroblasts, endothelial progenitor cells, stem cells, or any combination thereof.

The first cell group and/or second cell group may comprise endothelial cells, microvascular endothelial cells, pericytes, smooth muscle cells, fibroblasts, endothelial progenitor cells, lymph cells, T cells such as helper T cells and cytotoxic T cells, B cells, natural killer (NK) cells, reticular cells, hepatocytes, or any combination thereof. The first cell group and/or second cell group may comprise exocrine secretory epithelial cells, hormone-secreting cells, epithelial cells, nerve cells, adipocytes, kidney cells, pancreatic cells, pulmonary cells, extracellular matrix cells, muscle cells, blood cells, immune cells, germ cells, interstitial cells, or any combination thereof.

The first cell group and/or second cell group may comprise exocrine secretory epithelial cells including but not limited to salivary gland mucous cells, mammary gland cells, sweat gland cells such as eccrine sweat gland cell and apocrine sweat gland cell, sebaceous gland cells, type II pneumocytes, or any combination thereof.

The first cell group and/or second cell group may comprise hormone-secreting cells including but not limited to anterior pituitary cells, intermediate pituitary cells, magnocellular neurosecretory cells, gut tract cells, respiratory tract cells, thyroid gland cells, parathyroid gland cells, adrenal gland cells, Leydig cells, theca interna cells, corpus luteum cells, juxtaglomerular cells, macula densa cells, peripolar cells, mesangial cells, pancreatic islet cells such as alpha cells, beta cells, delta cells, PP cells, and epsilon cells, or any combination thereof.

The first cell group and/or second cell group may comprise epithelial cells including but not limited to keratinizing epithelial cells such as keratinocytes, basal cells, and hair shaft cells, stratified barrier epithelial cells such as surface epithelial cells of stratified squamous epithelium, basal cells of epithelia, and urinary epithelium cells, or any combination thereof.

The first cell group and/or second cell group may comprise nerve cells or neurons including but not limited to sensory transducer cells, autonomic neuron cells, peripheral neuron supporting cells, central nervous system neurons such as interneurons, spindle neurons, pyramidal cells, stellate cells, astrocytes, oligodendrocytes, ependymal cells, glial cells, or any combination thereof.

The first cell group and/or second cell group may comprise kidney cells including but not limited to, parietal cells, podocytes, mesangial cells, distal tubule cells, proximal tubule cells, Loop of Henle thin segment cells, collecting duct cells, interstitial kidney cells, or any combination thereof.

The first cell group and/or second cell group may comprise pulmonary cells including, but not limited to type I pneumocyte, alveolar cells, capillary endothelial cells, alveolar macrophages, bronchial epithelial cells, bronchial smooth muscle cells, tracheal epithelial cells, small airway epithelial cells, or any combination thereof.

The first cell group and/or second cell group may comprise extracellular matrix cells including, but not limited to epithelial cells, fibroblasts, pericytes, chondrocytes, osteoblasts, osteocytes, osteoprogenitor cells, stellate cells, hepatic stellate cells, or any combination thereof.

The first cell group and/or second cell group may comprise muscle cells including, but not limited to skeletal muscle cells, cardiomyocytes, Purkinje fiber cells, smooth muscle cells, myoepithelial cells, or any combination thereof.

The first cell group and/or second cell group may comprise blood cells and/or immune cells including, but not limited to erythrocytes, megakaryocytes, monocytes, macrophages, osteoclasts, dendritic cells, microglial cells, neutrophils, eosinophils, basophils, mast cells, helper T cells, suppressor T cells, cytotoxic T cells, natural killer T cells, B cells, natural killer (NK) cells, reticulocytes, or any combination thereof.

FIG. 2C illustrates delivery of pulses of the multi-photon laser beam 120 to the media 126 according to the CAD model of the remaining tissue. Thus, additional portions of the media 126 may polymerize, cross-link or react to form cell-containing structures 132 around the existing cell-containing scaffolding 128 (no longer visible) without damaging or impacting the existing vascular scaffolding 128. The steps of draining the media 126, refilling with new media 126 and delivering laser energy may be repeated any number of times to create the desired complex tissue.

Figure 2D:
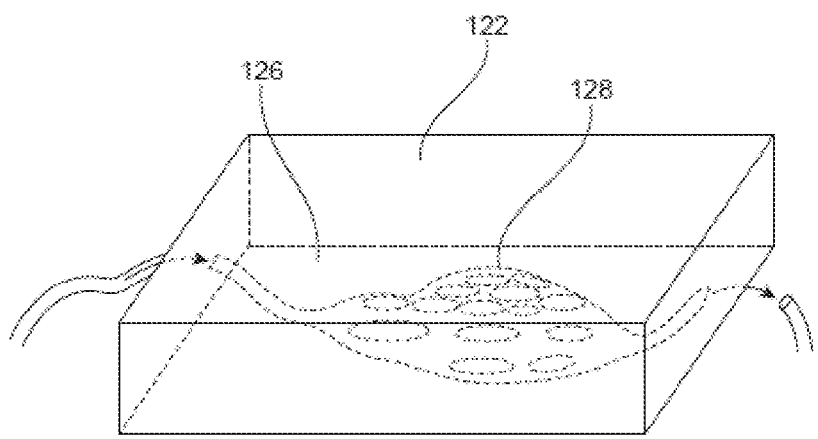

FIG. 2D illustrates an embodiment wherein the cell-containing scaffolding 128 may be printed along the bottom of the media chamber 122 containing media 126. Thus, the scaffolding 128 may not be free standing or free floating. The multi-channel input may reduce shear forces associated with bulk flow from one direction, uneven washing of fine structures as bulk flow may not wash unwanted cells from small features, and uneven distribution of new cell containing media as it is cycled into the tissue printing chamber. The multiple inputs may come from the top, bottom, sides or all three simultaneously. Multiple inputs are particularly desired for tissue printing because cell-containing structures are relatively fragile and potentially disrupted by the application of fluid forces associated with media exchange through the chamber. FIG. 2D shows that the tissues may be printed above the bottom plate of the media chamber. In some embodiments, the cells and tissue may be printed flush against the bottom of the media chamber. Additionally, this design may allow for easy transport of printed tissues and positioning under a laser print head (focusing objective) and is a closed system that may allow for media exchange and printing to occur without exposure to room air. This may be desired as exposure to room air may introduce infectious agents into the cell culture media which may disrupt or completely destroy the development of useful tissues.

Laser Printing Systems

In an aspect, the present disclosure provides systems for printing a three-dimensional (3D) biological material. The x, y, and z dimensions may be simultaneously accessed by the systems provided herein. A system for printing a 3D biological material may comprise a media chamber configured to contain a medium comprising a plurality of cells comprising cells and one or more polymer precursors. The plurality of cells may comprise cells of at least one type. The plurality of cells may comprise cells of at least two different types. The system may comprise at least one energy source configured to direct at least one energy beam to the media chamber. The system may comprise at least one energy source configured to direct at least one energy beam to the media chamber and/or to the cell-containing chamber. The system may comprise one or more computer processors operatively coupled to the at least one energy source, wherein the one or more computer processors may be individually or collectively programmed to: receive computer instructions for printing the 3D biological material from computer memory; and direct the at least one energy source to direct the at least one energy beam to the medium in the media chamber along at least one energy beam path in accordance with the computer instructions, to subject at least a portion of the polymer precursors to form at least a portion of the 3D biological material.

In another aspect, the present disclosure provides an additional system for printing a 3D biological material, comprising a media chamber configured to contain a medium comprising a plurality of cells and a plurality of polymer precursors. The system may comprise at least one energy source configured to direct at least one energy beam to the media chamber. In addition, the system may comprise one or more computer processors that may be operatively coupled to the at least one energy source. The one or more computer processors may be individually or collectively programmed to: (i) receive computer instructions for printing the 3D biological material from computer memory; (ii) direct the at least one energy source to direct the at least one energy beam to the medium in the media chamber along at least one energy beam path in accordance with the computer instructions, to subject at least a portion of the polymer precursors to form at least a portion of the 3D biological material; and (iii) direct the at least one energy source to direct the at least one energy beam to a second medium in the media chamber along at least one energy beam path in accordance with the computer instructions, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

The one or more computer processors are individually or collectively programmed to generate a point-cloud representation or lines-based representation of the 3D biological material in computer memory, and use the point-cloud representation or lines-based representation to generate the computer instructions for printing the 3D biological material in computer memory. The one or more computer processors may be individually or collectively programmed to direct the at least one energy source to direct the at least one energy beam along one or more additional energy beam paths to form at least another portion of the 3D biological material.

The system may comprise one or more computer processors operatively coupled to at least one energy source and/or to at least one light patterning element. The point-cloud representation or the lines-based representation of the computer model may be a holographic point-cloud representation or a holographic lines-based representation. The one or more computer processors may be individually or collectively programmed to use the light patterning element to re-project the holographic image as illuminated by the at least one energy source.

In some cases, one or more computer processors may be individually or collectively programmed to convert the point-cloud representation or lines-based representation into an image. The one or more computer processors may be individually or collectively programmed to project the image in a holographic manner. The one or more computer processors may be individually or collectively programmed to project the image as a hologram. The one or more computer processors may be individually or collectively programmed to project the image as partial hologram. In some cases, one or more computer processors may be individually or collectively programmed to convert the point-cloud representation or lines-based representation of a complete image set into a series of holographic images via an algorithmic transformation. This transformed image set may then be projected in sequence by a light patterning element, such as a spatial light modulator (SLM) or digital mirror device (DMD), through the system, recreating the projected image within the printing chamber with the projected light that is distributed in 2D and or 3D simultaneously. An expanded or widened laser beam may be projected onto the SLMs and/or DMDs, which serve as projection systems for the holographic image. In some cases, one or more computer processors may be individually or collectively programmed to project the image in a holographic manner. In some cases, one or more computer processors may be individually or collectively programmed to project the images all at once or played in series as a video to form a larger 3D structure in a holographic manner.

Holography is a technique that projects a multi-dimensional (e.g. 2D and/or 3D) holographic image or a hologram. When a laser that can photo-polymerize a medium is projected as a hologram, the laser may photopolymerize, solidify, cross-link, bond, harden, and/or change a physical property of the medium along the projected laser light path; thus, the laser may allow for the printing of 3D structures. Holography may require a light source, such as a laser light or coherent light source, to create the holographic image. The holographic image may be constant over time or varied with time (e.g., a holographic video). Furthermore, holography may require a shutter to open or move the laser light path, a beam splitter to split the laser light into separate paths, mirrors to direct the laser light paths, a diverging lens to expand the beam, and additional patterning or light directing elements.

A holographic image of an object may be created by expanding the laser beam with a diverging lens and directing the expanded laser beam onto the hologram and/or onto at least one pattern forming element, such as, for example a spatial light modulator or SLM. The pattern forming element may encode a pattern comprising the holographic image into a laser beam path. The pattern forming element may encode a pattern comprising a partial hologram into a laser beam path. Next, the pattern may be directed towards and focused in the medium chamber containing the printing materials (i.e., the medium comprising the plurality of cells and polymeric precursors), where it may excite a light-reactive photoinitiator found in the printing materials (i.e., in the medium). Next, the excitation of the light-reactive photoinitiator may lead to the photopolymerization of the polymeric-based printing materials and forms a structure in the desired pattern (i.e., holographic image). In some cases, one or more computer processors may be individually or collectively programmed to project the holographic image by directing an energy source along distinct energy beam paths.

In some cases, at least one energy source may be a plurality of energy sources. The plurality of energy sources may direct a plurality of the at least one energy beam. The energy source may be a laser. In some examples, the laser may be a fiber laser. For example, a fiber laser may be a laser with an active gain medium that includes an optical fiber doped with rare-earth elements, such as, for example, erbium, ytterbium, neodymium, dysprosium, praseodymium, thulium and/or holmium. The energy source may be a short-pulsed laser. The energy source may be a femtosecond pulsed laser. The femtosecond pulsed laser may have a pulse width less than or equal to about 500 femtoseconds (fs), 250, 240, 230, 220, 210, 200, 150, 100, 50 fs, 40 fs, 30 fs, 20 fs, 10 fs, 9 fs, 8 fs, 7 fs, 6 fs, 5 fs, 4 fs, 3 fs, 2 fs, 1 fs, or less. The femtosecond pulsed laser may be, for example, a titanium:sapphire (Ti:Sa) laser. The at least one energy source may be derived from a coherent light source.

The coherent light source may provide light with a wavelength from about 300 nanometers (nm) to about 5 millimeters (mm). The coherent light source may comprise a wavelength from about 350 nm to about 1800 nm, or about 1800 nm to about 5 mm. The coherent light source may provide light with a wavelength of at least about 300 nm, 400 nm, 500 nm, 600 nm, 700 nm, 800 nm, 900 nm, 1 mm, 1.1 mm, 1.2, mm, 1.3 mm, 1.4 mm, 1.5 mm, 1.6 mm, 1.7 mm, 1.8 mm, 1.9 mm, 2 mm, 3 mm, 4 mm, 5 mm, or greater.

The computer processors may be individually or collectively programmed to direct the at least one energy source to direct the at least one energy beam along one or more additional energy beam paths to form at least another portion of the 3D biological material. The one or more additional energy beam paths may be along an x axis, an x and y plane, or the x, y, and z planes. The one or more additional energy beam paths may be along an x axis. The one or more additional energy beam paths may be along a y axis. The one or more additional energy beam paths may be along a z axis. The energy beam path may converge with one or more other beams on the same axis. The one or more additional energy beam paths may be in the x and y plane. The one or more additional energy beam paths may be in the x and z plane. The one or more additional energy beam paths may be in the y and z plane. The one or more additional energy beam paths may be in the x, y, and z planes.

The system may further comprise at least one objective lens for directing the at least one energy beam to the medium in the media chamber. In some instances, at least one objective lens may comprise a water-immersion objective lens. In some instances, at least one objective lens may comprise a water-immersion objective lens. In some instances, at least one objective lens may comprise a water dipping objective lens. In some instances, at least one objective lens may comprise an oil immersion objective lens. In some instances, at least one objective lens may comprise an achromatic objective lens, a semi-apochromatic objective lens, a plans objective lens, an immersion objective lens, a Huygens objective lens, a Ramsden objective lens, a periplan objective lens, a compensation objective lens, a wide-field objective lens, a super-field objective lens, a condenser objective lens, or any combination thereof. Non-limiting examples of a condenser objective lens may include an Abbe condenser, an achromatic condenser, and a universal condenser.

The one or more computer processors may be individually or collectively programmed to receive images of the edges of the 3D biological material. The one or more computer processors may be individually or collectively programmed to receive images of the exterior surfaces of the 3D biological material. The one or more computer processors may be individually or collectively programmed to receive images of the interior surfaces of the 3D biological material. The one or more computer processors may be individually or collectively programmed to receive images of the interior of the 3D biological material.

The one or more computer processors may be individually or collectively programmed to direct linking of the 3D biological material with other tissue, which linking may be in accordance with the computer instructions. The one or more computer processors may be individually or collectively programmed to directly link, merge, bond, or weld 3D printed material with already printed structures, where linking is in accordance with the computer model. In some cases, linking of the 3D biological material with other tissue may involve chemical cross-linking, mechanical linking, and/or cohesively coupling.

In another aspect, the system may comprise a media chamber configured to contain a medium comprising a plurality of cells and a plurality of polymer precursors. The system may comprise at least one energy source configured to direct at least one energy beam to the media chamber. The system may comprise one or more computer processors operatively coupled to at least one energy source, wherein the one or more computer processors are individually or collectively programmed to: receive a computer model of the 3D biological material in computer memory; generate a point-cloud representation or lines-based representation of the computer model of the 3D biological material in computer memory; direct the at least one energy source to direct the at least one energy beam to the medium in the media chamber along at least one energy beam path in accordance with the computer model of the 3D biological material, to subject at least a portion of the polymer precursors to form at least a portion of the 3D biological material; and direct the at least one energy source to direct the at least one energy beam to a second medium in the media chamber along at least one energy beam path in accordance with the computer model of the 3D biological material, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

In laser printing of cellular structures, rapid three-dimensional structure generation using minimally toxic laser excitation is critical for maintaining cell viability and in the case of functional tissue printing, necessary for large-format, high resolution, multicellular tissue generation. Other methods of two-photon printing may rely upon raster-scanning of two-photon excitation in a two-dimensional plane (x, y) (e.g., selective laser sintering), while moving the microscope or stage in the z direction to create a three-dimensional structure. This technique may be prohibitively slow for large format multicellular tissue printing such that cell viability may be unlikely to be maintained during printing of complex structures. Certain hydrogels with high rates of polymerization may also be utilized for two-dimensional projection of tissue sheets that are timed such that one slice of a structure is projected with each step in in an x, y, or z plane. Additionally, mixed plane angles representing a sheet or comprising an orthogonal slice may also be utilized. In the case of rapidly polymerizing hydrogels, these projections may work in time-scales that are compatible with tissue printing whereas laser sintering or raster scanning (e.g. layer-by-layer deposition) may be prohibitively slow for building a complex structure.

The laser printing system 110 of the present disclosure may be equipped with an objective lens 124 that may allow for focusing of the three-dimensional or two-dimensional holographic projection in the lateral and axial planes for rapid creation of cell containing structures. The objective lens 124 may be a water-immersion objective lens, an air objective lens, or an oil-immersion objective lens. In some cases, the laser printing system 110 may include a laser system 116 having multiple laser lines and may be capable of three-dimensional holographic projection of images for photolithography via holographic projection into cell containing media.

Figure 3A:
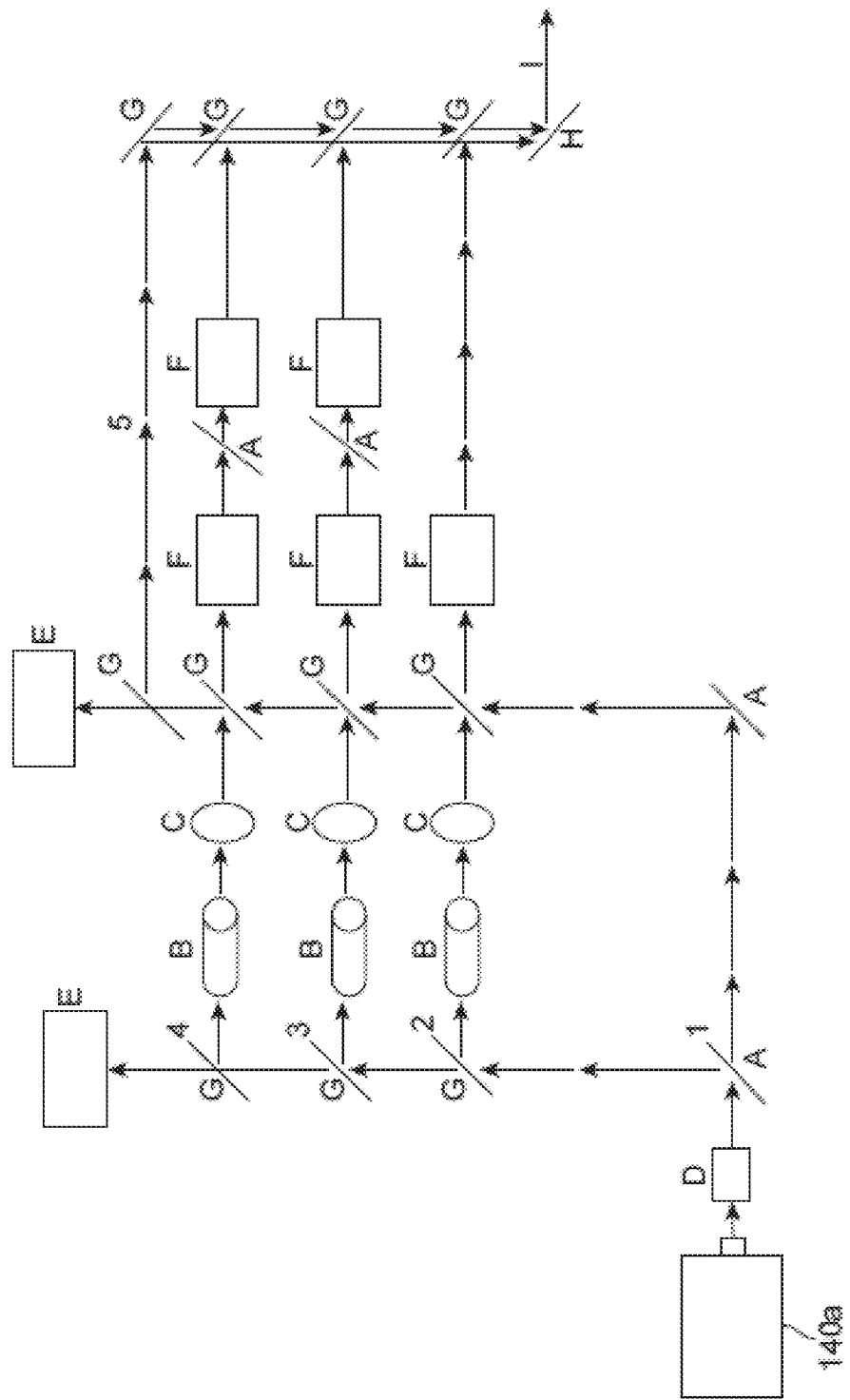
FIGS. 3A-3C illustrate various embodiments of a laser system.

FIG. 3A illustrates an embodiment of a laser system 116 having a first multi-photon laser source 140a. Here, the laser line one, multi-photon laser beam may be reflected by a spatial light modulator (SLM) with a video rate or faster re-fresh rate for image projection, to allow for rapid changes in the three-dimensional structure being projected.

In some cases, spatial light modulators (SLMs) may be used to print a 3D biological material. In some cases, the method presented herein may comprise receiving a computer model of the 3D biological material in computer memory and further processing the computer model such that the computer model is "sliced" into layers, creating a two-dimensional (2D) image of each layer. The computer model may be a computer-aided design (CAD) model. The system disclosed herein may comprise at least one computer processor which may be individually or collectively programmed to calculate a laser scan path based on the "sliced" computer model, which determines the boundary contours and/or fill sequences of the 3D biological material to be printed. Holographic 3D printing may be used with one or more polymer precursors described herein. SLM may be used with two or more polymer precursors described herein.

A spatial light modulator (SLM) is an electrically programmable device that can modulate amplitude, phase, polarization, propagation direction, intensity or any combination thereof of light waves in space and time according to a fixed spatial (i.e., pixel) pattern. The SLM may be based on translucent, e.g. liquid crystal display (LCD) microdisplays. The SLM may be based on reflective, e.g. liquid crystal on silicon (LCOS) microdisplays. The SLM may be a microchannel spatial light modulator (MSLM), a parallel-aligned nematic liquid crystal spatial light modulator (PAL-SLM), a programmable phase modulator (PPM), a phase spatial light modulator (LCOS-SLM), or any combination thereof. An LCOS-SLM may comprise a chip that includes a liquid crystal layer arranged on top of a silicon substrate. A circuit may be built on the chip's silicon substrate by using semiconductor technology. A top layer of the LCOS-SLM chip may contain aluminum electrodes that are able to control their voltage potential independently. A glass substrate may be placed on the silicon substrate while keeping a constant gap, which is filled by the liquid crystal material. The liquid crystal molecules may be aligned in parallel by the alignment control technology provided in the silicon and glass substrates. The electric field across this liquid crystal layer can be controlled pixel by pixel. The phase of light can be modulated by controlling the electric field; a change in the electric field may cause the liquid crystal molecules to tilt accordingly. When the liquid crystal molecules tilt, the liquid crystal refractive indexes may change further changing the optical path length and thus, causing a phase difference.

An SLM may be used to print the 3D biological material. A liquid crystal on silicon (LCOS)-SLM may be used to print the 3D biological material. A liquid crystal SLM may be used to print the 3D biological material. The SLM may be used to project a point-cloud representation or a lines-based representation of a computer model of the 3D biological material. The methods disclosed herein may comprise converting the point-cloud representation or lines-based representation into a holographic image. The SLM may be used to project the holographic image of the computer model of the 3D biological material. The SLM may be used to modulate the phase of light of a point-cloud representation or a lines-based representation of a computer model of the 3D biological material. The SLM may be used to modulate the phase of light of the holographic image of the computer model of the 3D biological material.

Projection of multi-photon excitation in three dimensions may also be achieved with the use of a dual digital micromirror device (DMD) system alone or in combination with a spatial light modulator (SLM). A pair of DMDs may be used with a pair of SLMs to print a 3D material using the methods described herein. At least one SLM and at least one DMD may be used to print a 3D material using the methods described herein. A pair of SLMs may be used to print a 3D material using the methods described herein. A pair of DMDs may be used to print a 3D material using the methods described herein. At least one SLM may be used to print a 3D material using the methods described herein. At least one DMD may be used to print a 3D material using the methods described herein. A DMD is an electrical input, optical output micro-electrical-mechanical system (MEMS) that allows for high speed, efficient, and reliable spatial light modulation. A DMD may comprise a plurality of microscopic mirrors (usually in the order of hundreds of thousands or millions) arranged in a rectangular array. Each microscopic mirror in a DMD may correspond to a pixel of the image to be displayed and can be rotated about e.g. 10-12° to an "on" or "off" state. In the "on" state, light from a projector bulb can be reflected into the microscopic mirror making its corresponding pixel appear bright on a screen. In the "off" state, the light can be directed elsewhere (usually onto a heatsink), making the microscopic mirror's corresponding pixel appear dark. The microscopic mirrors in a DMD may be composed of highly reflective aluminum and their length across is approximately 16 micrometers ($\mu m$). Each microscopic mirror may be built on top of an associated semiconductor memory cell and mounted onto a yoke which in turn is connected to a pair of support posts via torsion hinges. The degree of motion of each microscopic mirror may be controlled by loading each underlying semiconductor memory cell with a "1" or a "0." Next, a voltage is applied, which may cause each microscopic mirror to be electrostatically deflected about the torsion hinge to the associated +/−degree state via electrostatic attraction.

Figure 3B:
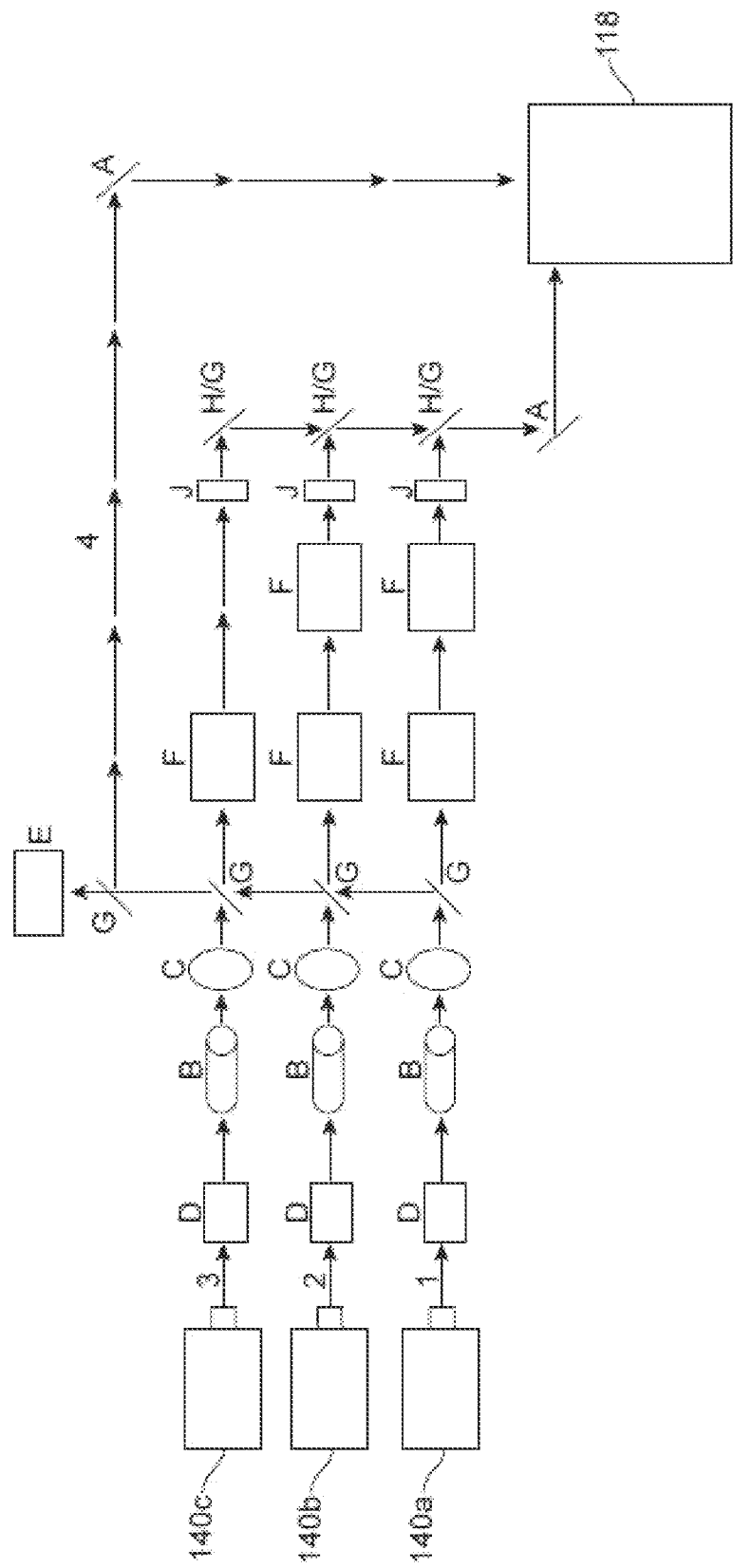
Figure 3C:
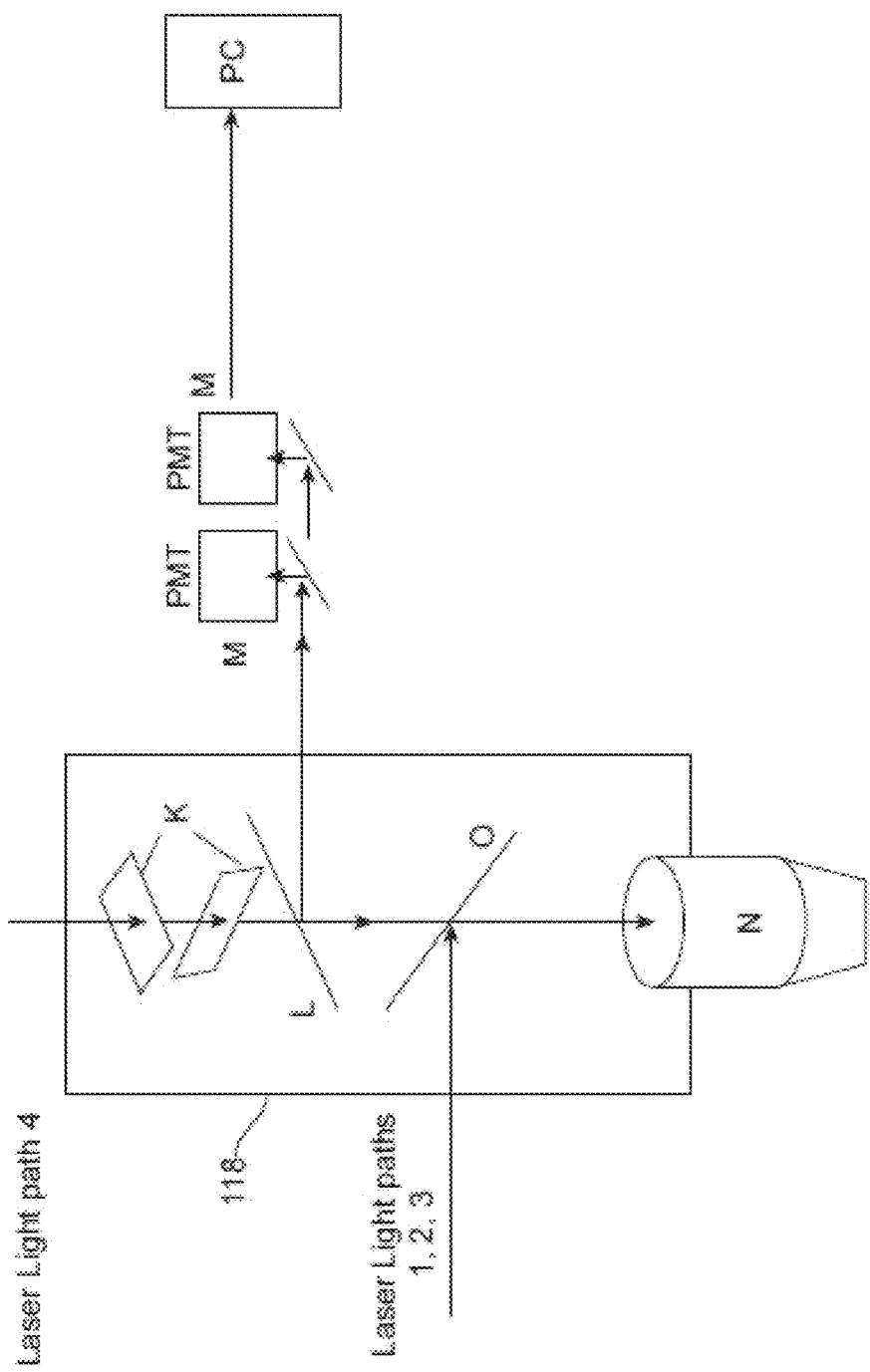

With reference to FIGS. 3A-3C, the addition of an optional beam expander followed by a Bessel beam generating lens that is either a fixed axicon or a tunable acoustic gradient (TAG) lens may be added to alter the properties of the laser to achieve higher resolution and greater tissue printing depth, particularly in turbid solutions. The laser line, which may include the optional beam expander and/or Bessel beam generating lens, is directed with fast switch mirrors to distinct projection systems that have material advantages in the formation of specific structures associated with tissue printing. In some cases, a high resolution DMD mirror in conjunction with an SLM system may achieve higher axial resolution than is capable with two SLM systems. Finally, a laser line may be used with a single DMD or SLM system in conjunction with a mirror to allow for scan-less projection of a two-dimensional image in any of the axial planes. A 3D projection pattern may also be raster-scanned across a larger field of view by scan mirrors where in laser emission patterns, wavelength, and or power is controlled to match the raster scan speed such that a cohesive and complex structure may be deposited. Within the system containing more than one laser line the configurations may be any combination of dual SLM, dual DMD, single SLM, single DMD or simple planar scanning.

In some cases, one or more light paths, such as the ones shown in FIGS. 3A-3C, may be used independently or in concert. The lenses, gratings, and mirrors that focus and distribute the light or energy beam within the optical path may be placed between the primary, wave-front shaping elements necessary to distribute the light through key elements or modulate incoming light in the case of a grating, as described in FIG. 3A. At least one grating or mirror may be placed between wave-front shaping elements "F" (i.e., between an SLM, a DMD, and/or a TAG lens) for the purpose of focusing, distributing, or clipping the input laser light. The optical wave-front shaping device F may comprise an SLM, an LCOS-SLM, a DMD, a TAG lens, or any combination thereof.

In some cases, a DMD may be used to print a 3D biological material. The DMD may be used to project a point-cloud representation or a lines-based representation of a computer model of the 3D biological material. The methods disclosed herein may comprise converting the point-cloud representation or lines-based representation into a holographic image. The DMD may be used to project the holographic image of the computer model of the 3D biological material. The DMD may be used to print the 3D biological material.

In some cases, a combination of at least one SLM and at least one DMD may be used in the methods disclosed herein to print the 3D biological material. The combination of at least one SLM and at least one DMD may be arranged in series. The combination of at least one SLM and at least one DMD may be arranged in parallel. The combination of any number of SLMs and any number of DMDs may be arranged in series when used to print the 3D biological material. The combination of any number of SLMs and any number of DMDs may be arranged in parallel when used to print the 3D biological material.

The combination of at least two SLMs and at least one DMD may be used to print the 3D biological material. The combination of at least three SLMs and at least one DMD may be used to print the 3D biological material. The combination of at least four SLMs and at least one DMD may be used to print the 3D biological material. The combination of at least five SLMs and at least one DMD may be used to print the 3D biological material. The combination of at least ten SLMs and at least one DMD may be used to print the 3D biological material. The combination of at least twenty SLMs and at least one DMD may be used to print the 3D biological material.

The combination of at least one SLM and at least two DMDs may be used to print the 3D biological material. The combination of at least one SLM and at least three DMDs may be used to print the 3D biological material. The combination of at least one SLM and at least four DMDs may be used to print the 3D biological material. The combination of at least one SLM and at least five DMDs may be used to print the 3D biological material. The combination of at least one SLM and at least ten DMDs may be used to print the 3D biological material. The combination of at least one SLM and at least twenty DMDs may be used to print the 3D biological material.

The combination of at least two SLMs and at least two DMDs may be used to print the 3D biological material. The combination of at least three SLMs and at least three DMDs may be used to print the 3D biological material. The combination of at least four SLMs and at least four DMDs may be used to print the 3D biological material. The combination of at least five SLMs and at least five DMDs may be used to print the 3D biological material. The combination of at least ten SLMs and at least ten DMDs may be used to print the 3D biological material. The combination of at least twenty SLMs and at least twenty DMDs may be used to print the 3D biological material.

A liquid crystal SLM may be used to print the 3D biological material. A plurality of SLMs may be used to print the 3D biological material. The plurality of SLMs can be arranged in series. The plurality of SLMs can be arranged in parallel. At least one or more SLMs may be used to print the 3D biological material. At least two or more SLMs may be used to print the 3D biological material. At least three or more SLMs may be used to print the 3D biological material. At least four or more SLMs may be used to print the 3D biological material. At least five or more SLMs may be used to print the 3D biological material. At least ten or more SLMs may be used to print the 3D biological material. At least twenty or more SLMs may be used to print the 3D biological material. At least one to about fifty or more SLMs may be used to print the 3D biological material. At least one to about twenty or more SLMs may be used to print the 3D biological material. At least one to about fifteen or more SLMs may be used to print the 3D biological material. At least one to about ten or more SLMs may be used to print the 3D biological material. At least one to about five or more SLMs may be used to print the 3D biological material.

A plurality of DMDs may be used to print the 3D biological material. The plurality of DMDs can be arranged in series. The plurality of DMDs can be arranged in parallel. At least one or more DMDs may be used to print the 3D biological material. At least two or more DMDs may be used to print the 3D biological material. At least three or more DMDs may be used to print the 3D biological material. At least four or more DMDs may be used to print the 3D biological material. At least five or more DMDs may be used to print the 3D biological material. At least ten or more DMDs may be used to print the 3D biological material. At least twenty or more DMDs may be used to print the 3D biological material. At least one to about fifty or more DMDs may be used to print the 3D biological material. At least one to about twenty or more DMDs may be used to print the 3D biological material. At least one to about fifteen or more DMDs may be used to print the 3D biological material. At least one to about ten or more DMDs may be used to print the 3D biological material. At least one to about five or more DMDs may be used to print the 3D biological material.

In this design, SLM may refer to liquid crystal SLM and the function of the DMD may be similar to the SLM. These lasers may be controlled by one or more computer inputs to address location and print timing of multiple laser lines. An example overall design for the light path, including optional in-series excitations paths is illustrated in FIG. 3A along with further description of the elements provided in Table 1. Because of the extensive pulse-width between packets of two photon excitation light, any combination of these laser lines, which may be non-interfering, may be used simultaneously for printing and printing with simultaneous imaging. This may permit the interference between the beams to be substantially low such that the beams to not intersect. Therefore, the use of multiple laser lines with minimal to no interference is possible as illustrated in FIGS. 3B-3C along with further description of the elements also provided in Table 1. The group delay dispersion optical element in this configuration may be used to disperse two-photon packets such that the peak power output does not damage a fiber optic cable if one is to be used in certain configurations. In addition, group delay dispersion can concentrate photons into shorter pulse-widths such that more energy is imparted at the focal point or in the projected image allowing for more rapid printing.

Two photon excitation pulses may be temporally controlled such that excitation at a single spot occurs with pulses that are femto- to nanosecond range in length (dependent on laser tuning) while the timing between these photon packets is three to six orders of magnitude longer than the pulse width. This may allow for minimal cross-path interference of laser excitations making use of multiple lasers for simultaneous printing possible when using multiple laser lines in series. An example of multiple laser projections at three different theoretical wavelengths for the purpose of structure deposition is presented in FIG. 3B. Multi-photon lasers are tunable; thus, they may allow for a range of wavelengths to be selected. This is advantageous in tissue printing wherein different photoinitiators for polymerization that respond to different wavelengths may be used in combination or in series to prevent unwanted polymerization of left-over materials. Therefore, each of these laser lines may be tuned to a different multi-photon output wavelength, may have different peak power output, and may project a different element of the CAD image that comprises the tissue structure.

TABLE 1

Element descriptions for FIGS. 3A-3C

| Element Label | Description |
|---|---|
| 140a-c | Laser source. A first laser source 140a, a second laser source 140b, and a third laser source 140c may be a tunable multi-photon (femto-second pulsed) laser of a given power (e.g. between 1 and 50 watts and 640 to 1500 nm wavelength output). Femto-second laser sources may be tunable by computer software interaction and thus may be set to various wavelengths before or during the printing process to produce different excitation wavelengths. Optionally, the systems disclosed herein may have a pump laser system. |
| A | Mirror. A mirror with or without an infrared (IR) specific coating to improve reflectance. IR specific coating examples may include protected gold or protected silver based coatings. As shown in FIG. 3A, grating and/or mirrors may be added between elements "F" (i.e., between DMDs, SLMs, or TAG lenses). |
| B | Beam expander. An optional beam expander to expand the area of the laser pulse prior to projection by the DMD or SLM systems. |
| C | Axicon or TAG lens. In some tissue printing applications, the use of a Bessel beam may allow for improved or even power output at greater depths in hydrogels, media, or already printed structures. To produce a Bessel beam, an axicon which produces a fixed Bessel beam or tunable acoustic gradient lens (TAG), may produce a Bessel beam that is tunable and can be altered by altering an electric signal input. In the instance that a TAG lens is used, the input signal may be controlled by integrated computer software. |
| D | Dispersion compensation unit. The purpose of the dispersion compensation unit in this design is to concentrate emitted two-photon packets such that the peak power output is higher at the excitation point. This allows for improved polymerization as a result of improved peak power output at a specific wavelength. |
| E | Beam Dump. Beam dump allows for collection of stray laser light. |
| F | DMD, SLM, or TAG lens. In this example design, a DMD or SLM may be used to create an x, y plane of projection with a specific pattern of light that may be used to polymerize the monomers into structures or nets that contain cells. The addition of the second DMD or SLM may allow for projection of the x, y plane in the z or axial direction for three-dimensional holographic projection of the multiphoton excitation into the print vessel. This may allow for polymerization of the structures in three dimensions wherein all x, y, and z dimension features are deposited at the same time. Each DMD or SLM may be controlled by computer input and may be directed to project a specific CAD image or portion of a CAD image. Having the SLM or DMDs in series may allow for images to be projected simultaneously in different wavelengths of light in the case of multiple laser excitation sources (such as illustrated in FIG. 3B) or in the case of multiple repeating pattern projection SLMs or DMDs can be used to project different aspects of the same tissue without needing to switch the computer input, instead mirrors can be used to re-direct or turn 'off' or 'on' a particular light path and produce a given fixed structure associated with laser light paths 1, 2, 3, or 4. In cases where the Bessel beam is removed (element C), this may allow for different axial accuracies in printing a particular given structure. Therefore, certain elements of tissue structure may be better printed by different light paths. Rapid switching between laser light paths can allow for printing and polymerization to continue while an SLM or DMD series is re-programmed for projection of the next tissue structure in a given series of printing steps. In some cases, element "F" can represent a TAG lens. The TAG lens as used as element "F" can manipulate light. The TAG lens as used as element "F" can holographically distribute light. |
| G | Movable mirror. A mirror with or without an IR specific coating to improve reflectance. IR specific coating examples may include protected gold or protected silver based coatings. These mirrors can be moveable and can be adjusted to be in an 'on' or 'off' state to redirect the laser light path through the printing system as desired. Control of mirror positioning may be dictated by computer software. |
| H | Beam combiner. Beam combiner allowing for multiple light paths to be recombined for simultaneous printing at different wavelengths. In FIG. 3B these may also be movable mirrors (G) that can allow for the same wavelengths to be printed with timed on/off states of the mirrors G. |
| I | Light path to the optics housing. |
| J | Band pass filter. The purpose of an optional band-pass filter may be to select a specific wavelength to be used in materials polymerization. Multi-photon excitation may have an emission spread that can span several tens of nanometers potentially leading to overlap in absorption and thus polymerization of materials with otherwise distinct absorption peaks. By selecting for specific wavelengths using a band pass filter the wavelength leading to polymerization may be fine-tuned to prevent undesirable cross-over effects when two different monomers with different responsiveness used in the same formulation. |
| K | Scan head. Two mirrors that represent optional laser light scanning or sintering in the x, y plane. These mirrors may vibrate at a given frequency, for example 20 kHz, one in the x-direction reflecting to the next mirror which may scan in the y direction. This scanning may create a plane of light that can be used to image tissues or polymerized units before, after, and during the polymerization process. This is possible as collagen and many other ordered structures can emit light via a non-linear process call second harmonic generation when polymerized but not when in a monomeric state. Therefore, using an additional excitation source tuned to a wavelength that may allow for second harmonic generation and imaging while not polymerizing the biomaterials can be useful for monitoring the printing process. |
| L | Long pass Mirror: A long pass mirror may allow multi-photon excitation from light path number 4 to pass through while reflecting any emission from a sample while in imaging mode (requires engagement of laser light path 4) to the series of photomultiplier tubes (PMT) M detectors and long pass or band pass mirrors of various wavelengths that may allow for specific emission wavelengths to be reflected into the PMTs for image collection via personal computer (PC) (i.e., computer processor) and appropriate imaging processing software. |
| M | Photo multiplier tubes. PMTs may be used in collection of images in microscopy. |

TABLE 1-continued

Element descriptions for FIGS. 3A-3C

| Element Label | Description |
| --- | --- |
| N | Objective. This objective may serve the purpose of concentrating the multiphoton excitation such that polymerization of monomers to match the projected image may take place. |
| O | Movable long pass mirror. In instances where imaging may be performed with light path #4 the mirror O may be moved via software control to allow for laser light path 4 to enter the objective (N). In some incarnations light path 4 may be tuned to a distinct wavelength from laser light paths 1, 2, or 3 allowing for a long or short pass mirror or beam combiner to be used in place of O. |
| 1 | Laser light path 1 may be used to by-pass the beam expansion or beam expansion plus Bessel beam lens combination in favor of direct transmittance into the SLM/DMD series or individual SLM or DMD. Laser line one may also be redirected into laser line 5 which creates a single two photon pinpoint excitation, which may be used in optics housing alignment or raster scanning of a sample for imaging purposes. |
| 2 & 5 | Laser light path 2 may be transmitted through an optional beam expander and optional Bessel beam creating lens (axicon or TAG lens) then a single SLM or DMD and may also be re-directed to laser light path 5. |
| 3 & 4 | Laser light paths 3 and 4 may be passed through an optional beam expander and optional Bessel beam creating lens (axicon or TAG lens) followed by a combination of SLM or DMDs in series. Two distinct laser lines may allow for construction of dual SLM, dual DMD or a combination of the two which can increase flexibility in printing different sizes and types of structures. Furthermore, the laser line can be flickered between two different structures projected by each series to allow for near-simultaneous printing of complex structures that may not otherwise be achieved with a single DMD or SLM series. At any time these laser lines may be re-directed to the beam dump E which functions as a default off state. |

Figure 4A:
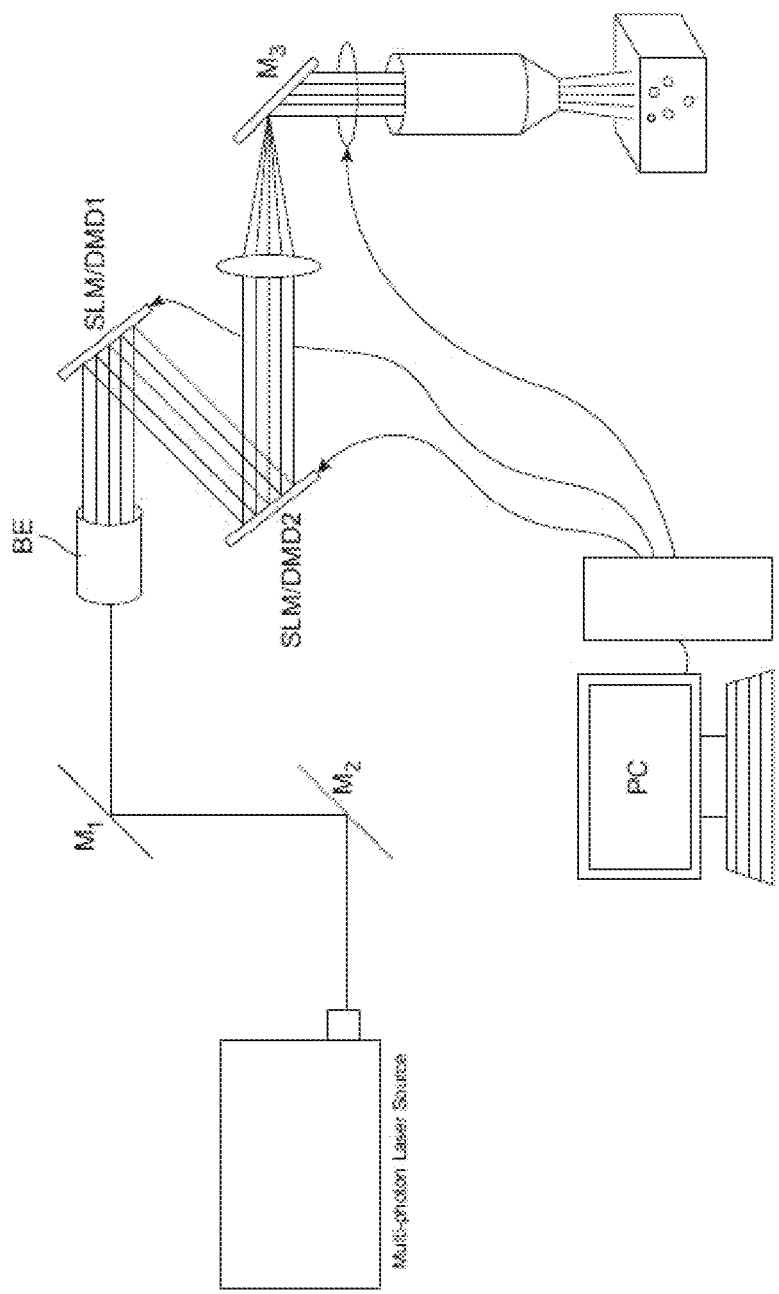
FIGS. 4A-4C illustrate various embodiments of the printing system.
Figure 4B:
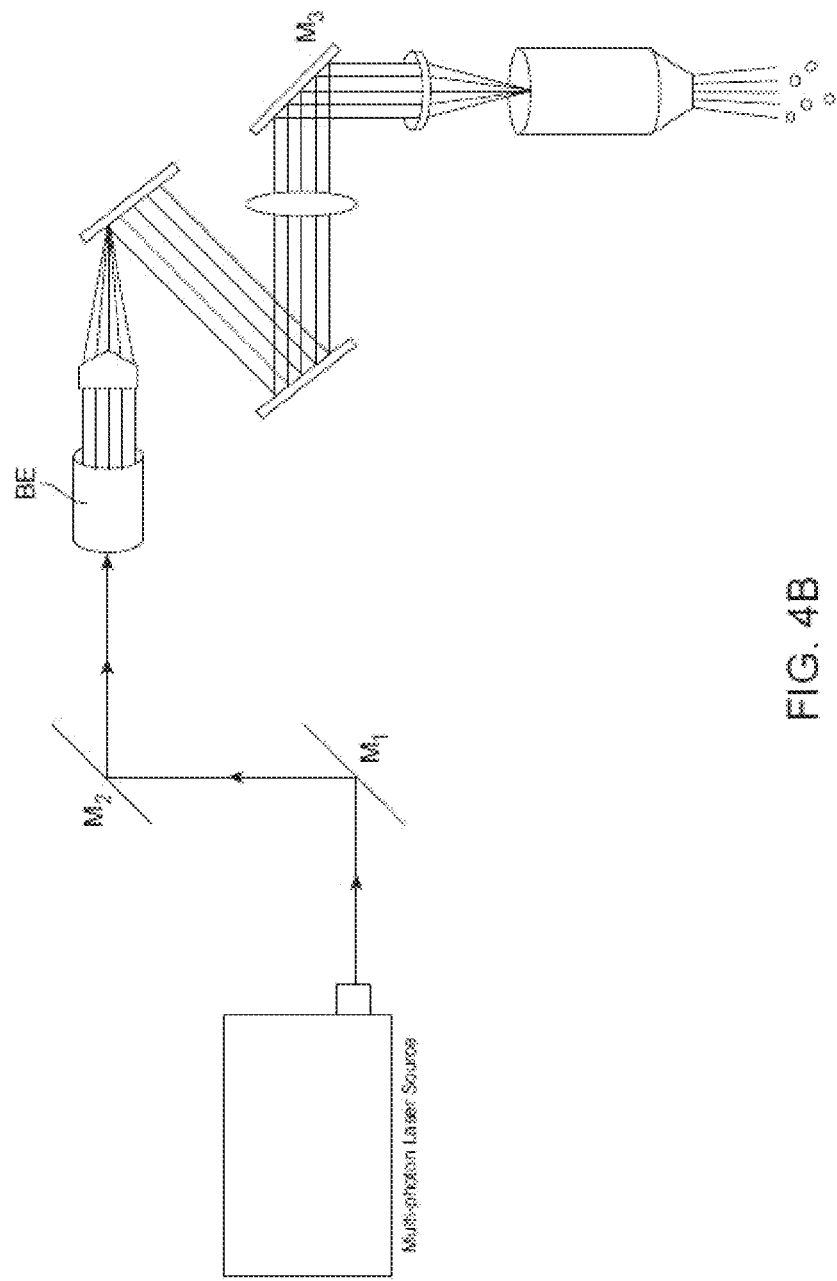

FIGS. 4A-4B demonstrates the placement of an optional beam expander prior to the axicon or tunable acoustic gradient (TAG) lens. This may allow for generation of a Bessel beam for the purpose of increased depth penetration in tissues and turbid media during printing without loss of focus fidelity. This feature may improve depth of printing through turbid media or through already formed tissues without loss of power.

A lens may be used to either widen or pre-focus the laser after the dual SLM or DMD combination. In addition, a laser attenuation device or filtering wheel that is computer controlled may be added prior to focusing optics to control the laser power output at the site of printing.

Figure 4C:
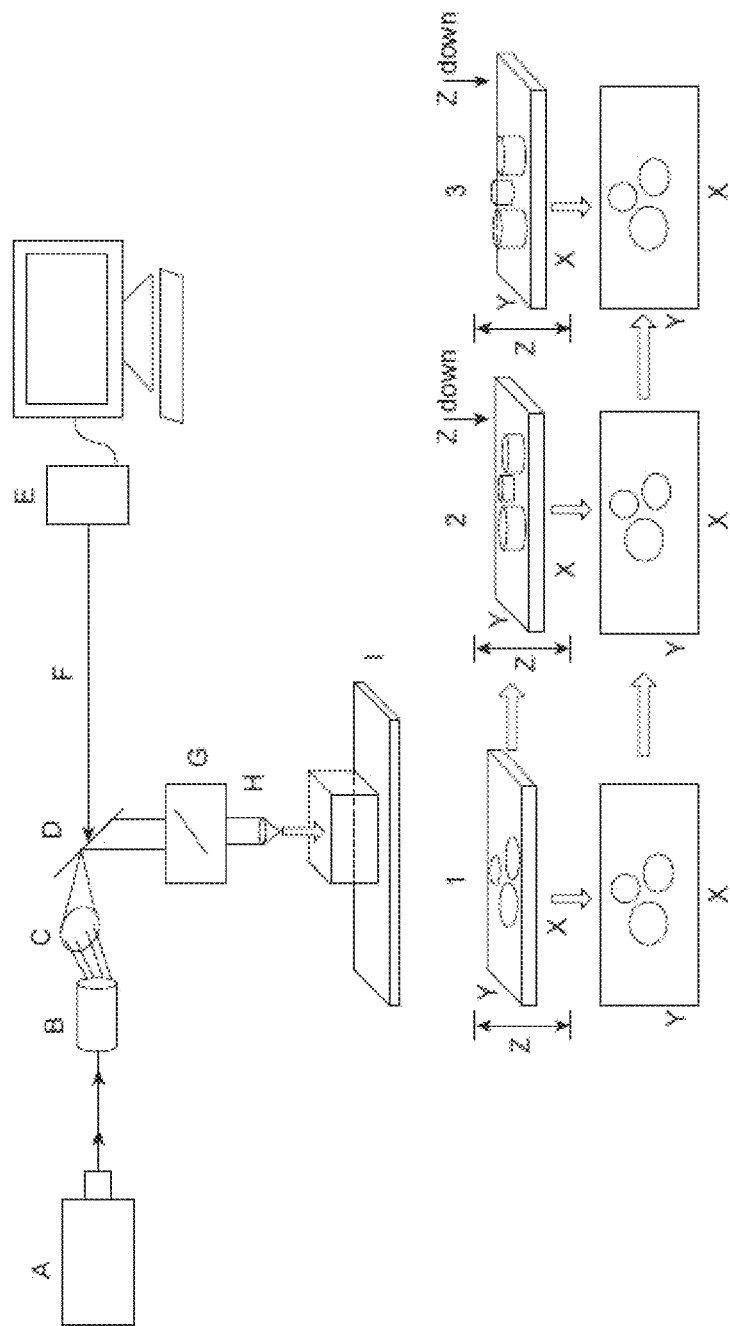

FIG. 4C illustrates a laser source A projecting a laser beam onto a beam collector B. Upon exiting the beam collector B, the laser beam may be directed to an optical TAG or axicon C and further to a movable, single SLM or DMD D for 2D x, y sheet projection for collagen net printing around cells and resultant structures printed with given Z-steps. The laser beam may be directed from the SLM or DMD D into a mirror G and then reflected onto the print head optics H. In this example, a two-dimensional (2D) projection may be created with a single SLM with a z-motor-stepped movement that matches the frame rate of the projection. Two-dimensional video projection of the z-stack slice may be achieved with a single DMD or a single SLM that is timed with z-movement such that each step projects a distinct image printing a 2D image from the top down. In another embodiment, a complex structure may be projected from the side, bottom up, or a different articulation and slice by slice, 2D projected and printed using either multi-photon or alternative laser excitation source. The source of CAD images F may be directed from the computer E into the system. The system may comprise a motorized stage I that may match the step rate (millisecond to second) and the step size of a Z-projection. The step size may be in the order of microns to nanometers. In FIG. 4C, 1, 2, and 3 illustrate examples of planar projection build steps.

Figure 12:
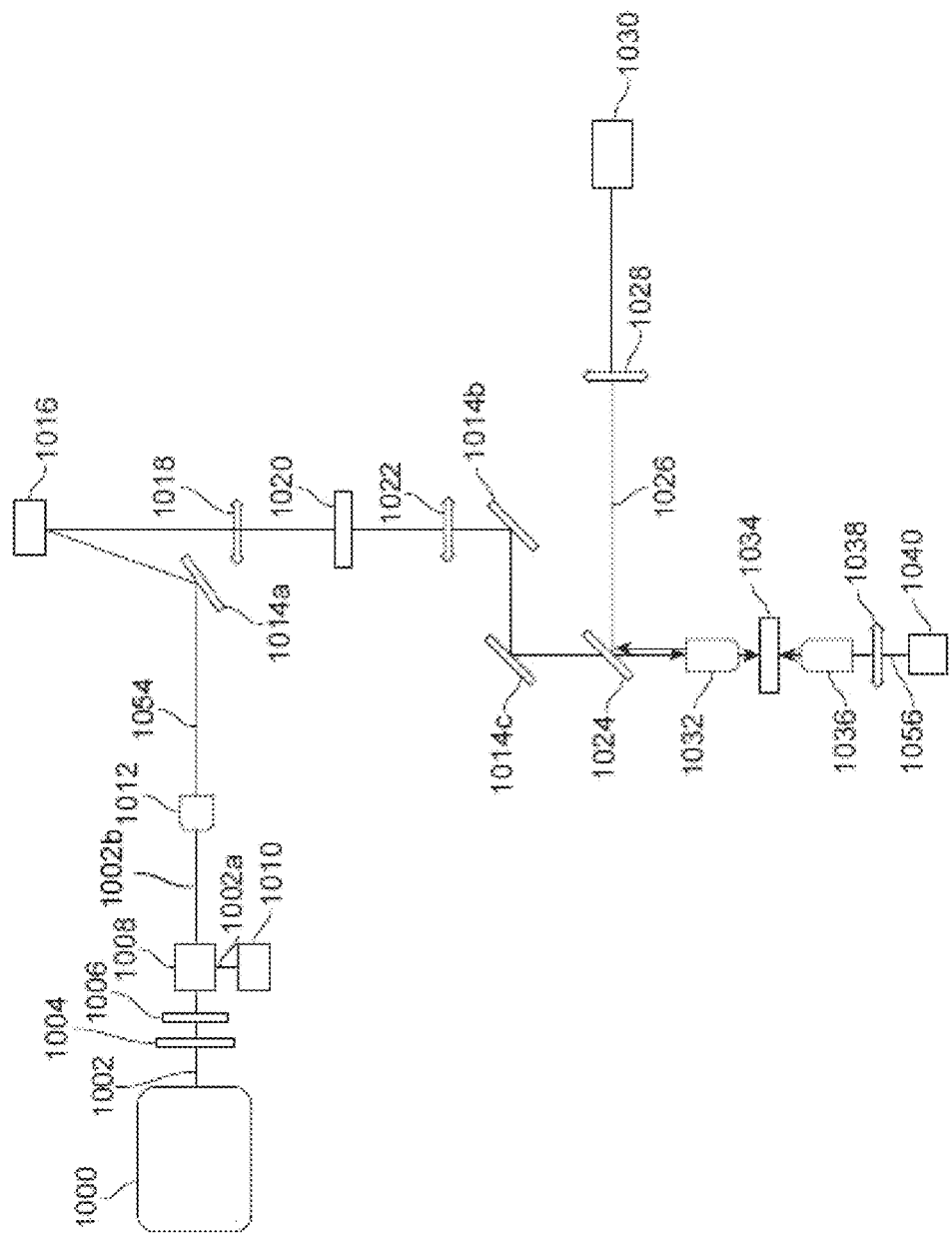
FIG. 12 illustrates the optical components and optical path of an embodiment of the printing system without temporal focusing.

FIG. 12 illustrates the optical components and the optical path of an embodiment of the three-dimensional printing system. The optical components and the optical path shown in FIG. 12 may provide a three-dimensional printing system that may not use temporal focusing. The three-dimensional printing system may comprise an energy source 1000. The energy source 1000 may be a coherent light source. The energy source 1000 may be a laser light. The energy source 1000 may be a femto-second pulsed laser light source. The energy source 1000 may be a first laser source 140*a*, a second laser source 140*b*, or a third laser source 140*c*. The energy source 1000 may be a multi-photon laser beam 120. The energy source 1000 may be a two-photon laser beam. The energy source 1000 may be controlled by a computer system 1101. The energy source 1000 may be tuned by a computer system 1101. The computer system 1101 may control and/or set the energy wavelength of the energy source 1000 prior to or during the printing process. They computer system 1101 may produce different excitation wavelengths by setting the wavelength of the energy source 1000.

The energy source 1000 may be pulsed. The energy source 1000 may be pulsed at a rate of about 500 kilohertz (kHz). The energy source 1000 (e.g., laser) may provide energy (e.g., laser beam) having energy packets with pulsed energies (per packet) from about at least 1 micro joule (µJ) to 1,000,000 µJ. The energy source 1000 (e.g., laser) may provide energy (e.g., laser beam) having energy packets with pulsed energies (per packet) from about at least 1 micro joule (µJ) to 100,000 µJ or more. The energy source 1000 (e.g., laser) may provide energy (e.g., laser beam) having energy packets with pulsed energies (per packet) from about at least 1 micro joule (µJ) to 1,000 µJ or more. The energy source 1000 (e.g., laser) may provide energy (e.g., laser beam) having energy packets with pulsed energies (per packet) from about at least 1 micro joule (µJ) to 100 µJ or more. The energy source 1000 (e.g., laser) may provide energy (e.g., laser beam) having energy packets with pulsed energies (per packet) from about at least 10 micro joule (µJ) to 100 µJ or more. The energy source 1000 (e.g., laser) may provide energy (e.g., laser beam) having energy packets with pulsed energies (per packet) from about at least 1 micro joule (µJ) to 50 µJ or more. The energy source 1000 (e.g., laser) may provide energy (e.g., laser beam) having energy packets with pulsed energies (per packet) from about at least 1 micro joule (µJ) to 20 µJ or more. The energy source 1000 (e.g., laser) may provide energy (e.g., laser beam) having energy packets with pulsed energies (per packet) from about at least 1 micro joule (µJ) to 50 µJ or more. The energy source 1000 (e.g., laser) may provide energy (e.g., laser beam) having energy packets with pulsed energies (per packet) from about at least 40 micro joule (µJ) to 80 µJ or more. The energy source 1000 (e.g., laser) may provide energy (e.g., laser beam) having energy packets with pulsed energies (per packet) from about at least 120 micro joule (µJ) to 160 µJ or more.

The energy source 1000 (e.g., laser) may provide energy (e.g., laser beam) having energy packets with pulsed energies (per packet) of about 10 µJ The energy source 1000

(e.g., laser) may provide energy (e.g., laser beam) having energy packets with pulsed energies (per packet) of about 20 µJ The energy source 1000 (e.g., laser) may provide energy (e.g., laser beam) having energy packets with pulsed energies (per packet) of about 30 µJ The energy source 1000 (e.g., laser) may provide energy (e.g., laser beam) having energy packets with pulsed energies (per packet) of about 40 µJ The energy source 1000 (e.g., laser) may provide energy (e.g., laser beam) having energy packets with pulsed energies (per packet) of about 50 µJ The energy source 1000 (e.g., laser) may provide energy (e.g., laser beam) having energy packets with pulsed energies (per packet) of about 60 µJ The energy source 1000 (e.g., laser) may provide energy (e.g., laser beam) having energy packets with pulsed energies (per packet) of about 70 µJ The energy source 1000 (e.g., laser) may provide energy (e.g., laser beam) having energy packets with pulsed energies (per packet) of about 80 µJ The energy source 1000 (e.g., laser) may provide energy (e.g., laser beam) having energy packets with pulsed energies (per packet) of about 90 µJ The energy source 1000 (e.g., laser) may provide energy (e.g., laser beam) having energy packets with pulsed energies (per packet) of about 100 µJ The energy source 1000 (e.g., laser) may provide energy (e.g., laser beam) having energy packets with pulsed energies (per packet) of about 110 µJ The energy source 1000 (e.g., laser) may provide energy (e.g., laser beam) having energy packets with pulsed energies (per packet) of about 120 µJ. The energy source 1000 (e.g., laser) may provide energy (e.g., laser beam) having energy packets with pulsed energies (per packet) of about 130 µJ. The energy source 1000 (e.g., laser) may provide energy (e.g., laser beam) having energy packets with pulsed energies (per packet) of about 140 µJ. The energy source 1000 (e.g., laser) may provide energy (e.g., laser beam) having energy packets with pulsed energies (per packet) of about 150 µJ The energy source 1000 (e.g., laser) may provide energy (e.g., laser beam) having energy packets with pulsed energies (per packet) of about 160 µJ. The energy source 1000 (e.g., laser) may provide energy (e.g., laser beam) having energy packets with pulsed energies (per packet) of about 170 µJ The energy source 1000 (e.g., laser) may provide energy (e.g., laser beam) having energy packets with pulsed energies (per packet) of about 180 µJ The energy source 1000 (e.g., laser) may provide energy (e.g., laser beam) having energy packets with pulsed energies (per packet) of about 190 µJ The energy source 1000 (e.g., laser) may provide energy (e.g., laser beam) having energy packets with pulsed energies (per packet) of about 200 µJ The energy source 1000 (e.g., laser) may provide energy (e.g., laser beam) having energy packets with pulsed energies (per packet) of about 20,000 µJ. The energy source 1000 (e.g., laser) may provide energy (e.g., laser beam) having energy packets with pulsed energies (per packet) of about 100,000 µJ The energy source 1000 (e.g., laser) may provide energy (e.g., laser beam) having energy packets with pulsed energies (per packet) of about 1,000,000 µJ.

The energy source 1000 (e.g., laser) may provide an energy beam (e.g., light beam) having a wavelength from e.g. about at least 300 nm to about 5 mm or more. The energy source 1000 (e.g., laser) may provide energy (e.g., laser beam) having a wavelength of about at least 600 to about 1500 nm or more. The energy source 1000 (e.g., laser) may provide energy (e.g., laser beam) having a wavelength from about at least 350 nm to about 1800 nm or more. The energy source 1000 (e.g., laser) may provide energy (e.g., laser beam) having a wavelength from about at least 1800 nm to about 5 mm or more. The energy source 1000 (e.g., laser) may provide energy (e.g., laser beam) having a wavelength of about 300 nm. The energy source 1000 (e.g., laser) may provide energy (e.g., laser beam) having a wavelength of about 400 nm. The energy source 1000 (e.g., laser) may provide energy (e.g., laser beam) having a wavelength of about 600 nm. The energy source 1000 (e.g., laser) may provide energy (e.g., laser beam) having a wavelength of about 700 nm. The energy source 1000 (e.g., laser) may provide energy (e.g., laser beam) having a wavelength of about 800 nm. The energy source 1000 (e.g., laser) may provide energy (e.g., laser beam) having a wavelength of about 900 nm. The energy source 1000 (e.g., laser) may provide energy (e.g., laser beam) having a wavelength of about 1000 nm. The energy source 1000 (e.g., laser) may provide energy (e.g., laser beam) having a wavelength of about 1100 nm. The energy source 1000 (e.g., laser) may provide energy (e.g., laser beam) having a wavelength of about 1200 nm. The energy source 1000 (e.g., laser) may provide energy (e.g., laser beam) having a wavelength of about 1300 nm. The energy source 1000 (e.g., laser) may provide energy (e.g., laser beam) having a wavelength of about 1400 nm. The energy source 1000 (e.g., laser) may provide energy (e.g., laser beam) having a wavelength of about 1500 nm. The energy source 1000 (e.g., laser) may provide energy (e.g., laser beam) having a wavelength of about 1600 nm. The energy source 1000 (e.g., laser) may provide energy (e.g., laser beam) having a wavelength of about 1700 nm. The energy source 1000 (e.g., laser) may provide energy (e.g., laser beam) having a wavelength of about 1800 nm. The energy source 1000 (e.g., laser) may provide energy (e.g., laser beam) having a wavelength of about 1900 nm. The energy source 1000 (e.g., laser) may provide energy (e.g., laser beam) having a wavelength of about 2000 nm. The energy source 1000 (e.g., laser) may provide energy (e.g., laser beam) having a wavelength of about 3000 nm. The energy source 1000 (e.g., laser) may provide energy (e.g., laser beam) having a wavelength of about 4000 nm. The energy source 1000 (e.g., laser) may provide energy (e.g., laser beam) having a wavelength of about 5000 nm.

As shown in FIG. 12, the energy source 1000 may project a laser beam 1002 through a shutter 1004. Once the laser beam 1002 exits the shutter 1004, the laser beam 1002 may be directed through a rotating half-wave plate 1006. Rotating half-wave plates may be transparent plates with a specific amount of birefringence that may be used mostly for manipulating the polarization state of light beams. Rotating half-wave plates may have a slow axis and a fast axis (i.e., two polarization directions), which may be both perpendicular to the direction of the laser beam 1002. The rotating half-wave plate 1006 may alter the polarization state of the laser beam 1002 such that the difference in phase delay between the two linear polarization directions is $\pi$. The difference in phase delay may correspond to a propagation phase shift over a distance of $\lambda/2$. Other types of wave plates may be utilized with the system disclosed herein; for example, a rotating quarter-wave plate may be used. The rotating half-wave plate 1006 may be a true zero-order wave plate, a low order wave plate, or a multiple-order wave plate. The rotating half-wave plate 1006 may be composed of crystalline quartz ($SiO_2$), calcite ($CaCO_3$), magnesium fluoride ($MgF_2$), sapphire ($Al_2O_3$), mica, or a birefringent polymer.

The laser beam 1002 may exit the rotating half-wave plate 1006 and may be directed through a polarizing beam splitter 1008. The polarizing beam splitter 1008 may split the laser beam 1002 into a first laser beam 1002a and a second laser beam 1002b. The first laser beam 1002a may be directed to a beam dump 1010. The beam dump 1010 is an optical element that may be used to absorb stray portions of a laser beam. The beam dump 1010 may absorb the first laser beam 1002a. The first laser beam 1002a may be a stray laser beam. The beam dump 1010 may absorb the second laser beam 1002b. The second laser beam 1002b may be a stray laser beam. The laser beam 1002 may be directed into the beam dump 1010 in its entirety and thus, may serve as a default "off" state of the printing system. The second laser beam 1002b may be directed to a beam expander 1012. The beam expander 1012 may expand the size of the laser beam 1002b. The beam expander 1012 may increase the diameter of the input second laser beam 1002b to a larger diameter of an output, expanded laser beam 1054. The beam expander 1012 may be a prismatic beam expander. The beam expander 1012 may be a telescopic beam expander. The beam expander 1012 may be a multi-prism beam expander. The beam expander 1012 may be a Galilean beam expander. The beam expander 1012 may provide a beam expander power of about 2×, 3×, 5×, 10×, 20×, or 40×. The beam expander 1012 may provide a beam expander power ranging from about 2× to about 5×. The beam expander 1012 may provide continuous beam expansion between about 2× and about 5×. The beam expander 1012 may provide a beam expander power ranging from about 5× to about 10×. The beam expander 1012 may provide continuous beam expansion between about 5× and about 10×. The expanded laser beam 1054 may be collimated upon exiting the beam expander 1012.

After exiting the beam expander 1012, the expanded laser beam 1054 may be directed to a first mirror 1014a, which may re-direct the expanded laser beam 1054 to a spatial light modulator (SLM) 1016. The SLM 1016 may be controlled by a computer system 1101. The SLM 1016 may be directed to project a specific image or a specific portion of an image of a material to be printed using the methods and systems disclosed herein. The material to be printed may be a biological material. The biological material may be a three-dimensional biological material. The specific image or the specific portion of the image may be one-dimensional, two-dimensional, and/or three-dimensional. The SLM 1016 may be directed to project at least one image simultaneously in different wavelengths of light. The SLM 1016 may be directed to project different aspects of the material to be printed with the use of mirrors instead of with the use of a computer system 1101. In some cases, at least one mirror may be used to re-direct or turn "off" or "on" a particular light path or laser beam in order to print different aspects or portions of the material to be printed.

After exiting the SLM 1016, the expanded laser beam 1054 may be directed to an f1 lens 1018. The f1 lens 1018 may be a focusing lens. After exiting the f1 lens 1018, the expanded laser beam 1054 may be directed to blocking element 1020. The blocking element 1020 may be immovable. The blocking element 1020 may suppress illumination from a zero-order spot. A zero-order may be a part of the energy from the expanded laser beam 1054 that is not diffracted and behaves according to the laws or reflection and refraction. After exiting the blocking element 1020, the expanded energy beam 1054 may be directed through an f2 lens 1022. The f2 lens may be a focusing lens.

After exiting the f2 lens 1022, the expanded laser beam 1054 may be directed onto a second mirror 1014b and may be subsequently directed onto a third mirror 1014c. The third mirror 1014c may re-direct the expanded laser beam 1054 through a long pass dichroic mirror 1024. The first mirror 1014a, the second mirror 1014b, and/or the third mirror 1014c may comprise an infrared (IR) coating to improve reflectance. The first mirror 1014a, the second mirror 1014b, and/or the third mirror 1014c may not comprise an infrared (IR) coating. Non-limiting examples of IR coatings include protected gold-based coatings and protected silver-based coatings. The first mirror 1014a, the second mirror 1014b, and/or the third mirror 1014c may be controlled with a computer system 1101. The computer system 1101 may turn the first mirror 1014a, the second mirror 1014b, and/or the third mirror 1014c "on" or "off" in order to re-direct the expanded laser beam 1054 as desired.

The dichroic mirror may be a short pass dichroic mirror. The long pass dichroic mirror 1024 may reflect the expanded laser beam 1054 into the focusing objective 1032. In some instances, a beam combiner may be used to re-direct the expanded laser beam 1054 into the focusing objective 1032 instead of using the long pass dichroic mirror 1024. The long pass dichroic mirror 1024 may be controlled with a computer system 1101 to re-direct the expanded laser beam 1054 into the focusing objective 1032. The focusing objective 1032 may concentrate the expanded laser beam 1054 as it is projected into the printing chamber 1034. The printing chamber 1034 may be a media chamber 122. The printing chamber 1034 may comprise a cell-containing medium, a plurality of cells, cell constituents (e.g., organelles), and/or at least one polymer precursor.

A light-emitting diode (LED) collimator 1040 may be used as a source of collimated LED light 1056. The LED collimator 1040 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1040 may project a beam of collimated LED light 1056 through an f4 lens 1038. The f4 lens 1038 may be a focusing lens. Once the collimated LED light 1056 is transmitted through the f4 lens 1038, the collimated LED light 1056 may be directed into a light focusing objective 1036. The light focusing objective 1036 may focus the collimated LED light 1056 into the printing chamber 1034. The light focusing objective 1036 may focus the collimated LED light 1056 in the sample medium. The light focusing objective 1036 may focus the collimated LED light 1056 in the cell-containing medium. The collimated LED light 1056 may be transmitted through the printing chamber 1034 and into the focusing objective 1032. Once the collimated LED light 1056 exits the focusing objective 1032, the collimated LED light 1056 may be directed onto the long pass dichroic mirror 1024. The collimated LED light 1056 that is reflected off of the long pass dichroic mirror 1024 may be the sample emission 1026. The long pass dichroic mirror 1024 may re-direct the sample emission 1026 into an f3 lens 1028. The f3 lens 1028 may be a focusing lens. Once sample emission 1026 is transmitted through the f3 lens 1028, a detection system 1030 detects and/or collects the sample emission 1026 for imaging. The detection system 1030 may comprise at least one photomultiplier tube (PMT). The detection system 1030 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1030 may comprise at least one array-based detector.

Figure 13:
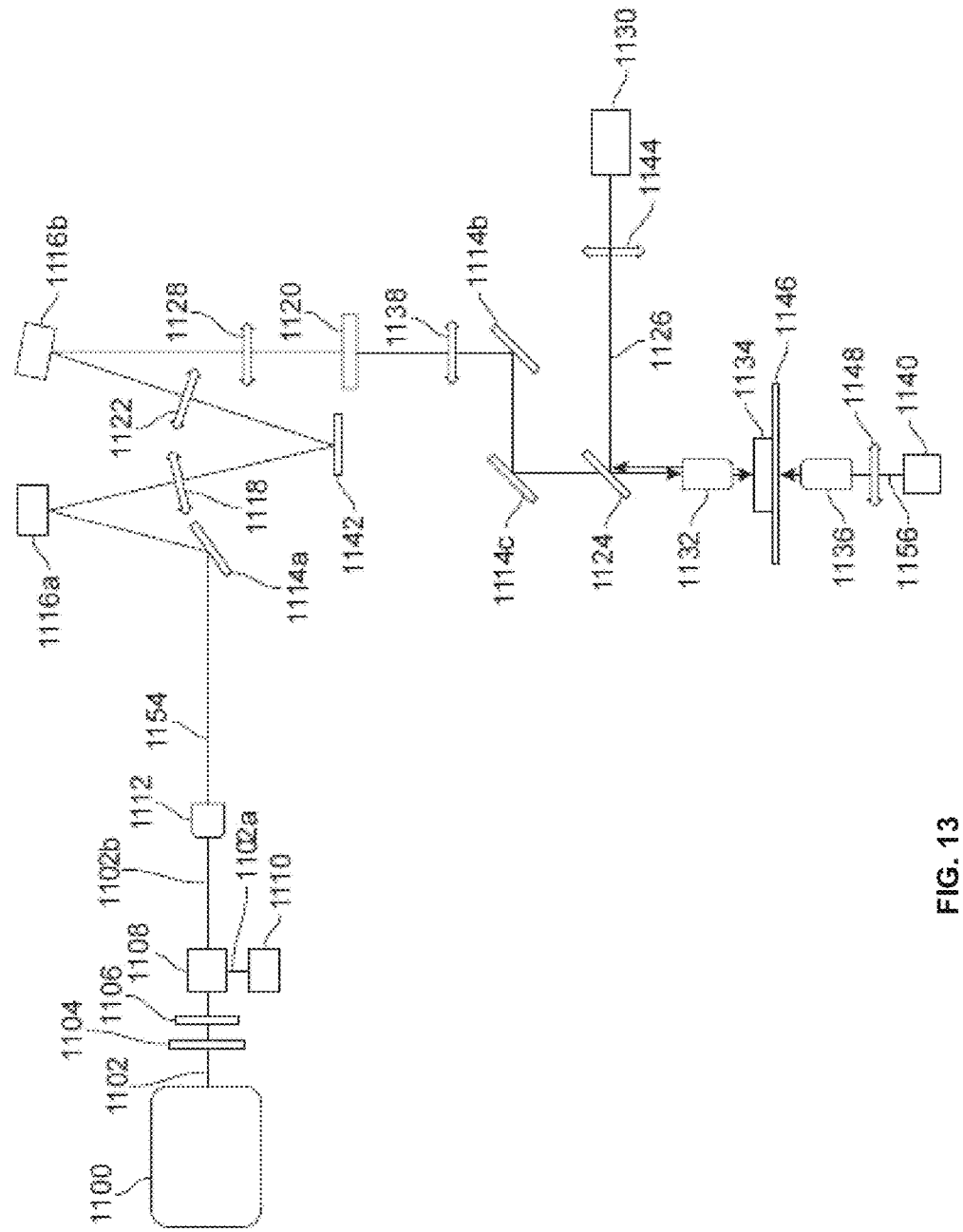
FIG. 13 illustrates the optical components and optical path of an additional embodiment of the printing system with temporal focusing.

FIG. 13 illustrates the optical components and the optical path of yet another embodiment of the three-dimensional printing system. The optical components and the optical path shown in FIG. 13 provide a three-dimensional printing system that may use temporal focusing. The three-dimensional printing system may comprise an energy source 1100. The energy source 1100 may be a coherent light source. The energy source 1100 may be a laser light. The energy source 1100 may be a femto-second pulsed laser light source. The energy source 1100 may be a first laser source 140a, a second laser source 140b, or a third laser source 140c. The energy source 1100 may be a multi-photon laser beam 120. The energy source 1100 may be a two-photon laser beam. The energy source 1100 may be controlled by a computer system 1101. The energy source 1100 may be tuned by a computer system 1101. The computer system 1101 may control and/or set the energy wavelength of the energy source 1100 prior to or during the printing process. They computer system 1101 may produce different excitation wavelengths by setting the wavelength of the energy source 1100.

The energy source 1100 may be pulsed. The energy source 1100 may be pulsed at a rate of about 500 kilohertz (kHz). The energy source 1100 (e.g., laser) may provide energy (e.g., laser beam) having energy packets with pulsed energies (per packet) from about at least 1 micro joule (μJ) to 1,000,000 μJ. The energy source 1100 (e.g., laser) may provide energy (e.g., laser beam) having energy packets with pulsed energies (per packet) from about at least 1 micro joule (μJ) to 100,000 μJ or more. The energy source 1100 (e.g., laser) may provide energy (e.g., laser beam) having energy packets with pulsed energies (per packet) from about at least 1 micro joule (μJ) to 1,000 μJ or more. The energy source 1100 (e.g., laser) may provide energy (e.g., laser beam) having energy packets with pulsed energies (per packet) from about at least 1 micro joule (μJ) to 1000 or more. The energy source 1100 (e.g., laser) may provide energy (e.g., laser beam) having energy packets with pulsed energies (per packet) from about at least 10 micro joule (μJ) to 100 μJ or more. The energy source 1100 (e.g., laser) may provide energy (e.g., laser beam) having energy packets with pulsed energies (per packet) from about at least 1 micro joule (μJ) to 50 μJ or more. The energy source 1100 (e.g., laser) may provide energy (e.g., laser beam) having energy packets with pulsed energies (per packet) from about at least 1 micro joule (μJ) to 20 μJ or more. The energy source 1100 (e.g., laser) may provide energy (e.g., laser beam) having energy packets with pulsed energies (per packet) from about at least 1 micro joule (μJ) to 50 μJ or more. The energy source 1100 (e.g., laser) may provide energy (e.g., laser beam) having energy packets with pulsed energies (per packet) from about at least 40 micro joule (μJ) to 80 μJ or more. The energy source 1100 (e.g., laser) may provide energy (e.g., laser beam) having energy packets with pulsed energies (per packet) from about at least 120 micro joule (μJ) to 160 μJ or more.

The energy source 1100 (e.g., laser) may provide energy (e.g., laser beam) having energy packets with pulsed energies (per packet) of about 10 μJ The energy source 1100 (e.g., laser) may provide energy (e.g., laser beam) having energy packets with pulsed energies (per packet) of about 20 μJ The energy source 1100 (e.g., laser) may provide energy (e.g., laser beam) having energy packets with pulsed energies (per packet) of about 30 μJ The energy source 1100 (e.g., laser) may provide energy (e.g., laser beam) having energy packets with pulsed energies (per packet) of about 40 μJ The energy source 1100 (e.g., laser) may provide energy (e.g., laser beam) having energy packets with pulsed energies (per packet) of about 50 μJ The energy source 1100 (e.g., laser) may provide energy (e.g., laser beam) having energy packets with pulsed energies (per packet) of about 60 μJ The energy source 1100 (e.g., laser) may provide energy (e.g., laser beam) having energy packets with pulsed energies (per packet) of about 70 μJ The energy source 1100 (e.g., laser) may provide energy (e.g., laser beam) having energy packets with pulsed energies (per packet) of about 80 μJ The energy source 1100 (e.g., laser) may provide energy (e.g., laser beam) having energy packets with pulsed energies (per packet) of about 90 μJ The energy source 1100 (e.g., laser) may provide energy (e.g., laser beam) having energy packets with pulsed energies (per packet) of about 100 μJ The energy source 1100 (e.g., laser) may provide energy (e.g., laser beam) having energy packets with pulsed energies (per packet) of about 110 μJ The energy source 1100 (e.g., laser) may provide energy (e.g., laser beam) having energy packets with pulsed energies (per packet) of about 120 μJ. The energy source 1100 (e.g., laser) may provide energy (e.g., laser beam) having energy packets with pulsed energies (per packet) of about 130 μJ. The energy source 1100 (e.g., laser) may provide energy (e.g., laser beam) having energy packets with pulsed energies (per packet) of about 140 μJ. The energy source 1100 (e.g., laser) may provide energy (e.g., laser beam) having energy packets with pulsed energies (per packet) of about 150 μJ The energy source 1100 (e.g., laser) may provide energy (e.g., laser beam) having energy packets with pulsed energies (per packet) of about 160 μJ. The energy source 1100 (e.g., laser) may provide energy (e.g., laser beam) having energy packets with pulsed energies (per packet) of about 170 μJ The energy source 1100 (e.g., laser) may provide energy (e.g., laser beam) having energy packets with pulsed energies (per packet) of about 180 μJ The energy source 1100 (e.g., laser) may provide energy (e.g., laser beam) having energy packets with pulsed energies (per packet) of about 190 μJ The energy source 1100 (e.g., laser) may provide energy (e.g., laser beam) having energy packets with pulsed energies (per packet) of about 200 μJ The energy source 1100 (e.g., laser) may provide energy (e.g., laser beam) having energy packets with pulsed energies (per packet) of about 20,000 μJ. The energy source 1100 (e.g., laser) may provide energy (e.g., laser beam) having energy packets with pulsed energies (per packet) of about 100,000 μJ The energy source 1100 (e.g., laser) may provide energy (e.g., laser beam) having energy packets with pulsed energies (per packet).

The energy source 1100 (e.g., laser) may provide energy (e.g., laser beam) having a wavelength from about 300 nm to 5 mm, 600 nm to 1500 nm, 350 nm to 1800 nm, or 1800 nm to 5 mm. The energy source 1100 (e.g., laser) may provide energy (e.g., laser beam) having a wavelength of at least about 300 nm, 400 nm, 500 nm, 600 nm, 700 nm, 800 nm, 900 nm, 1 mm, 1.1 mm, 1.2, mm, 1.3 mm, 1.4 mm, 1.5 mm, 1.6 mm, 1.7 mm, 1.8 mm, 1.9 mm, 2 mm, 3 mm, 4 mm, 5 mm, or greater.

As shown in FIG. 13, the energy source 1100 may project a laser beam 1102 through a shutter 1104. Once the laser beam 1102 exits the shutter 1104, the laser beam 1102 may be directed through a rotating half-wave plate 1106. The rotating half-wave plate 1106 may alter the polarization state of the laser beam 1102 such that the difference in phase delay between the two linear polarization directions is π. The difference in phase delay may correspond to a propagation phase shift over a distance of λ/2. Other types of wave plates may be utilized with the system disclosed herein; for example, a rotating quarter-wave plate may be used. The rotating half-wave plate 1106 may be a true zero-order wave plate, a low order wave plate, or a multiple-order wave plate. The rotating half-wave plate 1106 may be composed of crystalline quartz ($SiO_2$), calcite ($CaCO_3$), magnesium fluoride ($MgF_2$), sapphire ($Al_2O_3$), mica, or a birefringent polymer.

The laser beam 1102 may exit the rotating half-wave plate 1106 and may be directed through a polarizing beam splitter 1108. The polarizing beam splitter 1108 may split the laser beam 1102 into a first laser beam 1102a and a second laser beam 1102b. The first laser beam 1102a may be directed to a beam dump 1110. The beam dump 1110 is an optical element that may be used to absorb stray portions of a laser beam. The beam dump 1110 may absorb the first laser beam 1102a. The first laser beam 1102a may be a stray laser beam. The beam dump 1110 may absorb the second laser beam 1102b. The second laser beam 1102b may be a stray laser beam. The laser beam 1102 may be directed into the beam dump 1110 in its entirety and thus, may serve as a default "off" state of the printing system. The second laser beam 1102b may be directed to a beam expander 1112. The beam expander 1112 may expand the size of the second laser beam 1102b. The beam expander 1112 may increase the diameter of the input, second laser beam 1102b to a larger diameter of an output, expanded laser beam 1154. The beam expander 1112 may be a prismatic beam expander. The beam expander 1112 may be a telescopic beam expander. The beam expander 1112 may be a multi-prism beam expander. The beam expander 1112 may be a Galilean beam expander. The beam expander 1112 may provide a beam expander power of about 2×, 3×, 5×, 10×, 20×, or 40×. The beam expander 1112 may provide a beam expander power ranging from about 2× to about 5×. The beam expander 1112 may provide continuous beam expansion between about 2× and about 5×. The beam expander 1112 may provide a beam expander power ranging from about 5× to about 10×. The beam expander 1112 may provide continuous beam expansion between about 5× and about 10×. The expanded laser beam 1154 may be collimated upon exiting the beam expander 1112.

After exiting the beam expander 1112, the expanded laser beam 1154 may be directed to a first mirror 1114a, which may re-direct the expanded laser beam 1154 to a first spatial light modulator (SLM) 1116a. After exiting the first SLM 1116, the expanded laser beam 1154 may be directed to an f1 lens 1118. The f1 lens 1118 may be a focusing lens. After exiting the f1 lens, the expanded laser beam 1154 may be directed to a grating 1142. The grating 1142 may be a diffractive laser beam splitter. The grating 1142 may be a holographic grating. The grating 1142 may be a ruled grating. The grating 1142 may be a subwavelength grating. The grating 1142 may split and/or diffract the expanded laser beam 1154 into a plurality of expanded laser beams (not shown in FIG. 13). The grating 1142 may act as a dispersive element. Once the expanded laser beam 1154 is split, diffracted, and/or dispersed by the grating 1142, the expanded laser beam 1154 may be transmitted through an f2 lens 1122. The f2 lens 1122 may be a focusing lens. After exiting the f2 lens 1122, the expanded laser beam 1154 may be directed to a second SLM 1116b. The SLMs (i.e., the first SLM 1116a and the second SLM 1116b) may be controlled by a computer system 1101. The SLMs may perform all of the functions, as described supra, of the SLM 1016 presented in FIG. 12.

After exiting the second SLM 1116b, the expanded laser beam 1154 may be directed to an f3 lens 1128. The f3 lens 1128 may be a focusing lens. After exiting the f3 lens, the expanded laser beam 1154 may be directed to blocking element 1120. The blocking element 1120 may be immovable. The blocking element 1120 may be used to suppress illumination from a zero-order spot. After exiting the blocking element 1120, the expanded energy beam 1154 may be directed through an f4 lens 1138. The f4 lens 1138 may be a focusing lens. After exiting the f4 lens 1138, the expanded laser beam 1154 may be directed onto a second mirror 1114b and may be subsequently directed onto a third mirror 1114c. The third mirror 1114c may re-direct the expanded laser beam 1154 through a long pass dichroic mirror 1124. The first mirror 1114a, the second mirror 1114b, and/or the third mirror 1114c may be controlled with a computer system 1101. The computer system 1101 may turn the first mirror 1114a, the second mirror 1114b, and/or the third mirror 1114c "on" or "off" in order to re-direct the expanded laser beam 1154 as desired. The dichroic mirror may be a short pass dichroic mirror. The long pass dichroic mirror 1124 may reflect the expanded laser beam 1154 into the focusing objective 1132. In some instances, a beam combiner may be used to re-direct the expanded laser beam 1154 into the focusing objective 1132 instead of using the long pass dichroic mirror 1124. The long pass dichroic mirror 1124 may be controlled with a computer system 1101 to re-direct the expanded laser beam 1154 into the focusing objective 1132. The focusing objective 1132 may concentrate the expanded laser beam 1154 as it is projected into the printing chamber 1134. The printing chamber 1134 may be a media chamber 122. The printing chamber 1134 may comprise a cell-containing medium, a plurality of cells, cell constituents (e.g., organelles), and/or at least one polymer precursor.

The printing chamber 1134 may be mounted on a movable stage 1146. The movable stage 1146 may be an xy stage, a z stage, and/or an xyz stage. The movable stage 1146 may be manually positioned. The movable stage 1146 may be automatically positioned. The movable stage 1146 may be a motorized stage. The movable stage 1146 may be controlled by the computer system 1101. The computer system 1101 may control the movement of the movable stage 1146 in the x, y, and/or z directions. The computer system 1101 may automatically position the movable stage 1146 in a desired x, y, and/or z position. The computer system 1101 may position the movable stage 1146 in a desired x, y, and/or z position with a positional accuracy of at most about 3 μm. The computer system 1101 may position the movable stage 1146 in a desired x, y, and/or z position with a positional accuracy of at most about 2 μm. The computer system 1101 may position the movable stage 1146 in a desired x, y, and/or z position with a positional accuracy of at most about 1 μm. The computer system 1101 may automatically adjust the position of the movable stage 1146 prior or during three-dimensional printing. The computer system 1101 may comprise a piezoelectric (piezo) controller to provide computer-controlled z-axis (i.e., vertical direction) positioning and active location feedback. The computer system 1101 may comprise a joystick console to enable a user to control a position of the movable stage 1146. The joystick console may be a z-axis console and/or an x-axis and y-axis console. The movable stage 1146 may comprise a printing chamber holder. The printing chamber holder may be a bracket, a clip, and/or a recessed sample holder. The movable stage 1146 may comprise a multi-slide holder, a slide holder, and/or a petri dish holder. The movable stage 1146 may comprise a sensor to provide location feedback. The sensor may be a capacitive sensor. Theسensor may be a piezoresistive sensor. The movable stage 1146 may comprise at least one actuator (e.g., piezoelectric actuator) that moves (or positions) the movable stage 1146.

A light-emitting diode (LED) collimator 1140 may be used as a source of collimated LED light 1156. The LED collimator 1140 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1140 may project a beam of collimated LED light 1156 through an f6 lens 1148. The f6 lens 1148 may be a focusing lens. Once the collimated LED light 1156 is transmitted through the f6 lens 1148, the collimated LED light 1156 may be directed into a light focusing objective 1136. The light focusing objective 1136 may focus the collimated LED light 1156 into the printing chamber 1134. The light focusing objective 1136 may focus the collimated LED light 1156 in the sample medium. The light focusing objective 1136 may focus the collimated LED light 1156 in the cell-containing medium. The collimated LED light 1156 may be transmitted through the printing chamber 1134 and into the focusing objective 1132. Once the collimated LED light 1156 exits the focusing objective 1132, the collimated LED light 1156 may be directed onto the long pass dichroic mirror 1124. The collimated LED light 1156 that is reflected off of the long pass dichroic mirror 1124 may be the sample emission 1126. The long pass dichroic mirror 1124 may re-direct the sample emission 1126 into an f5 lens 1144. The f5 lens 1144 may be a focusing lens. Once sample emission 1126 is transmitted through the f5 lens 1144, a detection system 1130 detects and/or collects the sample emission 1126 for imaging. The detection system 1130 may comprise at least one photomultiplier tube (PMT). The detection system 1130 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1130 may comprise at least one array-based detector.

Figure 14:
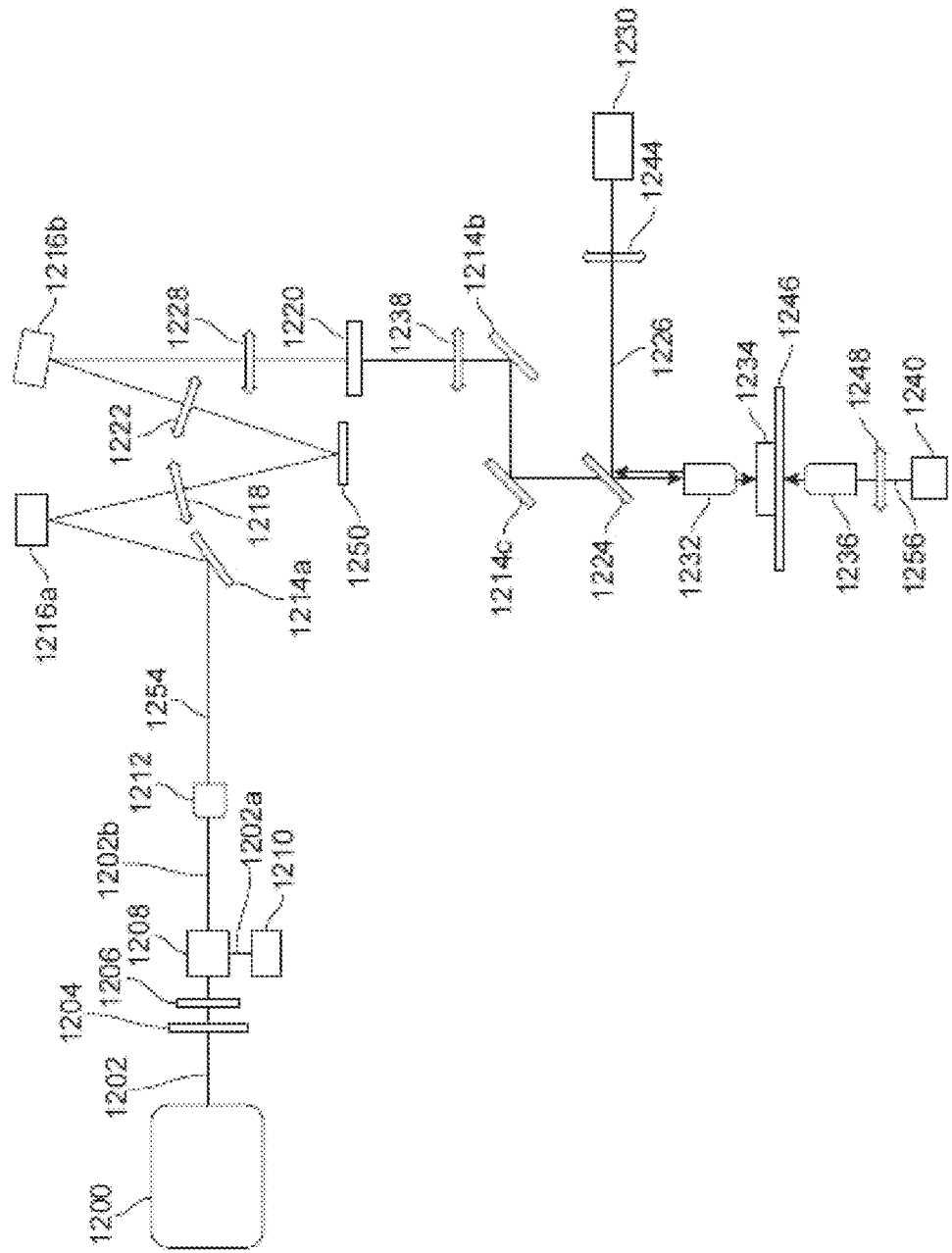
FIG. 14 illustrates the optical components and optical path of yet another embodiment of the printing system without temporal focusing.

FIG. 14 illustrates the optical components and the optical path of an additional embodiment of the three-dimensional printing system. The optical components and the optical path shown in FIG. 14 provide a three-dimensional printing system that may not use temporal focusing. The three-dimensional printing system may comprise an energy source 1200. The energy source 1200 may be a coherent light source. The energy source 1200 may be a laser light. The energy source 1200 may be a femto-second pulsed laser light source. The energy source 1200 may be a first laser source 140a, a second laser source 140b, or a third laser source 140c. The energy source 1200 may be a multi-photon laser beam 120. The energy source 1200 may be controlled by a computer system 1101. The energy source 1200 may be tuned by a computer system 1101. The computer system 1101 may control and/or set the energy wavelength of the energy source 1200 prior to or during the printing process. They computer system 1101 may produce different excitation wavelengths by setting the wavelength of the energy source 1200.

The energy source 1200 may be pulsed. The energy source 1200 may be pulsed at a rate of about 500 kilohertz (kHz). The energy source 1200 (e.g., laser) may provide energy (e.g., laser beam) having energy packets with pulsed energies (per packet) from about at least 1 micro joule ($\mu$J) to 1,000,000 $\mu$J. The energy source 1200 (e.g., laser) may provide energy (e.g., laser beam) having energy packets with pulsed energies (per packet) from about at least 1 micro joule ($\mu$J) to 100,000 $\mu$J or more. The energy source 1200 (e.g., laser) may provide energy (e.g., laser beam) having energy packets with pulsed energies (per packet) from about at least 1 micro joule ($\mu$J) to 1,000 $\mu$J or more. The energy source 1200 (e.g., laser) may provide energy (e.g., laser beam) having energy packets with pulsed energies (per packet) from about at least 1 micro joule ($\mu$J) to 1000 or more. The energy source 1200 (e.g., laser) may provide energy (e.g., laser beam) having energy packets with pulsed energies (per packet) from about at least 10 micro joule ($\mu$J) to 1000 or more. The energy source 1200 (e.g., laser) may provide energy (e.g., laser beam) having energy packets with pulsed energies (per packet) from about at least 1 micro joule ($\mu$J) to 50 $\mu$J or more. The energy source 1200 (e.g., laser) may provide energy (e.g., laser beam) having energy packets with pulsed energies (per packet) from about at least 1 micro joule ($\mu$J) to 20 $\mu$J or more. The energy source 1200 (e.g., laser) may provide energy (e.g., laser beam) having energy packets with pulsed energies (per packet) from about at least 1 micro joule ($\mu$J) to 50 $\mu$J or more. The energy source 1200 (e.g., laser) may provide energy (e.g., laser beam) having energy packets with pulsed energies (per packet) from about at least 40 micro joule ($\mu$J) to 80 $\mu$J or more. The energy source 1200 (e.g., laser) may provide energy (e.g., laser beam) having energy packets with pulsed energies (per packet) from about at least 120 micro joule ($\mu$J) to 160 $\mu$J or more.

The energy source 1200 (e.g., laser) may provide energy (e.g., laser beam) having energy packets with pulsed energies (per packet) of about 10 $\mu$J The energy source 1200 (e.g., laser) may provide energy (e.g., laser beam) having energy packets with pulsed energies (per packet) of about 20 $\mu$J The energy source 1200 (e.g., laser) may provide energy (e.g., laser beam) having energy packets with pulsed energies (per packet) of about 30 $\mu$J The energy source 1200 (e.g., laser) may provide energy (e.g., laser beam) having energy packets with pulsed energies (per packet) of about 40 $\mu$J The energy source 1200 (e.g., laser) may provide energy (e.g., laser beam) having energy packets with pulsed energies (per packet) of about 50 $\mu$J The energy source 1200 (e.g., laser) may provide energy (e.g., laser beam) having energy packets with pulsed energies (per packet) of about 60 $\mu$J The energy source 1200 (e.g., laser) may provide energy (e.g., laser beam) having energy packets with pulsed energies (per packet) of about 70 $\mu$J The energy source 1200 (e.g., laser) may provide energy (e.g., laser beam) having energy packets with pulsed energies (per packet) of about 80 $\mu$J The energy source 1200 (e.g., laser) may provide energy (e.g., laser beam) having energy packets with pulsed energies (per packet) of about 90 $\mu$J The energy source 1200 (e.g., laser) may provide energy (e.g., laser beam) having energy packets with pulsed energies (per packet) of about 100 $\mu$J The energy source 1200 (e.g., laser) may provide energy (e.g., laser beam) having energy packets with pulsed energies (per packet) of about 110 $\mu$J The energy source 1200 (e.g., laser) may provide energy (e.g., laser beam) having energy packets with pulsed energies (per packet) of about 120 $\mu$J. The energy source 1200 (e.g., laser) may provide energy (e.g., laser beam) having energy packets with pulsed energies (per packet) of about 130 $\mu$J. The energy source 1200 (e.g., laser) may provide energy (e.g., laser beam) having energy packets with pulsed energies (per packet) of about 140 $\mu$J. The energy source 1200 (e.g., laser) may provide energy (e.g., laser beam) having energy packets with pulsed energies (per packet) of about 150 $\mu$J The energy source 1200 (e.g., laser) may provide energy (e.g., laser beam) having energy packets with pulsed energies (per packet) of about 160 µJ. The energy source 1200 (e.g., laser) may provide energy (e.g., laser beam) having energy packets with pulsed energies (per packet) of about 170 µJ The energy source 1200 (e.g., laser) may provide energy (e.g., laser beam) having energy packets with pulsed energies (per packet) of about 180 µJ The energy source 1200 (e.g., laser) may provide energy (e.g., laser beam) having energy packets with pulsed energies (per packet) of about 190 µJ The energy source 1200 (e.g., laser) may provide energy (e.g., laser beam) having energy packets with pulsed energies (per packet) of about 200 µJ The energy source 1200 (e.g., laser) may provide energy (e.g., laser beam) having energy packets with pulsed energies (per packet) of about 20,000 µJ. The energy source 1200 (e.g., laser) may provide energy (e.g., laser beam) having energy packets with pulsed energies (per packet) of about 100,000 µJ The energy source 1200 (e.g., laser) may provide energy (e.g., laser beam) having energy packets with pulsed energies (per packet).

The energy source 1200 (e.g., laser) may provide energy (e.g., laser beam) having a wavelength from e.g. about at least 300 nm to about 5 mm or more. The energy source 1200 (e.g., laser) may provide energy (e.g., laser beam) having a wavelength of at least 600 to about 1500 nm or more. The energy source 1200 (e.g., laser) may provide energy (e.g., laser beam) having a wavelength from about at least 350 nm to about 1800 nm or more. The energy source 1200 (e.g., laser) may provide energy (e.g., laser beam) having a wavelength from about at least 1800 nm to about 5 mm or more. The energy source 1200 (e.g., laser) may provide energy (e.g., laser beam) having a wavelength of about 300 nm. The energy source 1200 (e.g., laser) may provide energy (e.g., laser beam) having a wavelength of about 400 nm. The energy source 1200 (e.g., laser) may provide energy (e.g., laser beam) having a wavelength of about 600 nm. The energy source 1200 (e.g., laser) may provide energy (e.g., laser beam) having a wavelength of about 700 nm. The energy source 1200 (e.g., laser) may provide energy (e.g., laser beam) having a wavelength of about 800 nm. The energy source 1200 (e.g., laser) may provide energy (e.g., laser beam) having a wavelength of about 900 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1300 nm. The energy source 1200 (e.g., laser) may provide energy (e.g., laser beam) having a wavelength of about 1400 nm. The energy source 1200 (e.g., laser) may provide energy (e.g., laser beam) having a wavelength of about 1500 nm. The energy source 1200 (e.g., laser) may provide energy (e.g., laser beam) having a wavelength of about 1600 nm. The energy source 1200 (e.g., laser) may provide energy (e.g., laser beam) having a wavelength of about 1700 nm. The energy source 1200 (e.g., laser) may provide energy (e.g., laser beam) having a wavelength of about 1800 nm. The energy source 1200 (e.g., laser) may provide energy (e.g., laser beam) having a wavelength of about 1900 nm. The energy source 1200 (e.g., laser) may provide energy (e.g., laser beam) having a wavelength of about 2000 nm. The energy source 1200 (e.g., laser) may provide energy (e.g., laser beam) having a wavelength of about 3000 nm. The energy source 1200 (e.g., laser) may provide energy (e.g., laser beam) having a wavelength of about 4000 nm. The energy source 1200 (e.g., laser) may provide energy (e.g., laser beam) having a wavelength of about 5000 nm.

As shown in FIG. 14, the energy source 1200 may project a laser beam 1202 through a shutter 1104. Once the laser beam 1202 exits the shutter 1204, the laser beam 1202 may be directed through a rotating half-wave plate 1206. The rotating half-wave plate 1206 may alter the polarization state of the laser beam 1202 such that the difference in phase delay between the two linear polarization directions is π. The difference in phase delay may correspond to a propagation phase shift over a distance of λ/2. Other types of wave plates may be utilized with the system disclosed herein; for example, a rotating quarter-wave plate may be used. The rotating half-wave plate 1206 may be a true zero-order wave plate, a low order wave plate, or a multiple-order wave plate. The rotating half-wave plate 1206 may be composed of crystalline quartz ($SiO_2$), calcite ($CaCO_3$), magnesium fluoride ($MgF_2$), sapphire ($Al_2O_3$), mica, or a birefringent polymer.

The laser beam 1202 may exit the rotating half-wave plate 1206 and may be directed through a polarizing beam splitter 1208. The polarizing beam splitter 1208 may split the laser beam 1202 into a first laser beam 1202*a* and a second laser beam 1202*b*. The first laser beam 1202*a* may be directed to a beam dump 1210. The beam dump 1210 is an optical element that may be used to absorb stray portions of a laser beam. The beam dump 1210 may absorb the first laser beam 1202*a*. The first laser beam 1202*a* may be a stray laser beam. The beam dump 1210 may absorb the second laser beam 1202*b*. The second laser beam 1202*b* may be a stray laser beam. The laser beam 1202 may be directed into the beam dump 1210 in its entirety and thus, may serve as a default "off" state of the printing system. The second laser beam 1202*b* may be directed to a beam expander 1212. The beam expander 1212 may expand the size of the second laser beam 1202*b*. The beam expander 1212 may increase the diameter of the input, second laser beam 1202*b* to a larger diameter of an output, expanded laser beam 1254. The beam expander 1212 may be a prismatic beam expander. The beam expander 1212 may be a telescopic beam expander. The beam expander 1212 may be a multi-prism beam expander. The beam expander 1212 may be a Galilean beam expander. The beam expander 1212 may provide a beam expander power of about 2×, 3×, 5×, 10×, 20×, or 40×. The beam expander 1212 may provide a beam expander power ranging from about 2× to about 5×. The beam expander 1212 may provide continuous beam expansion between about 2× and about 5×. The beam expander 1212 may provide a beam expander power ranging from about 5× to about 10×. The beam expander 1212 may provide continuous beam expansion between about 5× and about 10×. The expanded laser beam 1254 may be collimated upon exiting the beam expander 1212.

After exiting the beam expander 1212, the expanded laser beam 1254 may be directed to a first mirror 1214*a*, which may re-direct the expanded laser beam 1254 to a first spatial light modulator (SLM) 1216*a*. After exiting the first SLM 1216, the expanded laser beam 1254 may be directed to an f1 lens 1218. The f1 lens 1218 may be a focusing lens. After exiting the f1 lens, the expanded laser beam 1254 may be directed to a mirror with blocking element 1250. The mirror with blocking element 1250 may be used to suppress illumination from a zero-order spot.

Once the expanded laser beam 1254 is reflected by the mirror with blocking element 1250, the expanded laser beam 1254 may be transmitted through an f2 lens 1222. The f2 lens 1222 may be a focusing lens. After exiting the f2 lens 1222, the expanded laser beam 1254 may be directed to a second SLM 1216*b*. The SLMs (i.e., the first SLM 1216*a* and the second SLM 1216*b*) may be controlled by a computer system 1101. The SLMs may perform all of the functions, as described supra, of the SLM 1016 and the SLM 1116, as presented in FIGS. 44 and 45, respectively.

After exiting the second SLM 1216*b*, the expanded laser beam 1254 may be directed to an f3 lens 1228. After exiting the f3 lens, the expanded laser beam 1254 may be directed to blocking element 1220. The blocking element 1220 may be immovable. The blocking element 1220 may be used to suppress illumination from a zero-order spot. After exiting the blocking element 1220, the expanded energy beam 1254 may be directed through an f4 lens 1238. The f4 lens 1238 may be a focusing lens. After exiting the f4 lens 1238, the expanded laser beam 1254 may be directed onto a second mirror 1214*b* and may be subsequently directed onto a third mirror 1214*c*. The third mirror 1214*c* may re-direct the expanded laser beam 1254 through a long pass dichroic mirror 1224. The first mirror 1214*a*, the second mirror 1214*b*, and/or the third mirror 1214*c* may be controlled with a computer system 1101. The computer system 1101 may turn the first mirror 1214*a*, the second mirror 1214*b*, and/or the third mirror 1214*c* "on" or "off" in order to re-direct the expanded laser beam 1254 as desired. The dichroic mirror may be a short pass dichroic mirror. The long pass dichroic mirror 1224 may reflect the expanded laser beam 1254 into the focusing objective 1232. In some instances, a beam combiner may be used to re-direct the expanded laser beam 1254 into the focusing objective 1232 instead of using the long pass dichroic mirror 1224. The long pass dichroic mirror 1224 may be controlled with a computer system 1101 to re-direct the expanded laser beam 1254 into the focusing objective 1232. The focusing objective 1232 may concentrate the expanded laser beam 1254 as it is projected into the printing chamber 1234. The printing chamber 1234 may be a media chamber 122. The printing chamber 1234 may comprise a cell-containing medium, a plurality of cells, cell constituents (e.g., organelles), and/or at least one polymer precursor.

The printing chamber 1234 may be mounted on a movable stage 1246. The movable stage 1246 may be an xy stage, a z stage, and/or an xyz stage. The movable stage 1246 may be manually positioned. The movable stage 1246 may be automatically positioned. The movable stage 1246 may be a motorized stage. The movable stage 1246 may be controlled by the computer system 1101. The computer system 1101 may control the movement of the movable stage 1246 in the x, y, and/or z directions. The computer system 1101 may automatically position the movable stage 1246 in a desired x, y, and/or z position. The computer system 1101 may position the movable stage 1246 in a desired x, y, and/or z position with a positional accuracy of at most about 3 µm. The computer system 1101 may position the movable stage 1246 in a desired x, y, and/or z position with a positional accuracy of at most about 2 µm. The computer system 1101 may position the movable stage 1246 in a desired x, y, and/or z position with a positional accuracy of at most about 1 µm. The computer system 1101 may automatically adjust the position of the movable stage 1246 prior or during three-dimensional printing. The computer system 1101 may comprise a piezo controller to provide computer-controlled z-axis (i.e., vertical direction) positioning and active location feedback. The computer system 1101 may comprise a joystick console to enable a user to control a position of the movable stage 1246. The joystick console may be a z-axis console and/or an x-axis and y-axis console. The movable stage 1246 may comprise a printing chamber holder. The printing chamber holder may be a bracket, a clip, and/or a recessed sample holder. The movable stage 1246 may comprise a multi-slide holder, a slide holder, and/or a petri dish holder. The movable stage 1246 may comprise a sensor to provide location feedback. The sensor may be a capacitive sensor. The sensor may be a piezoresistive sensor. The movable stage 1246 may comprise at least one actuator (e.g., piezoelectric actuator) that moves (or positions) the movable stage 1246.

A light-emitting diode (LED) collimator 1240 may be used as a source of collimated LED light 1256. The LED collimator 1240 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1240 may project a beam of collimated LED light 1256 through an f6 lens 1248. The f6 lens 1248 may be a focusing lens. Once the collimated LED light 1256 is transmitted through the f6 lens 1248, the collimated LED light 1156 may be directed into a light focusing objective 1236. The light focusing objective 1236 may focus the collimated LED light 1256 into the printing chamber 1234. The light focusing objective 1236 may focus the collimated LED light 1256 in the sample medium. The light focusing objective 1236 may focus the collimated LED light 1256 in the cell-containing medium. The collimated LED light 1256 may be transmitted through the printing chamber 1234 and into the focusing objective 1232. Once the collimated LED light 1256 exits the focusing objective 1232, the collimated LED light 1256 may be directed onto the long pass dichroic mirror 1224. The collimated LED light 1256 that is reflected off of the long pass dichroic mirror 1224 may be the sample emission 1226. The long pass dichroic mirror 1224 may re-direct the sample emission 1226 into an f5 lens 1244. The f5 lens may be a focusing lens. Once sample emission 1226 is transmitted through the f5 lens 1244, a detection system 1230 detects and/or collects the sample emission 1226 for imaging. The detection system 1230 may comprise at least one photomultiplier tube (PMT). The detection system 1230 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1230 may comprise at least one array-based detector.

Figure 15:
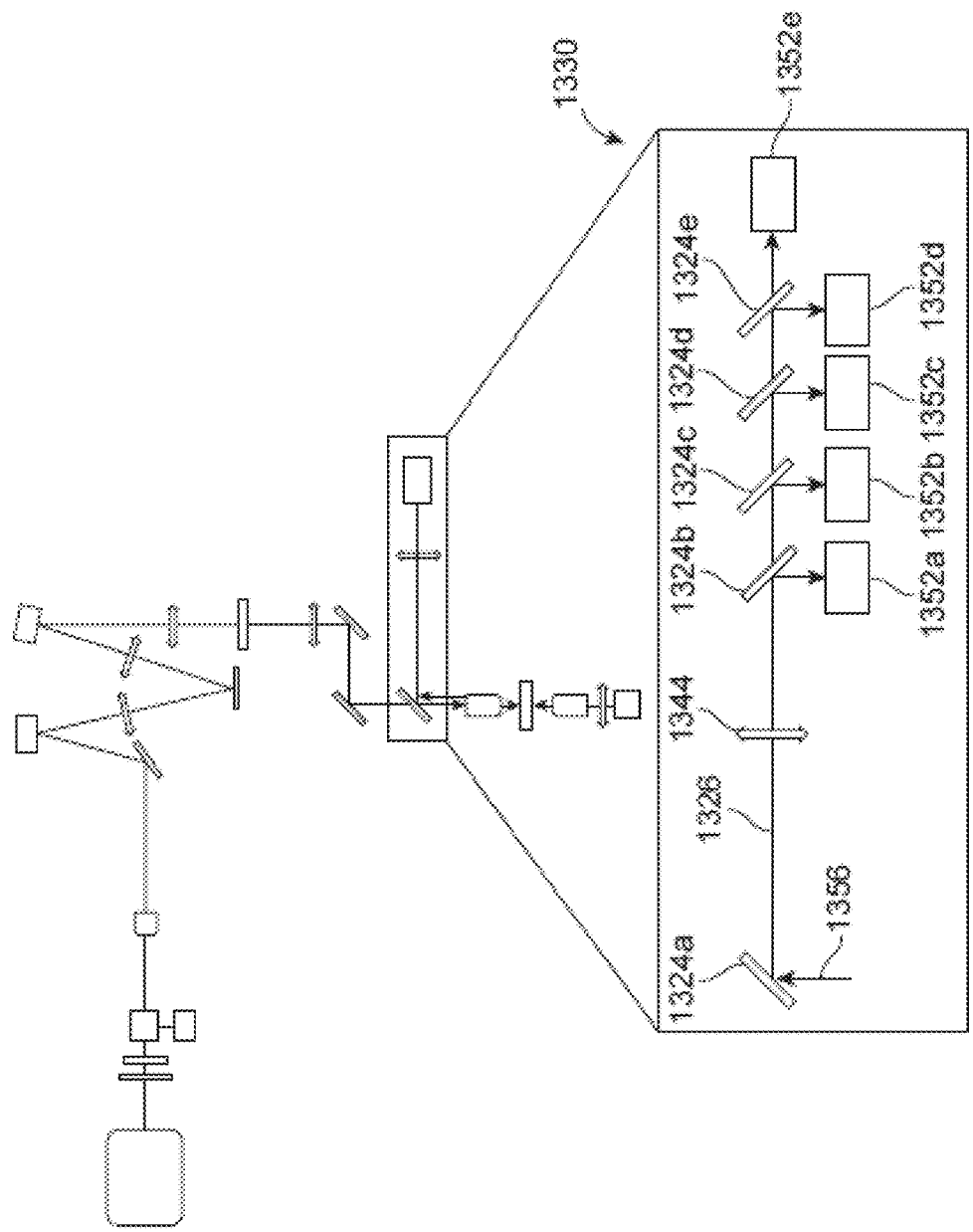
FIG. 15 illustrates a light detection system.
Figure 16:
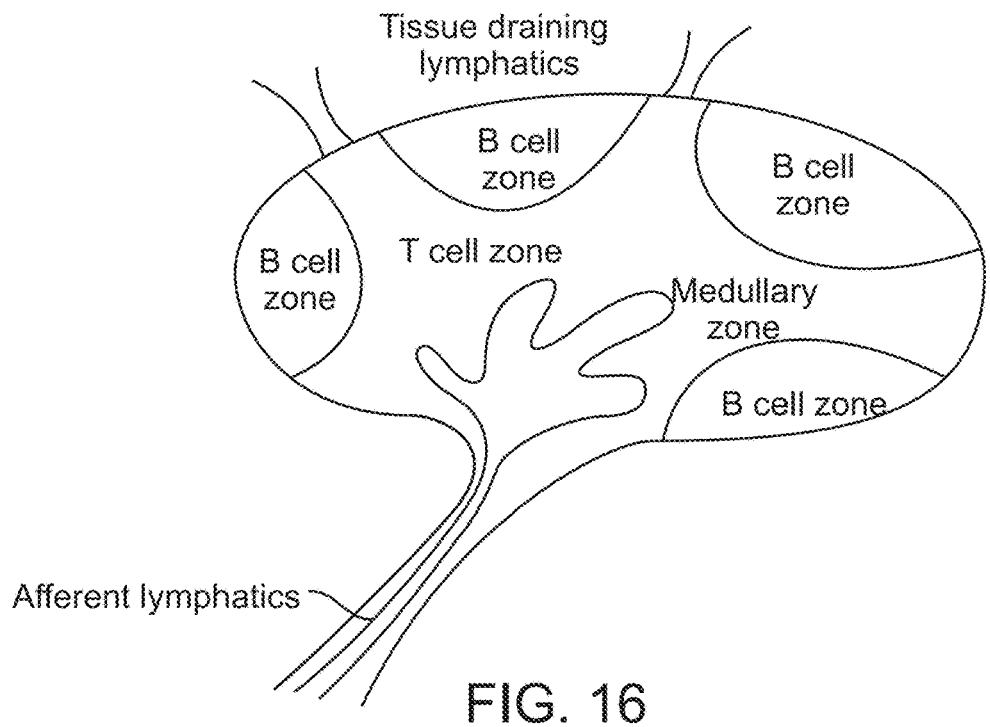
FIG. 16 illustrates the compartmentalization and organization of several types of lymphocytes in a lymph node, additionally depicted in a cross-section with major structures and cell types labeled.

FIG. 15 illustrates a light detection system 1330. The light detection system 1330 may comprise a plurality of long pass dichroic mirrors arranged in series. The light detection system 1330 may comprise a plurality of long pass dichroic mirrors arranged in parallel. The light detection system 1330 may comprise a plurality of long pass dichroic mirrors arranged in series and parallel. As shown in FIGS. 44-46, the optical paths may comprise an LED collimator that projects a beam of collimated LED light 1356 onto the focusing objectives. Once the collimated LED light 1356 is reflected from the first long pass dichroic mirror 1324*a*, the collimated LED light 1356 may be converted to a sample emission 1326. The sample emission 1326 may be directed through an f5 lens 1344. The f5 lens 1344 may be a focusing lens. After the sample emission 1326 exits the f5 lens 1344, the sample emission 1326 may be directed to a series of long pass dichroic mirrors comprising a second long pass dichroic mirror 1324b, a third long pass dichroic mirror 1324c, a fourth long pass dichroic mirror 1324d, and a fifth long pass dichroic mirror 1324e, as shown in FIG. 15. The sample emission 1326 may be reflected off of the second long pass dichroic mirror 1324b and onto a first light detector 1352a. The sample emission 1326 may be reflected off of the third long pass dichroic mirror 1324c and onto a second light detector 1352b. The sample emission 1326 may be reflected off of the fourth long pass dichroic mirror 1324d and onto a third light detector 1352c. The sample emission 1326 may be reflected off of the fifth long pass dichroic mirror 1324e and onto a fourth light detector 1352d. The sample emission 1326 may be reflected off of the fifth long pass dichroic mirror 1324e and onto a fifth light detector 1352e. The light detector may be a photomultiplier tube (PMT). The light detector may be a camera. The light detector may be a complementary metal-oxide semiconductor (CMOS) camera, a scientific CMOS camera, a charge-coupled device (CCD) camera, or an electron-multiplying charge-coupled device (EM-CCD). The light detector may be an array-based detector. The light detection system 1330 may comprise a plurality of long pass dichroic mirrors that have progressively red-shifted cutoff wavelengths. In some instances, the second long pass dichroic mirror 1324b may have a cutoff wavelength of about 460 nm, the third long pass dichroic mirror 1324c may have a cutoff wavelength of about 500 nm, the fourth long pass dichroic mirror 1324d may have a cutoff wavelength of about 540 nm, the fifth long pass dichroic mirror 1324e may have a cutoff wavelength of about 570 nm.

The light detection system 1330 may be controlled by the computer system 1101. The computer system 1101 may collect and/or process the signals obtained by the first light detector 1352a, the second light detector 1352b, the third light detector 1352c, and the fourth light detector 1352d. The computer system 1101 may provide control feedback to the three-dimensional printing system based on the light detector signals, of the light detection system 1330, which may be collected and/or processed by the computer system 1101. The computer system 1101 may have control feedback over any optical component and/or hardware of the optical paths described in FIGS. 44-46. The computer system 1101 may have control feedback over any optical component and/or hardware of the light detection system 1330 shown in FIG. 15. The computer system 1101 may control, for example, an SLM, a shutter, a movable stage, a mirror, a lens, a focusing objective, a beam expander, an LED collimator, a grating, and/or a blocking element in response to a signal from the light detection system 1330.

Figure 5A:
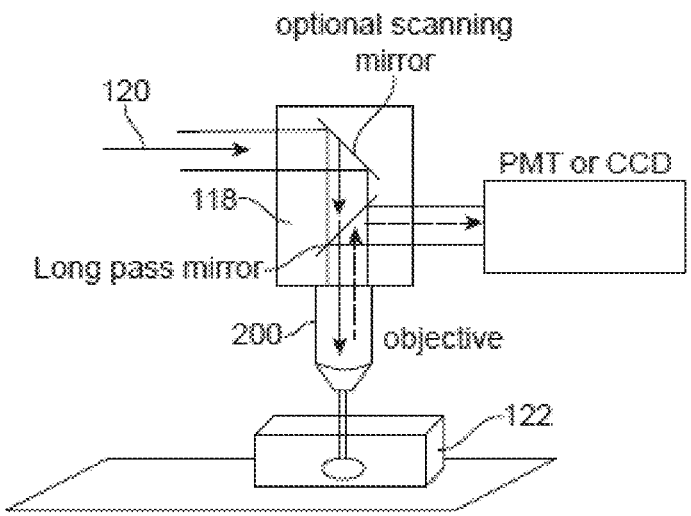
FIGS. 5A-5B illustrate various embodiments of the multi-photon tissue print head.

FIG. 5A illustrates an embodiment of the multi-photon tissue print head 118. The multi-photon print-head 118 may receive the multi-photon laser beam 120 (comprising one or more wavelengths) from the laser system 116 and may focus the beam 120 through the final optical path with is comprised of finishing optics that are comprised of an optional scan head, long pass mirror for use collection and recording of back-scatter light and a focusing objective 200, projecting the beam 120 into the media chamber 122. The light may be collected by the same objective as used to print, and then shunted via a long-pass mirror to the single or bank of PMTs, or a CCD camera.

In some designs, the optics may send the laser through a fiber optic cable for easier control of where the light is deposited in the tissue printing vessel.

The systems disclosed herein can utilize a range of focusing objectives, for example, with an increasingly lower magnification; the field of view may be increasingly larger. In some cases, the field of view may be the print area that the microscope is capable of, in a single projection area. In some cases, 5×, 10×, or 20× objectives may be employed. In some cases, objectives with high numerical apertures ranging between at least about 0.6 and about 1.2 or more may be employed. The systems disclosed herein may use an objective lens with a magnification ranging from e.g., about 1× to about 100×. The systems disclosed herein may use an objective lens with a magnification of about 1×. The systems disclosed herein may use an objective lens with a magnification of about 2×. The systems disclosed herein may use an objective lens with a magnification of about 3×. The systems disclosed herein may use an objective lens with a magnification of about 4×. The systems disclosed herein may use an objective lens with a magnification of about 10×. The systems disclosed herein may use an objective lens with a magnification of about 20×. The systems disclosed herein may use an objective lens with a magnification of about 40×. The systems disclosed herein may use an objective lens with a magnification of about 60×. The systems disclosed herein may use an objective lens with a magnification of about 100×.

To maintain structural fidelity of the printed tissues, a water-immersion objective lens may be ideal so as to substantially match the angle of incidence within the cell-containing liquid biogel media 126. A water-immersion objective lens corrected for refractive index changes may be used as printing takes place in liquid media which has a significantly different refractive index from air.

Figure 5B:
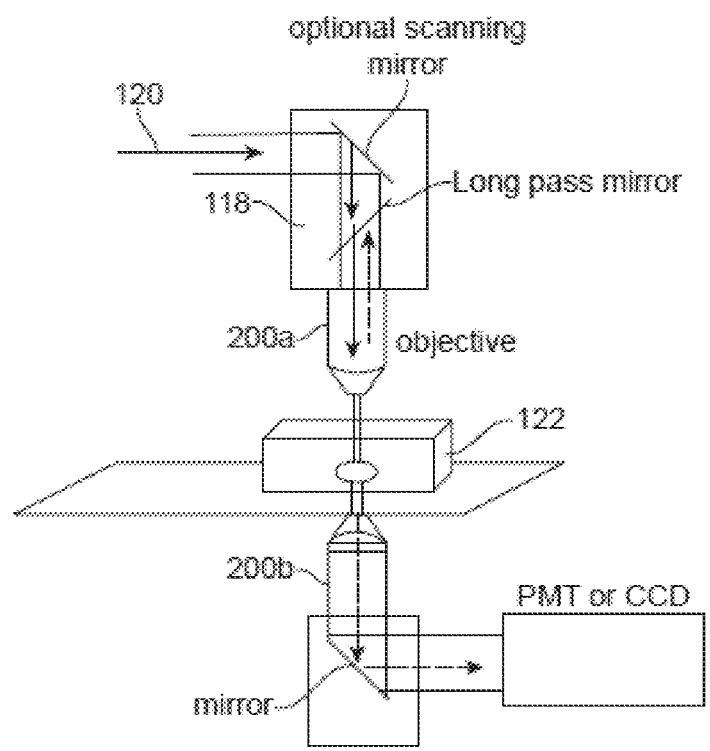

FIG. 5B illustrates a print head 118 comprising a first objective lens 200a and a second objective lens 200b. FIG. 5B illustrates inverted optics for imaging structures. In this embodiment, light may be collected by inverted optics and channeled to a CCD camera, a single PMT, as shown in FIG. 5B, or a bank of PMTs to create a multi-color image. In some embodiments, a second objective head may be inverted and images may be collected from the underside of the tissue and incident light read by PMTs with a series of long pass or band-pass mirrors.

In order for a multi-photon based printer to switch from a printing mode to an imaging mode, x, y raster scanning may be engaged and the DMD or SLM paths may be bypassed or the devices rendered in an off or inactive position, or removing them from the light path such that there is only a single laser line hitting the x, y scanning optics. DMD or SLM paths may also in some instances be used for imaging.

Switching to imaging mode may have several uses during the printing process: 1) imaging can be used to monitor collagen generation rates as collagen naturally produces an emission via second harmonic generation, which is a process when two-photon excitation is scanned across the structures, 2) the edges of printed tissues can be found using imaging mode facilitating the proper linking of blood vessels and other tissue structures along edges of projection spaces, 3) printed tissue structures can be validated for structural integrity and fidelity to the projected images in real-time, and 4) if cells that are temporarily labeled are used, they can be located within the printed tissues for process validation or monitoring. It may be appreciated that the laser system 116 of the above embodiments may have a variety of points of software control including, but not limited to: The CAD images may be projected by programing changes that are hardwired to the SLM and/or DMD devices; If TAG lenses are used to create a Bessel beam, the current generated to induce the tunable acoustic gradient (TAG) in the TAG lens may be under the control of computer software; The mirrors that direct the laser excitation in the single beam incarnation and may act as an off/on switch for the multi-laser design may be controlled by computer software; The laser intensity via an attenuation wheel and tuning to different frequencies may be controlled by software input; Microscope stage movement may be under software control; Movement of microscope objective or associated fiber optics may be under software control; Edge finding, illumination, and control of the inverted objective by movement or on/off status may be under software control; any imaging or light path controls (mirrors, shutters, scanning optics, SLMs, DMD etc.) may be under control of software.

Figure 6A:
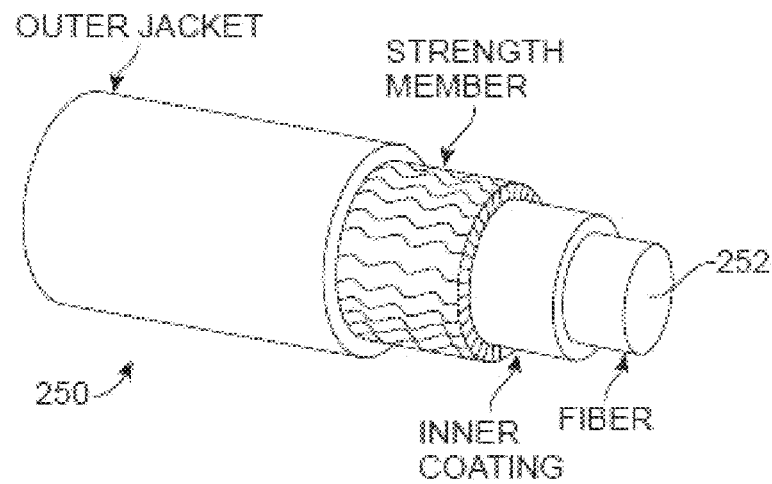
FIGS. 6A-6B illustrate embodiments of a removable and attachable fiber optic cable accessory.
Figure 6B:
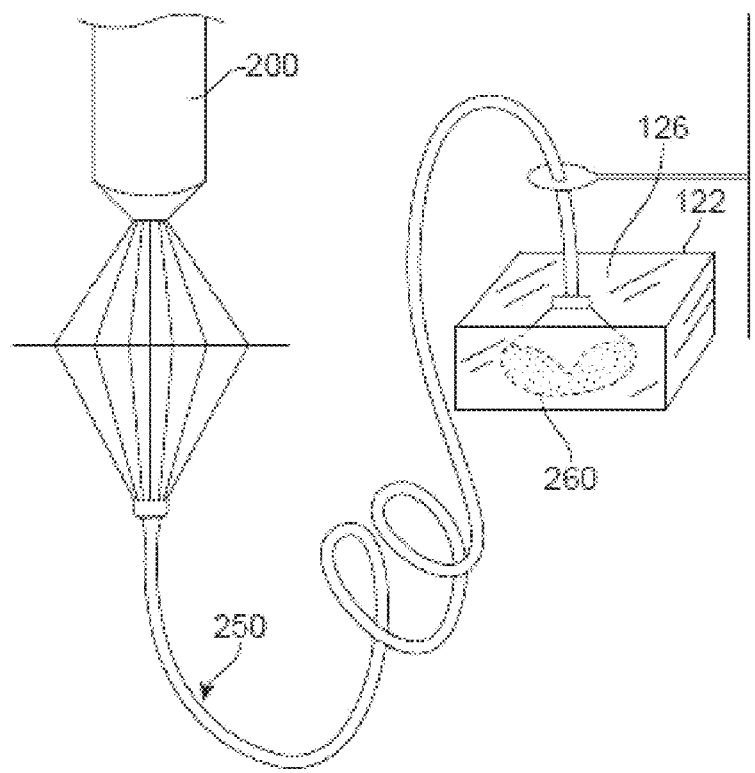

To accommodate rapid printing, the objective 200 may be equipped with a fiber optic cable. FIG. 6A illustrates an embodiment of a removable and attachable fiber optic cable accessory 250. In this embodiment, the accessory 250 may comprise a fiber optic cable 252 and a fitting (not shown in FIGS. 6A-6B) which is attachable to the multi-photon tissue printing print-head (not shown in 6A-6B). The fiber optic cable 252 can then be positioned within the media 126 of the media chamber 122, as illustrated in FIG. 6B. Thus, the multi-photon laser beam 120 may pass through the objective 200 and the fiber optic cable 252 to deliver the laser energy to the media 126, creating the desired complex tissue structure 260. To avoid moving the microscope objective during the printing process or the printing vessel that contains delicate tissue structures, the fiber optic cable itself may be moved if larger regions of tissue need to be printed. In some cases, the accessory 250 can be sterilized or replaced so that direct insertion into the media 126 does not compromise sterility or cross-contaminate printed cells.

Depending upon the power input into the fiber optic cable, multi-photon lasers may be capable of inducing irreversible damage to the core of the fiber optic cable. Thus, in some cases, induced wavelength chirping by group delayed dispersion (GDD) may be provided to minimize this potential damage, by effectively dispersing the photons to elongate the laser pulse. This may be used to either minimize damage to cells in the print media or to extend the life of fiber optic cables. In such instances, a GDD device may be provided in the laser system 116 after the SLM or DMD and before entry to the print-head optics 118.

In some cases, three-dimensional printing of the desired tissue may be carried out with a single objective 200 or an objective 200 with an attached fiber optic accessory 250, wherein the one to three different configurations, each associated with a distinct laser line and representing a distinct shape or portion of the tissue may be pulsed though the same objective 200. In such cases, a timed shutter system may be installed such that there is no or minimal interference between images being projected. Thus, laser multiplexing may be employed to allow generation of portions of the tissue structure simultaneously at multiple points while utilizing the same CAD model of the tissue structure. Likewise, the laser multiplexing may utilize different but contiguous CAD based tissue models, minimizing the movement needed for larger structure printing while decreasing overall print time further. For example, a vascular bed may have internal structures such as valves in the larger blood vessels that prevent venous back flow in normal circulation. These valve structures may be printed simultaneously with the blood vessel walls. In such a case, the scaffolding associated with the valve structure and/or blood vessel walls may be difficult to print separately.

The instantaneously formed three-dimensional structure may be repeated throughout the print space during one round of printing. In biological systems, small units may often be repeated throughout the structure. Therefore, repeated generation of a same structure in one print round may be useful for generating functional tissues. Additional, non-repetitive, fine featured structures and subsequent structures from the same cell-print material may be created that line-up with or link to the first structure printed.

Figure 7:
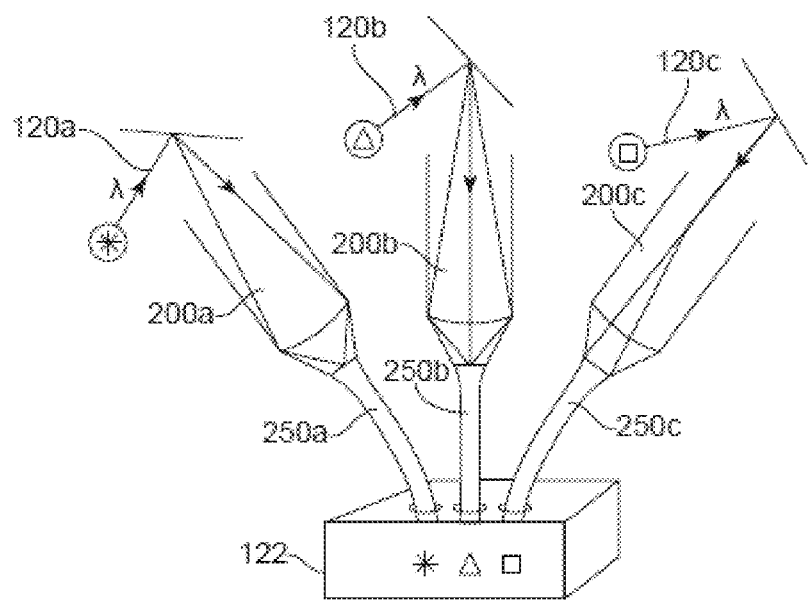
FIG. 7 illustrates an embodiment wherein the print-head optics includes at least three objectives, wherein each objective includes a fiber optic cable accessory directed into a single media chamber.
Figure 8:
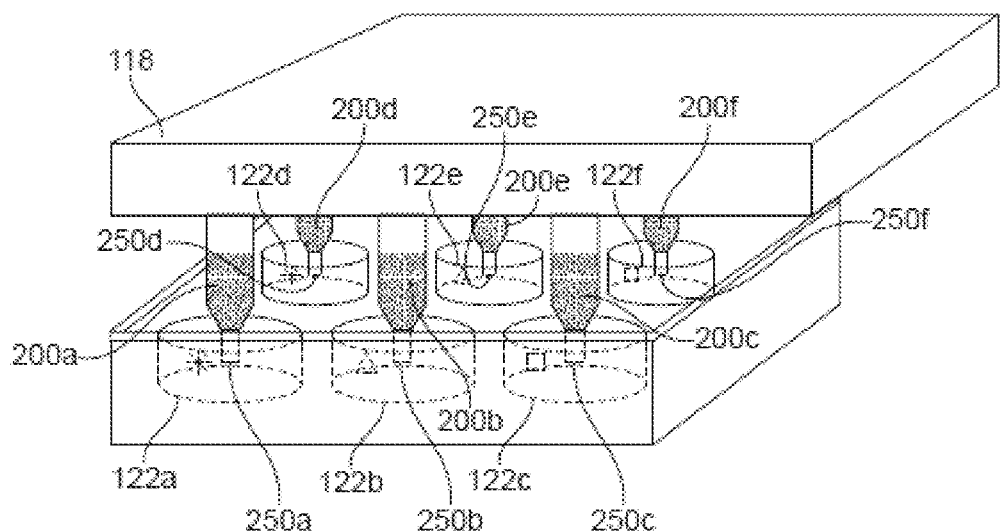
FIG. 8 illustrates an embodiment wherein the print-head optics includes at least six objectives, wherein each objective includes a fiber optic cable accessory directed into a separate media chamber such as a separate well of a multi-well plate.

In some embodiments, the multi-photon tissue printing print-head 118 may include multiple printing "heads" or sources of multi-photon excitation via a first laser objective 200a, a second laser objective 200b, and a third laser objective 200c as illustrated in FIGS. 7-8. FIG. 7 illustrates an embodiment wherein the multi-photon tissue printing print-head 118 may include a first laser objective 200a, a second laser objective 200b, and a third laser objective 200c, wherein the first laser objective 200a may include a first fiber optic cable accessory 250a, the second laser objective 200b may include a second fiber optic cable accessory 250b, and the third laser objective 200c may include a third fiber optic cable accessory 250c. The first fiber optic cable accessory 250a, the second fiber optic cable accessory 250b, and the third fiber optic cable accessory 250c may be directed into a single media chamber 122. The media chamber 122 may have an open top or a sealed top with port access by each accessory fiber optic cable accessory (i.e., via the first fiber optic cable accessory 250a, the second fiber optic cable accessory 250b, and the third fiber optic cable accessory 250c). This arrangement may increase the speed of large, rapid tissue printing, while maintaining control over the final tissue structure. In some cases, the first fiber optic cable accessory 250a, the second fiber optic cable accessory 250b, and the third fiber optic cable accessory 250c may deliver a projection of the same tissue structure. In other cases, each the first fiber optic cable accessory 250a, the second fiber optic cable accessory 250b, and the third fiber optic cable accessory 250c may deliver a first laser beam projection 120a, a second laser beam projection 120b, and a third laser beam projection 120c, respectively, of a different tissue structure. Given the flexible arrangement of the multiple laser objectives and the ability of directing the fiber optic cables into the same area within the media chamber 122, the tissue structures may be simultaneously printed. The resulting tissue structures may be linked or not linked together. The print time of a given tissue structure may have an inverse relationship to the number of laser delivery elements with some consideration for the movement restrictions and considerations to be accounted for with each additional excitation source.

FIG. 8 illustrates an embodiment wherein the multi-photon tissue printing print-head 118 may include a first objective 200a, a second objective 200b, a third objective 200c, a fourth objective 200d, a fifth objective 200e, and a sixth objective 200f, wherein each objective may include a first fiber optic cable accessory 250a, a second fiber optic cable accessory 250b, a third fiber optic cable accessory 250c, a fourth fiber optic cable accessory 250d, a fifth fiber optic cable accessory 250e, and a sixth fiber optic cable accessory 250f, respectively, directed into a separate first media chamber 122a, a second media chamber 122b, a third media chamber 122c, a fourth media chamber 122d, a fifth media chamber 122e, and a sixth media chamber 122f, respectively. The plurality of media chambers may be a multi-well plate, wherein each well of the multi-well plate is a separate, individual media chamber. In some cases, the first fiber optic cable accessory 250a, the second fiber optic cable accessory 250b, the third fiber optic cable accessory 250c, the fourth fiber optic cable accessory 250d, the fifth fiber optic cable accessory 250e, and the sixth fiber optic cable accessory 250f may deliver at least one projection of the same tissue structure. This provides multiple copies of the tissue structure simultaneously. In other cases, the first fiber optic cable accessory 250a, the second fiber optic cable accessory 250b, the third fiber optic cable accessory 250c, the fourth fiber optic cable accessory 250d, the fifth fiber optic cable accessory 250e, and the sixth fiber optic cable accessory 250f may deliver a first multi-photon laser beam projection 120a, a second multi-photon laser beam projection 120b, and a third multi-photon laser beam projection 120c of a different tissue structure. In some cases, the print time may be greatly reduced due to the ability of producing multiple copies simultaneously.

Figure 9:
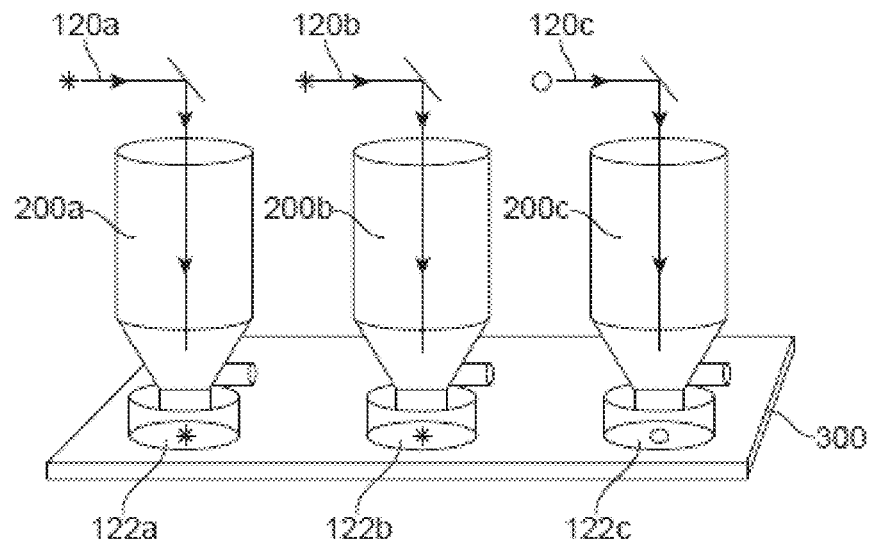
FIG. 9 illustrates embodiments of print-head optics having an array of objectives acting as print heads.
Figure 10:
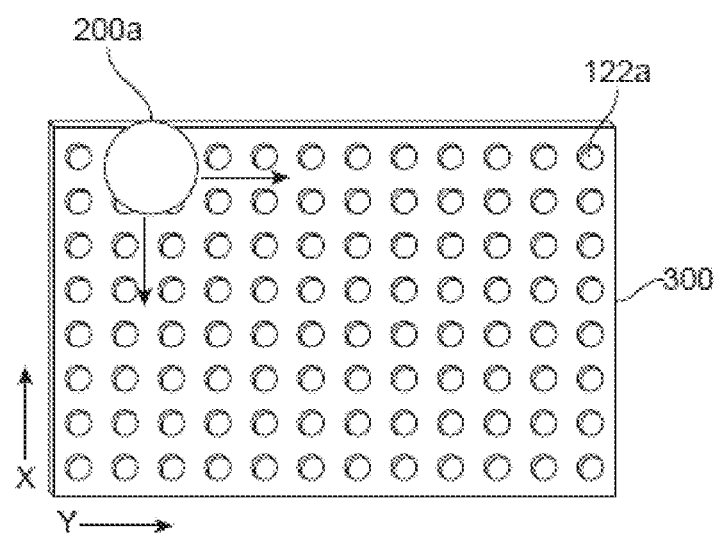
FIG. 10 illustrates objectives programmed to move over the multi-well plate in X and Y directions to deliver the laser beam projections into each well.

In some embodiments, the multi-photon tissue printing print-head 118 may include a serial array of objectives comprising a first objective 200a, a second objective 200b, and a third objective 200c, as illustrated in FIG. 9. In this embodiment, each objective may be aligned with a separate media chamber. For example, the first objective 200a may be aligned with a first media chamber 122a, the second objective 200b may be aligned with a second media chamber 122b, the third objective 200c may be aligned with a third media chamber 122c. In some instances, the multiple media chambers may be wells of a multi-well plate 300. In some embodiments, the first objective 200a, the second objective 200b, and the third objective 200c may deliver projection of the same tissue structure. In other cases, the laser beam projections may differ per well. The first objective 200a, the second objective 200b (not shown in FIG. 10), and the third objective 200c (not shown in FIG. 10) may be programmed to move over the multi-well plate 300 in the x and y directions, as illustrated in FIG. 10, to deliver the laser beam projections into each well. Alternatively, it may be appreciated that the objectives may remain stationary while the multi-well plate 300 moves in the x and y directions. Thus, for example, a serial array having three objectives can print tissue in a six well plate in two steps: three tissue structures simultaneously and then three more tissue structures simultaneously. It may be appreciated that plates having any number of wells may be used including, but not limited to at least about 96 wells to about 394 wells, or more. The multi-well plate 300 may comprise at least a first media chamber 122a. The multi-well plate 300 may comprise at least 1 well. The multi-well plate 300 may comprise at least 4 wells. The multi-well plate 300 may comprise at least 6 wells. The multi-well plate 300 may comprise at least 8 wells. The multi-well plate 300 may comprise at least 12 well. The multi-well plate 300 may comprise at least 16 wells. The multi-well plate 300 may comprise at least 24 wells. The multi-well plate 300 may comprise at least 48 wells. The multi-well plate 300 may comprise at least 96 wells. The multi-well plate 300 may comprise at least 384 wells. The multi-well plate 300 may comprise at least 1536 wells.

It may be appreciated that in the embodiments described herein, the microscope stage may be able to move, the microscope head may be able to move, and/or an associated fiber optic cable attached to the printing objective may be able to move in order to print larger spaces.

Methods of Printing Organs and Organoids

The present disclosure provides methods and systems for producing one or more immunological proteins. In an aspect, a method for producing one or more immunological proteins comprises providing a media chamber comprising a medium comprising: (i) a plurality of cells and (ii) one or more polymer precursors. Next, at least one energy beam may be directed to the medium in the media chamber along at least one energy beam path that is patterned into a three-dimensional (3D) projection in accordance with computer instructions for printing a 3D lymphoid organoid in computer memory. This may form at least a portion of the 3D lymphoid organoid comprising: (i) at least a subset of the plurality of cells, and (ii) a polymer formed from the one or more polymer precursors. Next, a method for producing one or more immunological proteins may comprise subjecting the at least one portion of the 3D lymphoid organoid to conditions sufficient to stimulate production of the one or more immunological proteins.

In another aspect, a method for producing one or more immunological proteins, comprises (i) printing a three-dimensional (3D) lymphoid organoid comprising a matrix containing a plurality of cells, and (ii) treating the 3D lymphoid organoid to produce the one or more immunological proteins.

In another aspect, a method for producing one or more immunological proteins, comprises: providing a media chamber comprising a first medium. The first medium may comprise a first plurality of cells and a first polymeric precursor. Next, at least one energy beam may be directed to the first medium in the media chamber along at least one energy beam path in accordance with computer instructions for printing a three-dimensional (3D) lymphoid organoid in computer memory, to subject at least a portion of the first medium in the media chamber to form a first portion of the 3D lymphoid organoid. Next, the method may provide a second medium in the media chamber. The second medium may comprise a second plurality of cells and a second polymeric precursor. The second plurality of cells may be of a different type than the first plurality of cells. Next, the method may comprise directing at least one energy beam to the second medium in the media chamber along at least one energy beam path in accordance with the computer instructions, to subject at least a portion of the second medium in the media chamber to form a second portion of the 3D lymphoid organoid. Next, the method may comprise subjecting the first and second portions of the 3D lymphoid organoid to conditions sufficient to stimulate production of the one or more immunological proteins.

In another aspect, a method of producing one or more immunological proteins comprises (i) printing a three-dimensional (3D) lymphoid organoid comprising a matrix containing a first plurality of cells and a second plurality of cells, and (ii) treating the 3D lymphoid organoid to produce the one or more immunological proteins.

Another aspect of the present disclosure provides a system for producing one or more immunological proteins, comprising a media chamber configured to contain a medium comprising a plurality of cells and one or more polymer precursors. The system may comprise at least one energy source configured to direct at least one energy beam to the media chamber. The system may comprise one or more computer processors operatively coupled to the at least one energy source. The one or more computer processors may be individually or collectively programmed to receive computer instructions for printing a three-dimensional (3D) lymphoid organoid from computer memory. The one or more computer processors may be individually or collectively programmed to direct the at least one energy source to direct the at least one energy beam to the medium in the media chamber along at least one energy beam path in accordance with the computer instructions, to subject at least a portion of the polymer precursors to form at least a portion of the 3D lymphoid organoid. The one or more computer processors may be individually or collectively programmed to subject the at least portion of the 3D lymphoid organoid to conditions sufficient to stimulate production of the one or more immunological proteins. The one or more computer processors may be individually or collectively further programmed to extract one or more immunological proteins from the at least portion of the 3D lymphoid organoid.

Another aspect of the present disclosure provides a method of producing a population of human immunological proteins, comprising: using a multi-photon laser bio-printing system to bio-print a three-dimensional lymphoid organoid. Next, the method may comprise exposing the three-dimensional lymphoid organoid to an antigen in order to stimulate production of the population of human immunological proteins. Next, the method may comprise extracting the population of human immunological proteins from the three-dimensional lymphoid organoid.

The conditions sufficient to stimulate production of the one or more immunological proteins may comprise exposing at least a portion of the 3D lymphoid organoid to an antigen in order to stimulate production of the one or more immunological proteins. The antigen may be selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. The antigen may be an exogenous antigen, an endogenous antigen, an autoantigen, a neoantigen, or a combination thereof. A neoantigen is defined herein as an antigen that is absent from a normal human genome. The neoantigen may be a tumor antigen, a viral antigen, an engineered antigen, or a synthetic antigen.

Methods of the present disclosure may further comprise extracting one or more immunological proteins from the at least portion of the 3D lymphoid organoid. The one or more immunological proteins may be human immunological proteins. The immunological proteins may be selected from the list consisting of antibodies, T-cell receptors, and cancer immunotherapeutics. The antibodies may be immunoglobulin G (IgG) antibodies. The IgG antibodies may be human IgG antibodies. The immunological proteins may be IgM, IgA, IgE, IgD antibodies or a combination thereof. The immunological proteins may be antibody fragments, antibody domains, immunoglobulin heavy chains, immunoglobulin light chains, or a combination thereof. The antibody fragments may be antigen-binding fragments (Fab), single chain variable fragments (scFv), or a combination thereof. The immunological proteins may be multivalent recombinant antibodies. The multivalent recombinant antibodies may be diabodies (i.e., small recombinant bispecific antibodies), minibodies (i.e., engineered antibody fragments), triabodies, tetrabodies, or a combination thereof. The immunological proteins may be engineered immunological proteins, synthetic immunological proteins, or a combination thereof. The synthetic immunological proteins may be nucleic acid aptamers, non-immunoglobulin protein scaffolds, non-immunoglobulin peptide aptamers, affimer proteins, or a combination thereof.

The plurality of cells may be from a subject. The plurality of cells may be autologous. The plurality of cells may be allogeneic. The plurality of cells may be selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. The B cells may be selected from the list consisting of naïve B cells, mature B cells, plasma B cells, B1 B cells, and B2 B cells. The T cells may be selected from the list consisting of CD8+ and CD4+.

The 3D lymphoid organoid may be selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ, and a secondary lymphoid organ. The shape of the 3D lymphoid organoid may be selected from the list consisting of spherical, oval, ovate, ovoid, square, rectangular, cuboid, any polygonal shape, free-form, and tear-drop shape. The shape of the 3D lymphoid organoid may be a tear-drop shape.

The polymer of the at least of the portion of 3D lymphoid organoid may form a network. The polymer may be collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or a combination thereof. The polymer may comprise an extracellular matrix component. Non-limiting examples of extracellular matrix components used to create 3D lymphoid organoids may include proteoglycans such as heparan sulfate, chondroitin sulfate, and keratan sulfate, non-proteoglycan polysaccharide such as hyaluronic acid, collagen, and elastin, fibronectin, laminin, nidogen, or any combination thereof. These extracellular matrix components may be functionalized with acrylate, diacrylate, methacrylate, cinnamoyl, coumarin, thymine, or other side-group or chemically reactive moiety to facilitate cross-linking induced directly by multi-photon excitation or by multi-photon excitation of one or more chemical doping agents. In some cases, photopolymerizable macromers and/or photopolymerizable monomers may be used in conjunction with the extracellular matrix components to create cell-containing structures. Non-limiting examples of photopolymerizable macromers may include polyethylene glycol (PEG) acrylate derivatives, PEG methacrylate derivatives, and polyvinyl alcohol (PVA) derivatives. In some instances, collagen used to create cell containing structure may be fibrillar collagen such as type I, II, III, V, and XI collagen, facit collagen such as type IX, XII, and XIV collagen, short chain collagen such as type VIII and X collagen, basement membrane collagen such as type IV collagen, type VI collagen, type VII collagen, type XIII collagen, or any combination thereof.

The polymer of the at least of the portion of 3D lymphoid organoid may contain other polymerizable monomers that are synthesized and not native to mammalian tissues, comprising a hybrid of biologic and synthetic materials. An example mixture may comprise about 0.4% w/v collagen methacrylate plus the addition of about 50% w/v polyethylene glycol diacrylate (PEGDA). Photoinitiators to induce polymerization may be reactive in the ultraviolet (UV), infrared (IR), or visible light range. Examples of two such photo initiators are Eosin Y (EY) and triethanolamine (TEA), that when combined may polymerize in response to exposure to visible light (e.g., wavelengths of about 390 to 700 nanometers). Non-limiting examples of photoinitiators may include azobisisobutyronitrile (AIBN), benzoin derivatives, benziketals, hydroxyalkylphenones, acetophenone derivatives, trimethylolpropane triacrylate (TPT), acryloyl chloride, benzoyl peroxide, camphorquinone, benzophenone, thioxanthones, and 2-hydroxy-1-[4-(hydroxyethoxy) phenyl]-2-methyl-1-propanone. Hydroxyalkylphenones may include 4-(2-hydroxyethylethoxy)-phenyl-(2-hydroxy-2-methyl propyl) ketone (Irgacure® 295), 1-hidroxycyclohexyl-1-phenyl ketone (Irgacure® 184) and 2,2-dimethoxy-2-phenylacetophenone (Irgacure® 651). Acetophenone derivatives may include 2,2-dimethoxy-2-phenylacetophenone (DMPA). Thioxanthones may include isopropyl thioxanthone.

The network, formed by the polymer, may be reticular, amorphous, or a net. The net may be an organized net. The organized net may comprise a repeated pattern. The network may be a structured network. The network may be an unstructured network. The network may be a hybrid grid wherein it comprises a mixture of structured and unstructured portions. The network may be a two-dimensional network. The network may be a three-dimensional network. The three-dimensional network may be a tetrahedron network, a pyramidal network, a hexahedron network, a polyhedron network, or a combination thereof. The network, formed by the polymer, may be a mesh. The mesh may be a triangular mesh, an octagonal mesh, a hexagonal mesh, a rectangular mesh, a square mesh, a diamond mesh, a circular mesh, or a combination thereof. The mesh may have varying sizes of each cell per unit area. The amorphous network may be designed to facilitate cellular interactions. The cellular interactions may be B cell to T cell conjugate formation, B cell to B cell interactions, B cell to macrophage, T cell to dendritic cell interactions, stromal cell interactions with T cells, stromal cell interactions with B cells, or stromal cell interactions with dendritic cells. The amorphous network may be designed to facilitate movement between or within cellular niches.

In an aspect, the present disclosure provides a method of printing an organ and/or an organoid. The method may comprise polymerization of a photopolymerizable material by a laser light source. The organ and/or the organoid may be two-dimensional or three-dimensional. The organ and/or the organoid may be a lymph node. The organoid may be an islet of Langerhans. The organoid may be a hair follicle. The organ and/or the organoid may be a tumor and/or a tumor spheroid. The organoid may be a neural bundle and support cells such as, but not limited to Schwann cells and glial cells including satellite cells, olfactory ensheathing cells, enteric glia, oligodendroglia, astroglia, and/or microglia. The organoid may be a nephron. The organoid may be a liver organoid. The organoid may be an intestinal crypt. The organ and/or the organoid may be a primary lymphoid organ, a secondary lymphoid organ such as a spleen, a liver, a pancreas, a gallbladder, an appendix, a brain, a small intestine, a large intestine, a heart, a lung, a bladder, a kidney, a bone, a cochlea, an ovary, a thymus, a trachea, a cornea, a heart valve, skin, a ligament, a tendon, a muscle, a thyroid gland, a nerve, and/or a blood vessel.

Organization of an organ or organoid through the printing process, disclosed herein, may require or be implemented by the sequential deposition of at least about 1, 10, 50, 100, 200, 300, 500, 600, 700, 800, 900, 1000, 10000, 100000, 1000000 or more layers of cells. Organization of a lymphoid organ through the printing process may require or be implemented by the sequential deposition of between 1 and 100 layers of cells. The size of a layer of cells may be tissue dependent. The size of a layer of cells may comprise a larger three-dimensional structure that may be one layer of cells or may comprise multiple layers of cells. The layer of cells may comprise about at least 10, $10^2$, $10^3$, $10^4$, $10^5$, $10^6$, $10^7$, $10^8$, $10^9$, $10^{10}$, or more cells.

Where precise placement of each cell type relative to the other is desired, cells should be printed in sequential steps with a wash step in between to remove the previously used media. Alternately, two or more cell types of different sizes may be printed simultaneously using two photopolymerizable materials of different polymerization wavelength and pore size, such that the larger cell type may become encapsulated in the pore of larger size and the smaller cell type may become encapsulated in the pore of smaller size. Cells are encapsulated in pores in accordance with the size of their nucleus, as the cytoskeleton is able to remodel based on the available space.

The laser light source may use high-energy green, blue, white, or lower frequencies of ultraviolet light to induce polymerization of the photopolymerizable material, or a high-resolution multi-photon light source of any wavelength may be used. The high-resolution, non-toxic multi-photon projection technology is uniquely suited to print detailed germinal centers that allow for the development of light and dark zones that recapitulate natural B cell affinity maturation. This method may be used in combination with microfluidic manipulation of vasculature, whether lymphatic or circulatory, to create functional collagen-based organs and/or organoids, such as lymph node organoids. Nontoxic wavelengths of visible and ultraviolet light may alternatively be used to print cell-containing structures or biogels to be seeded with cells.

The present disclosure encompasses the printing of lymphoid organs or organoids by two- or three-dimensional projection of a laser beam 1002 from an energy source 1000 (i.e., a laser, especially a high-resolution multi-photon laser beam but also including other possible light sources). The laser beam 1002 is intended to induce polymerization of a cell-containing media 126 in a predefined pattern to produce a final product that resembles in structure or function native, especially human lymphoid organs or organoids. Lymphoid organs are herein defined as small, fully functional, immune cell-containing structures that are capable of mounting and carrying out a functional and complete immune response, defined as the production of an antibody, chemical (e.g., cytokine), or cellular response against an antigen. Lymphoid organoids are here defined as partially complete lymphoid organs capable of demonstrating any type of immune activity on a cellular level. Immune activity includes but is not limited to: (a) cell activation, as defined by an upregulation or downregulation of a cell surface protein; (b) mitotic cell division; (c) changes in cell movement; (d) functional cell movement within the printed structures; (e) development of an immune response as measured by a change in protein production such as antibodies, cytokines, or chemokines; and (f) development of novel proteins by mutation associated with activation such as somatic hypermutation typical of B cells.

Figure 18A:
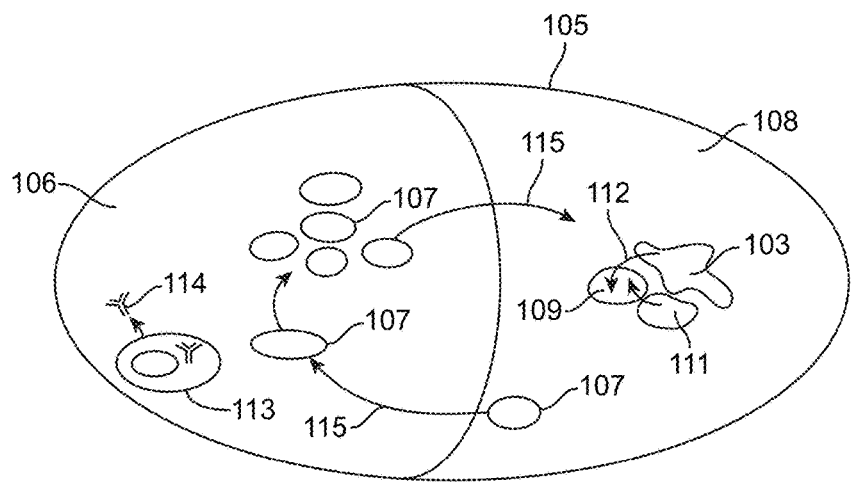
FIGS. 18A-18B illustrate a B cell germinal center and a thymic-like development niche.

Lymph node organoids or lymphocyte containing structures designed to recapitulate basic lymph node function and provide a cellular niche and microstructures to support lymphocyte interactions and development of functional immune responses; such as the formation of B cell germinal centers (GCs; FIG. 18A) and thymic-like development niches (FIG. 18B) printed as single units in multiple steps. Lymphoid organoids may be any semi-functional aggregations of immune cells, including partial structures of those depicted in FIGS. 18A and 18B.

Referring to FIG. 18A, the B cell germinal center 105 may be functionally separated into a B cell crowded dark zone 106, where B cells 107 proliferate and undergo somatic hypermutation, and a light zone 108, where B cells interact with whole-antigen bearing cells and/or accessory supporting cells 109, including, but not limited to dendritic cells, monocytes, other B cells 103, and/or with T cells 111 to receive positive signals including, but not limited to soluble factors and ligand-based cell surface interactions 112 after a functional receptor mutation or rearrangement. Once positive signals 112 are received, B cells 107 return to the dark zone 106 and continue the process of proliferation and receptor mutation. This process repeats itself until a dominant B cell clone or clones are selected for and become plasma B cells 113 the secret mature, class switched, highly specific antibody 114. Movement between light and dark zones occurs by single cell movement guided by endogenous chemokine gradient set up by accessory cells, and/or materials included in the bioprinting matrix 115.

Figure 18B:
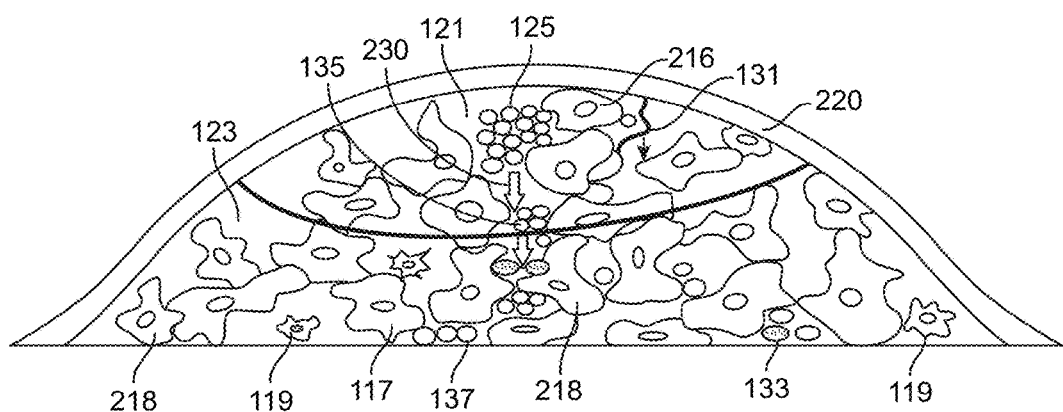

FIG. 18B depicts the thymic-like development niche. The printed structure may mimic the sequential development of T cells in the thymus, which migrate from the cortex tissue in the thymic organoid towards the medullary tissues as they proliferate and mature. The direction of this migration is represented by the arrow 230 in FIG. 18B. These movements are guided by cells sensing local chemokine gradients established by local cell populations and introduction of agents into the cellular printing matrix to assist in the establishment of cell niches. The distribution of a mix of accessory cells including, but not limited to cortical epithelial cells 216, medullary epithelial cells 117, dendritic cells 218, and macrophages 119, ensures that T cells may be in close proximity to the accessory cells most important at that stage of the T cell's development. This structure is comprised of a thymus capsule 220, a cortical region 121 and a medullary region 123. Immature thymocytes, double negative T cells, and macrophages (not shown in FIG. 18B) may be scattered throughout the cortex to clear apoptotic thymocytes. Deeper in the thymus, medullary epithelial cells, a higher abundance of macrophages, and dendritic cells of bone marrow origin closely associate with mature thymocytes and promote further development. During the process of development, double negative immature thymocytes 125 move through the cortical structures 131 and accessory cells 216 towards the medulla 123, differentiating into single positive thymocytes 135, into the medullary region to become mature thymocytes 137 that are CD4 or CD8 positive. During this process some cells undergo cell death and may become apoptotic cells 133.

Figure 19:
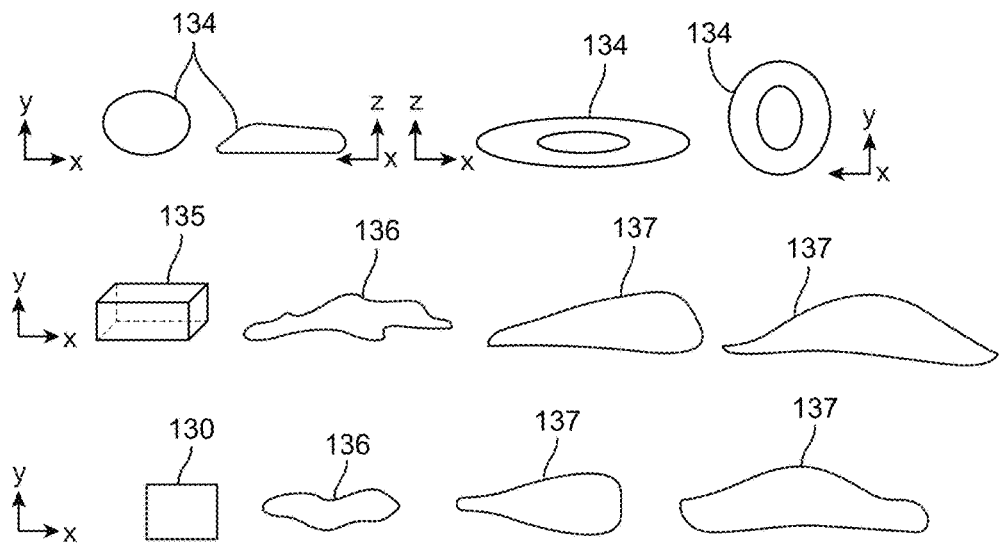
FIG. 19 illustrates various structural examples of lymph node organoids, designed for the purpose of promoting cellular niche formation and relevant cell-cell interactions that occur during an immune response.

As depicted in FIG. 19, the shape of these printed structures may be spherical, oval, ovate, or ovoid that may have a flat or torus-like bottom and may contain a hollow or indented center to allow for varied surface area configurations 134; square, rectangular, cuboid, or any polygonal shape 135; free-form, especially where the free-form design is intended to promote formation of multicellular niches asymmetrical spheres 136; or in a tear drop-like shape 137 with long tails coming from any direction.

Figure 20:
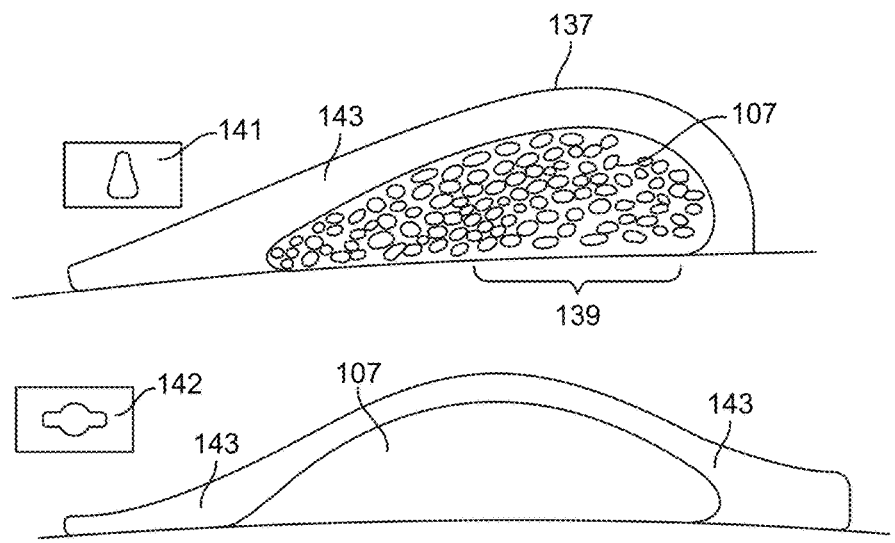
FIG. 20 illustrates lymph node organoids or lymphocyte-containing organs that may be printed in an asymmetrical teardrop-like shape.

Lymphoid organs and organoids may be printed as shown in FIG. 20 in a teardrop-like shape 137, such that B cells 138 are clustered at the larger end(s) of the structure 139 in a sphere or semi-spheroid structure, with accessory cells 143 tapering off to one or both sides. B cells may be independently motile in response to local chemokine gradients through organized cell niches during the affinity maturation process. Figures are illustrated as a cross-section of a 3D structure of the top-down view of an asymmetrical tear-drop like shapes, single-tailed 141 and double-tailed 142.

Figure 23:
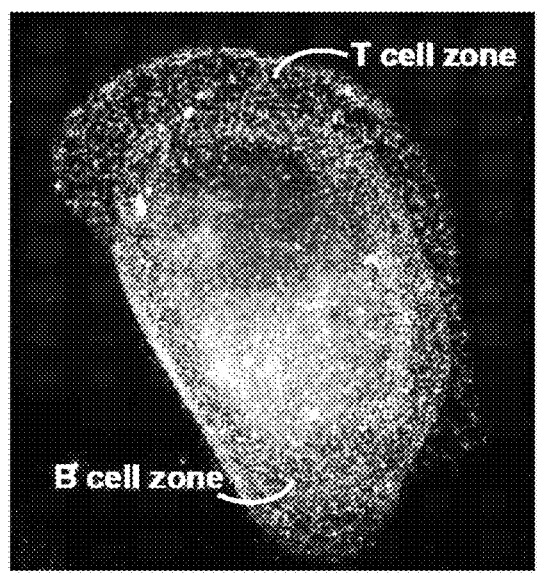
FIG. 23 shows a microscopy image of a three-dimensional printed lymph node organoid produced by the methods disclosed herein. The T cell zone indicates the area of the tissue comprising T cells and a mixture of supporting accessory cells. The B cell zone indicates the area of the tissue comprising B cells and a mixture of supporting accessory cells.

Lymphoid organs and organoids may be printed as shown in FIG. 23. FIG. 23 shows a microscopy image of a three-dimensional printed lymph node organoid produced by the methods disclosed herein. T cells and B cells are shown to be physically compartmentalized into separate regions of the lymph node organoid. The T cell zone indicates the area of the tissue comprising T cells and a mixture of supporting accessory cells. The B cell zone indicates the area of the tissue comprising B cells and a mixture of supporting accessory cells.

Chemokine gradients may be established by cells that are part of the encapsulated cell network or chemokine gradients may be deposited as part of the printing process.

B cells, T cells, follicular dendritic cells, and other cell types may be printed in suspension, adhered to the bottom or sides of the culture dish/well plate, or printed within a network of collagen or another biological, biocompatible, or bioinert material.

Where cells are printed within a network, the network may be arranged in a reticular, amorphous, or organized net. An organized net is any net with a repeated geometric or other pattern, including hexagonal, square/rectangular, rhomboid, circular, semi-circular, spherical, semi-spherical, or any combination of shapes therein. A reticular or amorphous net is created without significant regard for geometric pattern, with the primary purpose of being created rapidly and being capable of encapsulating and containing cells. Additionally, some nets may appear amorphous to the untrained observer but, in fact, have a specific shape or design designed to facilitate cellular interactions or movement between or within cellular niches.

Native architecture may be obtained from imaging data and rendered into two- or three-dimensional images with defined edges and/or grey areas, which are edges that are not precisely defined, but fall somewhere within a designated range, for projection into a polymerizable hydrogel. Such imaging data may provide sufficient detail to enable precise re-creation of multicellular niches that support cell-cell interactions during an immune response. Multicellular niches are developed in the immune system for single B- or T-cell selection based on receptor recognition of a foreign pathogen or material. High reactivity of a receptor or high affinity recognition during an immune response leads to selection for that B or T cell and further cell division and expansion of the numbers of cells that express the highly reactive receptor. Competition for survival signals transmitted by the receptor that is highly reactive in these multicellular niches leads to positive selection of the most reactive B or T cell. Native lymph node architecture can support the development of this selection process which is dependent upon a sequence of specific cell-cell interactions that support selection and proliferation of the highly reactive cells. Therefore, three-dimensional native architecture that allows for cell-cell interactions and independent cell movement is a critical component of the B-cell and T-cell clonal selection process. As such, this architecture is an important component of the printed lymph node and one that is afforded especially by the use of multi-photon lasers in the printing process, though it may be possible to achieve function without printing in this level of resolution achieved with projection of wave-front shaped multi-photon laser light.

Cell-cell interactions that may occur within a multicellular niche include, but are not limited to: B cell-T cell conjugate formation, B cell B cell interactions, B cell—macrophage, T cell-dendritic cell interactions), and stromal cell interactions with T, B and Dendritic cells. Interactions are not distinctly paired interactions and clusters or clumps of cells of various types often form during an immune reaction, especially in an established cellular niche or tissue like structure.

T cells, as used here, may refer to any form of a T cell including but not limited to CD8+ or CD4+ T cells. B cells may refer to B cells in any developmental phase including but not limited to naive B cells, mature B cells, plasma B cells, B1 B cells, or B2 B cells.

Figure 17:
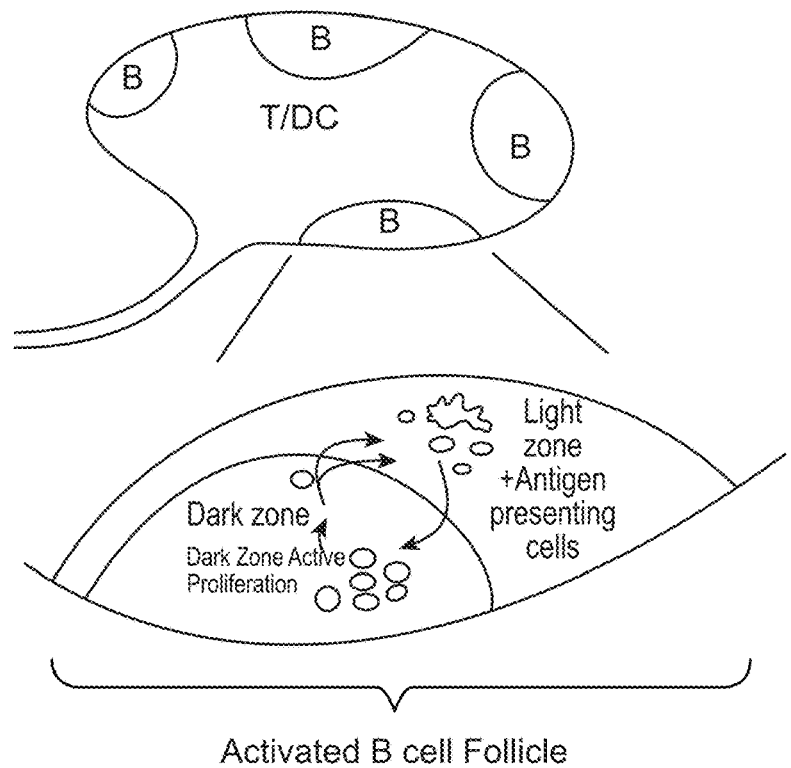
FIG. 17 illustrates a B-cell germinal center comprising a dark zone where B cells proliferate and a light zone where B cells interact with antigen presenting cells and accessory cells.

FIG. 17 depicts lymphoid organs in generalized detail as their structure is currently understood and do not necessarily include every structural detail that may be obtained from imaging data, nor may the final product necessarily include every depicted structural detail; lymphoid organs and organoids are herein ultimately defined by their function.

Multiple organoid units may be printed within a single structure to produce larger organs, up to and including a fully sized organ. Multiple lymphoid units may be printed within a single structure to produce larger immune organs, up to and including a fully sized lymph node or thymus. The limiting factor for size is vascularization, which is essential for tissues larger than 200 micron in width due to the diffusion limits of most gases and nutrients. The completed lymphoid organ or organoid may be between 50 and 200 microns thick without vascularization. If vascularized, the tissue may be 50 microns to 10 cm thick, may be of any shape or size, and may contain both circulatory and lymphatic vasculature. Vasculature may include valves and/or sphincters. In some embodiments, vasculature may be achieved by printing endothelial cells or precursors thereof within a net 500 intended to closely resemble native microvasculature, the structure of which is obtained from high-resolution imaging data. Capillary beds may branch from larger arterioles and arteries and branch into venules and veins in accordance with the relevant anatomy.

In an aspect, the present disclosure provides a method of producing a population of human immunological proteins. The method may comprise providing a medium. The medium may comprise a plurality of cells and one or more polymer precursors. The polymer precursors may be biogel precursors. The method may comprise depositing at least one layer of the medium onto a substrate. The substrate may be a media chamber. The substrate may be a tissue culture plate or well. The substrate may be a microfluidic chamber. The substrate may be a microfluidic chip. The substrate may be a polymeric scaffold.

The method may comprise subjecting the at least one layer of the medium to an energy source to form at least a portion of the 3D lymphoid organoid comprising at least a subset of the plurality of cells, and a biogel formed from the one or more polymer precursors. The method may comprise a layer-by-layer deposition of the medium patterned according to a three-dimensional (3D) projection. The 3D projection may be in accordance with computer instructions for printing the 3D lymphoid organoid in computer memory. The layer-by-layer deposition of the medium patterned according to a three-dimensional (3D) projection and formation of the biogel may be done by subjecting the medium to the energy source (e.g., a laser). For example, the laser may be projected along a light path in accordance to the 3D projection in order to polymerize the polymer precursors in the medium and form at least a portion of the 3D lymphoid organoid comprising the plurality of cells and the biogel. In another aspect, the method may comprise a manual layer-by-layer deposition of the medium using a pipette or a capillary tube to deposit at least one microdroplet of the medium onto a substrate. In this example, a 3D projection comprising the pattern to be printed may not be necessary, rather the microdroplets of the medium may be subjected to an energy source (e.g., a heat or light source) once deposited, in order to form at least a portion of the 3D lymphoid organoid comprising the biogel and the plurality of cells. In yet another aspect, the method may comprise a layer-by-layer deposition of the medium by use of a microfluidic device. The microfluidic device may control total volume of a microdroplet of the medium that is deposited in a layer-by-layer manner onto a substrate. The microfluidic device may control total number of cells per each microdroplet of the medium that is deposited in a layer-by-layer manner onto a substrate. In yet another aspect, the method may comprise a layer-by-layer deposition of the medium by use of a printer. The printer may be a laser printer, a layer-by-layer inkjet printer (e.g., a thermal inkjet printer or a piezoelectric inkjet printer), a layer-by-layer extrusion 3D printer (e.g., a pneumatic extrusion bioprinter or a mechanical extrusion bioprinter), or any combination thereof. Microdroplets of medium may be combined with other microdroplets such that cells may be organized into functional multi-cellular tissue niches.

Layered microdroplets may be cured, fused, solidified, gelled, crosslinked, polymerized, or photopolymerized in sequence or all at once using an energy source or via a chemical (e.g., a crosslinker or a photoinitiator). The energy source may be an energy beam, a heat source, or a light source. The energy source may be a laser, such as a fiber laser, a short-pulsed laser, or a femto-second pulsed laser. The energy source may be a heat source, such as a thermal plate, a lamp, an oven, a heated water bath, a cell culture incubator, a heat chamber, a furnace, a drying oven, or any combination thereof. The energy source may be a light source, such as white light, infrared light, ultraviolet (UV) light, near infrared (NIR) light, visible light, a light emitting diode (LED), or any combination thereof. The energy source may be a sound energy source, such as an ultrasound probe, a sonicator, an ultrasound bath, or any combination thereof. The energy source may be an electromagnetic radiation source, such as a microwave source, or any combination thereof.

The medium may be physically polymerized in order to form a biogel. The medium may be polymerized by a heat source in order to form a biogel. The medium may be chemically polymerized in order to form a biogel; for example, by use of a cross-linker. Non-limiting examples of cross-linkers include 1-ethyl-3-(3-dimethylaminopropyl)-carbodiimide (EDC), glutaraldehyde, and 1-ethyl-3-3-dimethyl aminopropyl carbodiimide (EDAC). The medium may comprise a photoinitiator, a cross-linker, collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof. The biogel may comprise a photoinitiator, a cross-linker, collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof. The polymer precursor may be collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof.

The biogel may be a hydrogel. The biogel may be a biocompatible hydrogel. The biogel may be a polymeric hydrogel. The biogel may be a hydrogel bead. The biogel may be a hydrogel nanoparticle. The biogel may be a hydrogel droplet. The biogel may be a hydrogel microdroplet.

The microdroplet may have a diameter measuring at least about 10 microns (μm) to about 1000 μm. The microdroplet may have a diameter measuring at least about 10 μm. The microdroplet may have a diameter measuring at most about 1,000 μm. The microdroplet may have a diameter measuring about 10 μm to about 50 μm, about 10 μm to about 100 μm, about 10 μm to about 200 μm, about 10 μm to about 300 μm, about 10 μm to about 400 μm, about 10 μm to about 500 μm, about 10 μm to about 600 μm, about 10 μm to about 700 μm, about 10 μm to about 800 μm, about 10 μm to about 900 μm, about 10 μm to about 1,000 μm, about 50 μm to about 100 μm, about 50 μm to about 200 μm, about 50 μm to about 300 μm, about 50 μm to about 400 μm, about 50 μm to about 500 μm, about 50 μm to about 600 μm, about 50 μm to about 700 μm, about 50 μm to about 800 μm, about 50 μm to about 900 μm, about 50 μm to about 1,000 μm, about 100 μm to about 200 μm, about 100 μm to about 300 μm, about 100 μm to about 400 μm, about 100 μm to about 500 μm, about 100 μm to about 600 μm, about 100 μm to about 700 μm, about 100 μm to about 800 μm, about 100 μm to about 900 μm, about 100 μm to about 1,000 μm, about 200 μm to about 300 μm, about 200 μm to about 400 μm, about 200 μm to about 500 μm, about 200 μm to about 600 μm, about 200 μm to about 700 μm, about 200 μm to about 800 μm, about 200 μm to about 900 μm, about 200 μm to about 1,000 μm, about 300 μm to about 400 μm, about 300 μm to about 500 μm, about 300 μm to about 600 μm, about 300 μm to about 700 μm, about 300 μm to about 800 μm, about 300 μm to about 900 μm, about 300 μm to about 1,000 μm, about 400 μm to about 500 μm, about 400 μm to about 600 μm, about 400 μm to about 700 μm, about 400 μm to about 800 μm, about 400 μm to about 900 μm, about 400 μm to about 1,000 μm, about 500 μm to about 600 μm, about 500 μm to about 700 μm, about 500 μm to about 800 μm, about 500 μm to about 900 μm, about 500 μm to about 1,000 μm, about 600 μm to about 700 μm, about 600 μm to about 800 μm, about 600 μm to about 900 μm, about 600 μm to about 1,000 μm, about 700 μm to about 800 μm, about 700 μm to about 900 μm, about 700 μm to about 1,000 μm, about 800 μm to about 900 μm, about 800 μm to about 1,000 μm, or about 900 μm to about 1,000 μm. The microdroplet may have a diameter measuring about 10 μm, about 50 μm, about 100 μm, about 200 μm, about 300 μm, about 400 μm, about 500 μm, about 600 μm, about 700 μm, about 800 μm, about 900 μm, or about 1,000 μm.

The microdroplet may have a volume of about 1 microliter (μl) to about 500 μl. The microdroplet may have a volume of at least about 1 μl. The microdroplet may have a volume of at most about 500 μl. The microdroplet may have a volume of about 1 μl to about 2 μl, about 1 μl to about 3 μl, about 1 μl to about 4 μl, about 1 μl to about 5 μl, about 1 μl to about 10 μl, about 1 μl to about 20 μl, about 1 μl to about 25 μl, about 1 μl to about 50 μl, about 1 μl to about 75 μl, about 1 μl to about 100 μl, about 1 μl to about 500 μl, about 2 μl to about 3 μl, about 2 μl to about 4 μl, about 2 μl to about 5 μl, about 2 μl to about 10 μl, about 2 μl to about 20 μl, about 2 μl to about 25 μl, about 2 μl to about 50 μl, about 2 μl to about 75 μl, about 2 μl to about 100 μl, about 2 μl to about 500 μl, about 3 μl to about 4 μl, about 3 μl to about 5 μl, about 3 μl to about 10 μl, about 3 μl to about 20 μl, about 3 μl to about 25 μl, about 3 μl to about 50 μl, about 3 μl to about 75 μl, about 3 μl to about 100 μl, about 3 μl to about 500 μl, about 4 μl to about 5 μl, about 4 μl to about 10 μl, about 4 μl to about 20 μl, about 4 μl to about 25 μl, about 4 μl to about 50 μl, about 4 μl to about 75 μl, about 4 μl to about 100 μl, about 4 μl to about 500 μl, about 5 μl to about 10 μl, about 5 μl to about 20 μl, about 5 μl to about 25 μl, about 5 μl to about 50 μl, about 5 μl to about 75 μl, about 5 μl to about 100 μl, about 5 μl to about 500 μl, about 10 μl to about 20 μl, about 10 μl to about 25 μl, about 10 μl to about 50 μl, about 10 μl to about 75 μl, about 10 μl to about 100 μl, about 10 μl to about 500 μl, about 20 μl to about 25 μl, about 20 μl to about 50 μl, about 20 μl to about 75 μl, about 20 μl to about 100 μl, about 20 μl to about 500 μl, about 25 μl to about 50 μl, about 25 μl to about 75 μl, about 25 μl to about 100 μl, about 25 μl to about 500 μl, about 50 μl to about 75 μl, about 50 μl to about 100 μl, about 50 μl to about 500 μl, about 75 μl to about 100 μl, about 75 μl to about 500 μl, or about 100 μl to about 500 μl. The microdroplet may have a volume of about 1 μl, about 2 μl, about 3 μl, about 4 μl, about 5 μl, about 10 μl, about 20 μl, about 25 μl, about 50 μl, about 75 μl, about 100 μl, or about 500 μl.

The biogel may be a solution with a viscosity ranging from at least about $1 \times 10^{-3}$ Pascal-second (Pa·s) to about 100,000 Pa·s or more when measured at about 25 degrees Celsius (° C.). When measured at about 25 degrees Celsius (° C.), the biogel may have a viscosity of about 0.001 Pa·s to about 100,000 Pa·s. When measured at about 25 degrees Celsius (° C.), the biogel may have a viscosity of at least about 0.001 Pa·s. When measured at about 25 degrees Celsius (° C.), the biogel may have a viscosity of at most about 100,000 Pa·s. When measured at about 25 degrees Celsius (° C.), the biogel may have a viscosity of about 0.001 Pa·s to about 0.01 Pa·s, about 0.001 Pa·s to about 0.1 Pa·s, about 0.001 Pa·s to about 1 Pa·s, about 0.001 Pa·s to about 10 Pa·s, about 0.001 Pa·s to about 100 Pa·s, about 0.001 Pa·s to about 1,000 Pa·s, about 0.001 Pa·s to about 10,000 Pa·s, about 0.001 Pa·s to about 50,000 Pa·s, about 0.001 Pa·s to about 100,000 Pa·s, about 0.01 Pa·s to about 0.1 Pa·s, about 0.01 Pa·s to about 1 Pa·s, about 0.01 Pa·s to about 10 Pa·s, about 0.01 Pa·s to about 100 Pa·s, about 0.01 Pa·s to about 1,000 Pa·s, about 0.01 Pa·s to about 10,000 Pa·s, about 0.01 Pa·s to about 50,000 Pa·s, about 0.01 Pa·s to about 100,000 Pa·s, about 0.1 Pa·s to about 1 Pa·s, about 0.1 Pa·s to about 10 Pa·s, about 0.1 Pa·s to about 100 Pa·s, about 0.1 Pa·s to about 1,000 Pa·s, about 0.1 Pa·s to about 10,000 Pa·s, about 0.1 Pa·s to about 50,000 Pa·s, about 0.1 Pa·s to about 100,000 Pa·s, about 1 Pa·s to about 10 Pa·s, about 1 Pa·s to about 100 Pa·s, about 1 Pa·s to about 1,000 Pa·s, about 1 Pa·s to about 10,000 Pa·s, about 1 Pa·s to about 50,000 Pa·s, about 1 Pa·s to about 100,000 Pa·s, about 10 Pa·s to about 100 Pa·s, about 10 Pa·s to about 1,000 Pa·s, about 10 Pa·s to about 10,000 Pa·s, about 10 Pa·s to about 50,000 Pa·s, about 10 Pa·s to about 100,000 Pa·s, about 100 Pa·s to about 1,000 Pa·s, about 100 Pa·s to about 10,000 Pa·s, about 100 Pa·s to about 50,000 Pa·s, about 100 Pa·s to about 100,000 Pa·s, about 1,000 Pa·s to about 10,000 Pa·s, about 1,000 Pa·s to about 50,000 Pa·s, about 1,000 Pa·s to about 100,000 Pa·s, about 10,000 Pa·s to about 50,000 Pa·s, about 10,000 Pa·s to about 100,000 Pa·s, or about 50,000 Pa·s to about 100,000 Pa·s. When measured at about 25 degrees Celsius (° C.), the biogel may have a viscosity of about 0.001 Pa·s, about 0.01 Pa·s, about 0.1 Pa·s, about 1 Pa·s, about 10 Pa·s, about 100 Pa·s, about 1,000 Pa·s, about 10,000 Pa·s, about 50,000 Pa·s, or about 100,000 Pa·s.

The biogel may be a hydrogel comprising a plurality of cells. The biogel may be a hydrogel comprising a plurality of non-hydrogel beads. The biogel may be a hydrogel comprising a plurality of non-hydrogel nanoparticles. The biogel may be a hydrogel comprising a plurality of non-hydrogel microparticles. The biogel may be a hydrogel comprising a plurality of non-hydrogel nanorods. The biogel may be a hydrogel comprising a plurality of non-hydrogel nanoshells. The biogel may be a hydrogel comprising a plurality of liposomes. The biogel may be a hydrogel comprising a plurality of non-hydrogel nanowires. The biogel may be a hydrogel comprising a plurality of non-hydrogel nanotubes. The biogel may be a gel in which the liquid component is water. A biogel may be a network of polymer chains in which water is the dispersion medium. The network of polymer chains maybe a network of hydrophilic polymer chains. The network of polymer chains maybe a network of hydrophobic polymer chains. The biogel may be a degradable hydrogel. The biogel may be a non-degradable hydrogel. The biogel may be a resorbable hydrogel. The biogel may be a hydrogel comprising naturally-derived polymers such as collagen.

The method may comprise subjecting the at least the portion of the 3D lymphoid organoid to conditions sufficient to stimulate production of the one or more immunological proteins. The conditions sufficient to stimulate production of the one or more immunological proteins may comprise exposing the at least the portion of the 3D lymphoid organoid to an antigen in order to stimulate production of the one or more immunological proteins. The method may further comprise extracting one or more immunological proteins from the at least portion of the 3D lymphoid organoid. The immunological proteins may be selected from the list consisting of antibodies, T-cell receptors, and cancer immunotherapeutics. The plurality of cells in the medium may be from a subject. The plurality of cells may be autologous cells. The plurality of cells may be allogeneic cells. The plurality of cells may be stem cells. The plurality of cells may be induced pluripotent stem cells, pluripotent stem cells, embryonic stem cells, or a combination thereof. The plurality of cells may be stem cells that may be differentiated into B cells, T cells, or a combination thereof. The plurality of cells may be selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same.

The 3D lymphoid organoid may be selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ.

Figure 21:
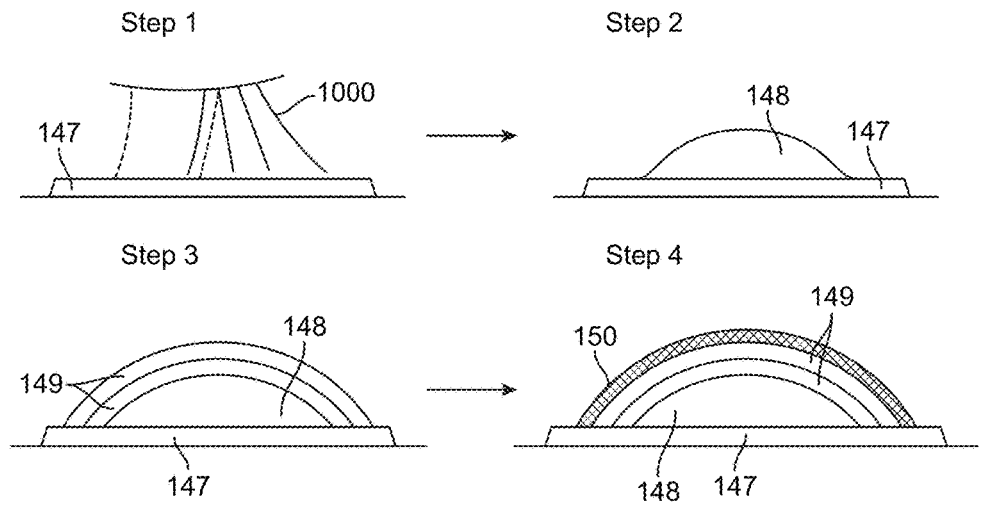
FIG. 21 illustrates a sequential process of depositing layers of biogels containing lymphocytes for the purpose of building a lymph node organoid.

FIG. 21 illustrates a four-step process in which biogels are polymerized by an energy source that includes, but is not limited to white light, single-, or multi-photon laser light for printing lymph node organoids or lymphocyte-containing organs 146 in sequential layers.

As shown in FIG. 21, in sequential order, a basement layer 147, two cell layers, a base cell layer 148, and secondary cell layers 149 are printed. Layer by layer deposition of biogel layers may use an energy source such as white light or heat to fuse each biogel layer to each other. The secondary cell layers may comprise one or more sequential layers. The secondary cell layers 149 may comprise a mixture of accessory cells, T cells, and antigen. The secondary cell layers 149 may comprise a protective capsule 150. In FIG. 21, Step 1 shows a basement layer 147. The basement layer 147 may comprise collagen or other biological, bioinert, or biocompatible material. The basement layer 147 may comprise cells. The basement layer 147 may not comprise cells. The basement layer 147 may be polymerized by a light source 1000. In some embodiments, the biogel may not comprise a basement layer 147. The basement layer 147 may act as an anchor or link for subsequent layers such as base cell layer 148 and secondary cell layers 149.

In FIG. 21, Step 2 shows one or more new photopolymerizable biopolymer(s) in its/their monomeric form(s) (i.e., photopolymerizable polymeric precursors). The photopolymerizable polymeric precursors may comprise one or more cell types. In some embodiments, the one or more cell types are of lymphocytic or other eukaryotic origins. The photopolymerizable biopolymer(s) may comprise any combination of growth factors or cell reactive proteins. The photopolymerizable biopolymer(s) may comprise may be printed by any one of the previously described energy sources which may be projected by an apparatus. Antigen may be included in the print media at this stage. Antigen may not be included in the print media at this stage.

Step 3 may comprise repeating step 2 until the desired number of cell layers/cell types is achieved. Different cell types, media conditions, and/or photopolymerizable biopolymers may be used. In FIG. 21, Step 3 shows one iteration to produce secondary cell layer 149. In FIG. 21, Step 4 shows lymph node organoids or lymphocyte-containing organs 146 may be encapsulated in a mesh 150 containing few to no cells. This structure may be intended to maintain the integrity of the lymph node organoid or lymphocyte-containing organ during the culturing and development process. Any biomaterial may be used to generate the mesh 150. Cells may be encapsulated in the mesh 150. Encapsulated cells may be of any origin, including, but not limited to antigen presenting cells, stromal cells, or cells that are pre-exposed to antigen and activated for antigen presentation. This final printing step may be used to deposit a structure that is contiguous with the first layer of anchored collagen or biomaterial to make a sealed and anchored lymphoid organ.

Wash steps using a media containing no cells and that is not a printable material may occur between any given step to ensure complete rinse and removal of the previous cells and polymerizable materials. The final steps of all processes may require one or more wash steps to remove unwanted biogel and prepare tissue structures for culture.

Between 1 and 100 different steps may be included in the printing of lymph node organs or organoids. At least 1, 10, 50, 100, 200, 300, 500, 600, 700, 800, 900, 1000, 10000, 100000, 1000000, or more operations may be included in the printing of lymph node organs or organoids. At least 1, 10, 50, 100, 200, 300, 500, 600, 700, 800, 900, 1000, 10000, 100000, 1000000, or more operations may be included in the printing of organs and/or organoids.

Lymphoid organs and organoids may be printed in a format suitable for high-throughput antibody/receptor production and screening, to include 1-, 6-, 12-, 48-, 96-, and 384-well plates. No method for de novo in vitro development of lymphoid organs in a high throughput format with two- or three-dimensional projection printing of a multicellular environment from human tissues has, as yet, been used for B- or T-cell development and receptor screening. The introduction of such a high-throughput process has the potential to substantially speed the process of antibody production and screening. However, larger structures may be required for particular purposes, or high-throughput methods may not always be required. As such, neither the scope nor the utility of the present disclosure is limited to high-throughput formats.

At least 10, 50, 100, 200, 300, 400, 500, 600, 700, 800, 900, 10000, or more testable lymphatic organs and/or organoids may be printed by the methods disclosed herein. About 200 testable lymphatic organs and/or organoids may be printed by the methods disclosed herein. About 300 to about 500 testable lymphatic organs and/or organoids may be printed by the methods disclosed herein. About 500 to about 1000 testable lymphatic organs and/or organoids may be printed by the methods disclosed herein. One or more cell types of lymphocytic or other eukaryotic origins that are isolated from a donor may be used to print a lymphatic organ and/or organoid. The single donor may be selected based on his, her, or its genetic traits, disease history, sex, and/or race. At least 200, 300, 400, 500, 600, 700, 800, 900, 10000, or more testable lymphatic organs and/or organoids may be produced from a single donor. About 200 testable lymphatic organs and/or organoids may be produced from a single donor. About 300 to about 500 testable lymphatic organs and/or organoids may be produced from a single donor. About 500 to about 1000 testable lymphatic organs and/or organoids may be produced from a single donor.

Within the printed structure, cells may be most typically encapsulated within or scaffolded on a biological, biocompatible, or bio-inert gel-forming material or biogel. Materials may be synthetic, partially synthetic, or natural. These materials may be independently photopolymerizable, may require a photoinitiator to polymerize, or may be modified to polymerize in the presence of a laser source with or without a photoinitiator. Materials that may be incorporated into a biogel, either as the sole, primary, secondary, or otherwise supplementary component thereof, include but are not limited to: collagen, hyaluronic acid and other glycosaminoglycans, poly-dl-lactic-co-glycolic acid (PLGA), poly-1-lactic acid (PLLA), polyglycolic acid (PGA), alginate, gelatin, and agar.

Varying tensile strength and structures of cellular nets to be printed may be used in different regions to promote cell motility, cell-cell interaction, and reorganization. Cells that can engage in crawling and cell-cell interaction behaviors can take up, process, and deliver antigen to responding immune cells. Therefore, structures that match native lymph node architecture or take on a mesh framework may be printed to facilitate cell-cell interactions and motility. Structures that range between 2 and 50 micrometers in diameter for net apertures or as a distance between strands may be printed to facilitate cell-cell interactions and motility.

Cell types that may be included within the printed structure or surrounding media include, but are not limited to: stromal endothelial cells, endothelial cells, follicular reticular cells or precursors thereof, naive B cells or other immature B cells, memory B cells, plasma B cells, helper T cells and subsets of the same, effector T cells and subsets of the same, CD8+ T cells, CD4+ T cells, regulatory T cells, natural killer T cells, naive T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same, macrophages and subsets of the same, and leukocytes and subsets of the same.

Each of these cell types may be isolated via blood or tissue donation from a single donor and expanded to sufficient numbers via in vitro protocol for printing of lymphoid-like tissues. Some of these cell types may be immortalized from a given donor may be immortalized to promote expansion and use for protein production. Cells may also be obtained from cell lines or animal sources in the case of animal-based experiments. Cells may be sourced from circulating cells in the blood, a biopsy from lymph nodes, spleen, bone marrow or other tissues. Cells may be sourced from any vertebrate including companion animals, rodents, large mammals, and humans Cells for a single high-throughput assay may be sourced from distinct individual donors to increase the likelihood that one may have a highly reactive antibody. Cells may also be sourced from a donor with a capacity for a desired immune reaction, defined by medical or disease history, genotype, antibody response or titration, or immune reaction ongoing or induced, to increase the likelihood of a desirable immunological response, whether positive or negative. The cells may be sourced from a donor based on their age, genetic traits, disease history, sex, and/or race.

Multiple cell layers may be printed with or without chemokines, free-floating or tethered cell-signaling molecules, growth factors, cytokines, proteins, biological agents, or non-biological agents such as adjuvants or small molecules, added to the print media. Such factors may be stimulatory or inhibitory. Factors may be tethered to collagen or other biogel monomers by cross-linking prior to introduction into the printing media. Addition of cell-reactive proteins to specific layers of the organoid or to the surrounding media may serve the purpose of facilitating cell organization, cell development, cell movement, and other desirable events.

Growth factors, pro-inflammatory cytokines, anti-inflammatory chemokines, cell-reactive proteins, soluble receptors, and other signaling factors may be incorporated into the print media, print scaffold, and/or culturing/growth media. Such factors include, but are not limited to: IFN-gamma, TNF-$\alpha$, TGF-$\beta$, IL-1$\alpha$, IL-1$\beta$, IL-1ra, IL-2 IL-4, IL-6, IL-10, IL-11, IL-13, IL-21, IL-23, soluble TNF receptor p55, soluble TNF receptor p75, soluble IL-1 receptor type 2, IL-18 binding protein, CCL2, CCL1, CCL22, CCL17, CXCR3, CXCL9, CXCL10, CXCL11, and so on. Media conditions may be changed at different time points throughout the printing and/or culturing process to promote specific immunological events.

Immunological events may be induced by changes in cell culture medium or components added to cell culture medium. Examples of inducible immunological events include cell proliferation; release of specific cytokines and/or chemokines; secretion of receptors and cell-secreted proteins, including antibodies; evolution of receptors and cell-secreted proteins, including antibodies; or cellular alterations including, but not limited to, cell health, cell morphology, expressed proteins, and cell developmental state.

Use of Printed Lymph Node for Generation or Assessment of Antibodies, T cell Receptors, Immunological Products, or Immune Responses Lymphoid organs and organoids may be used to produce novel cell-secreted and/or membrane-bound immunological proteins, including antibodies and T cell receptors. They may additionally be used to generate cells or cell lines, including hybridomas, expressing those proteins and/or genetic sequences. The lymphoid organs and/or organoids, produced by the methods described herein, may be used to produce cancer immunotherapeutics. The lymphoid organs and/or organoids, produced by the methods described herein, may be used to produce T cells. Lymphoid organs and/or organoids, produced by the methods described herein, may be used to predict a cytokine release. The lymphoid organs and/or organoids, produced by the methods described herein, may provide in vivo cellular organization that is required for antibody affinity maturation.

Antibodies and other receptors, the cells or cell lines that generate them, and/or the genetic sequences that encode them may be produced by antigen challenge. Antibodies and other receptors may be generated from a single blood donation sample. Antibodies and other receptors may be generated from a plurality of blood donation samples. Antibodies or receptors produced by the methods disclosed herein may be generated in at least 1, 2, 3, 4, 5, 6, 7, 8, 9, 10, or more weeks. Antibodies or receptors, produced by the methods disclosed herein, may be generated in about six weeks. Antibodies or receptors, produced by the methods disclosed herein, may be generated in about ten weeks. Antibodies or receptors, produced by the methods disclosed herein, may be generated in about four weeks to about twelve weeks. Antibodies or receptors, produced by the methods disclosed herein, may be generated in the absence of animal and/or human surrogates. The antibodies, produced by the methods disclosed herein, may be fully human IgG antibodies. The antibodies, produced by the methods disclosed herein, may be reactive to protein-based target antigens. The antibodies, produced by the methods disclosed herein, may have an affinity for a target antigen of at least 0.01 pM, 0.1 pM, 1 pM, 10 pM, 100 pM, 1 nM, 10 nM, 100 nM, 200 nM, 300 nM, 400 nM, 500 nM, 600 nM 700 nM, 800 nM, 900 nM, 1000 nM, or more. The antibodies, produced by the methods disclosed herein, may have an affinity for a target antigen of about 500 nM. Antigen may be introduced into the cellular media and/or the printed scaffolding at any stage during the printing process; may be pre-incubated with a cell type or multiple cell types to be printed, including antigen-presenting cells such as follicular dendritic cells; or may be introduced into the printed lymphoid structure at any point during the development of the lymphoid structure.

The same antigen may be introduced at multiple time points and/or stages in the printing and development process of the lymphoid structure. Moreover, multiple distinct antigens may be introduced into the same lymphoid structure at either the same or different time points and/or stages in the printing and development process of the lymphoid structure.

Antigen may be introduced by a variety of methods, including, but not limited to: injection, delivery of cells cultured with antigen, deposition of antigen onto the surface of the lymph node organoid in a patch, introduction of antigen through lymphoid or circulatory microvasculature (if present), or introduction of soluble antigen in the media surrounding the lymph node.

Antigens that may be introduced include, but are not limited to natural or engineered: whole peptides, partial peptides, glycopeptides, whole proteins or protein subunits, carbohydrates, nucleic acids, live virus, heat-killed virus, viral particles, membrane bound or stabilized proteins, phage displayed antigens, and whole-cells. Antigen may be a theoretically innocuous stimulus (e.g., in the case of allergies) or may be a self-antigen (e.g., in the case of autoimmune disease or cancer). The generation of antibody libraries may be compatible with phage display, ribosome display, yeast display, bacterial display, mRNA display, and additional antibody directed evolution technologies.

Biologic and/or non-biologic immune adjuvants intended to promote, prolong, speed, or initiate an immune response may be introduced with, prior to, or following antigen introduction. Possible adjuvants include, including, but are not limited to, alum and Toll-like Receptor (TLR)-stimulating compounds. Adjuvant may be introduced by the same or different means of introduction as antigen.

Biologic and/or non-biologic agents intended to dampen, delay, slow, or halt an immune response may be introduced with, prior to, or following antigen introduction. Adjuvant may be introduced with, prior to, or following such inhibitory agents, or may not be introduced in association with inhibitory agents. Such agents may include pro-apoptotic agents and/or receptor inhibitors, including small molecules, blocking antibodies, and other inhibitory agents.

Antibody, secreted receptor, partial cells, or whole cells may be collected following completion or partial completion of an immunological response. Methods of extraction may result in destruction of the printed lymphoid structure or may leave the lymphoid structure intact for further use or analysis. Methods of extraction of a desired product may include, but are not limited to: flow cytometry-based cell sorting (FACS), single-cell dilution from culture, selection based on surface antibody expression, and selection based on microfluidics methods and channels. Secreted products may be collected by media collection.

Printed lymphoid organs and/or organoids may alternately or additionally be used to assess immunological events, cellular interactions, cellular changes, and other measurable or perceivable events for purposes including, but not limited to: vaccine development; vaccine evaluation, including both potential for damage to the immune system (e.g., safety testing) and evaluation of immune response with or without introduction of the antigen against which the vaccine is intended to act (e.g., efficacy evaluation); pharmaceutical testing of biologic and/or non-biologic drug compounds or drug combinations, including potential for damage to the immune system (e.g., safety testing) and evaluation of a drugs effect on the immune system, whether intentional (e.g., efficacy evaluation) or unintentional (e.g., side-effect testing); screening of potentially immune-acting biologic and nonbiologic agents intended for therapeutic or other use, especially where a high-throughput printing design is used; basic research of immunological response and cellular interactions under a variety of laboratory-induced or naturally occurring conditions; and diagnostic evaluations including, but are not limited to, mixed-donor lymphocyte reactions; e.g., for evaluating transplant compatibility and reactions to foreign or self-derived agents or antigens; cancer immunotherapy predictive screening assay; T cell thymic selection assay; T cell clonal selection assay from native repertoire; and/or cytokine storm predictive assay. Antigens for transplant evaluation and reactivity of a patient's immune system may include antigens associated with allergy, autoimmune disease, cancer, beneficial microbes and viruses, and/or harmful or potentially harmful microbes and viruses.

Immunological events that may be measured or observed for such purposes include, but are not limited to: lymphocyte behavior, activation state, phenotype, proliferation rate, cellular interactions, changes in cellular interactions, and/or expression of internal and external markers of cell activation.

Measurements that can be made to evaluate such immunological events include, but are not limited to: antibody class-switching; cytokine-based responses; cell differentiation; responses to adjuvants for vaccination; responses to vaccines; cell proliferation; cell killing; cell phenotype; changes in cell phenotype, whether induced or as part of natural developmental processes; memory cell development; memory cell recall; assessment of memory cell populations endogenous to the donor; any predictive measurements, including immune responses for pharmaceutical testing or evaluation of allergic responses; and so on, according to existing or yet non-existent protocols for assessing immunological events.

The printed lymphoid organs and organoids, produced by the methods described herein, may be used to predict a cytokine release. The cytokine storm predictive assay may predict cytokine release induced by a therapeutic. The storm predictive assay may predict a cytokine release induced by an antibody-based therapeutic, a small molecule therapeutic, a cell-based therapeutic, a peptide, a nucleic acid, or any combinations thereof. The cytokine storm predictive assay may predict a cytokine release in humans, primates, and/or rodents. The cytokine storm predictive assay may measure the levels of inflammatory mediators such as cytokines, oxygen free radicals, and coagulation factors. The cytokine storm predictive assay may measure pro-inflammatory cytokines, anti-inflammatory cytokines, colony-stimulating factors, interferons, interleukins, and/or tumor necrosis factors that are released as a result of the cytokine storm. The cytokines measured by the cytokine storm predictive assay may be tumor necrosis factor-α (TNF-α), interferon-gamma (IFN-γ), interleukin-2 (IL-2), IL-4, IL-6, IL-8, IL-10, IL-α, IL-1β, IL-1 receptor antagonist, granulocyte-macrophage colony-stimulating factor (GM-CSF), macrophage colony-stimulating factor (M-CSF), and granulocyte colony-stimulating factor (G-CSF), CXCR3, CXCL9, CXCL10, and/or CXCL11.

Measurements of immune responses can be performed by methods that include, but are not limited to, use of whole cells; sorting or isolating cells based on their cellular phenotype, which may include morphology and/or receptor expression profile; and collection of serum or media for purposes including the evaluation of secretion rate or specific secreted molecules.

Methods that may be used to assess cellular state or changes in cellular state, including genetic and phenotypic evaluation, include, but are not limited to: enzyme-linked immunosorbent assays (ELISA), partial genetic sequencing or sequencing of a particular genomic locus, full-genome sequencing, gel electrophoresis of proteins or nucleic acids, polymerase chain reaction (PCR), quantitative PCR, reverse-transcription PCR, Western blot, flow cytometry for analysis of cell phenotype or activation state, antibody selection, mass spectrometry, and so on.

Methods of Printing Cell-Containing Structures

The present disclosure provides methods and systems of printing and using a three-dimensional cell-containing matrix. In an aspect, a method of using a three-dimensional (3D) cell-containing matrix comprises: providing a media chamber comprising a medium comprising (i) a plurality of cells and (ii) one or more polymer precursors. Next, the method may comprise directing at least one energy beam to the medium in the media chamber along at least one energy beam path that is patterned into a three-dimensional (3D) projection in accordance with computer instructions for printing the 3D cell-containing medical device in computer memory, to form at least a portion of the 3D cell-containing matrix comprising (i) at least a subset of the plurality of cells, and (ii) a polymer formed from the one or more polymer precursors. Next, the method may comprise positioning the 3D cell-containing matrix in a subject.

In another aspect, a method of using a three-dimensional (3D) cell-containing matrix, comprises (i) printing the 3D cell-containing matrix comprising a plurality of cells, and (ii) positioning the 3D cell-containing matrix in a subject.

In another aspect, a method for using a three-dimensional (3D) cell-containing matrix, comprises providing a media chamber comprising a first medium. The first medium may comprise a first plurality of cells and a first polymeric precursor. Next, the method may comprise directing at least one energy beam to the first medium in the media chamber along at least one energy beam path in accordance with computer instructions for printing the 3D cell-containing matrix in computer memory, to subject at least a portion of the first medium in the media chamber to form a first portion of the 3D cell-containing matrix. Next, the method may comprise providing a second medium in the media chamber. The second medium may comprise a second plurality of cells and a second polymeric precursor. The second plurality of cells may be of a different type than the first plurality of cells. Next, the method may comprise directing at least one energy beam to the second medium in the media chamber along at least one energy beam path in accordance with the computer instructions, to subject at least a portion of the second medium in the media chamber to form a second portion of the 3D cell-containing matrix. Next, the method may comprise positioning the first and second portions of the 3D cell-containing matrix in a subject.

In another aspect, a method of using a three-dimensional (3D) cell-containing matrix, comprises (i) printing the 3D cell-containing matrix comprising a first plurality of cells and a second plurality of cells. The first plurality of cells may be different from the second plurality of cells. Next, the method may comprise (ii) positioning the 3D cell-containing matrix in a subject.

The plurality of cells may be from a subject. The method plurality of cells may be selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. The B cells may be selected from the list consisting of naïve B cells, mature B cells, plasma B cells, B1 B cells and B2 B cells. The T cells may be selected from the list consisting of CD8+ and CD4+. The 3D cell-containing matrix may form a suture, stent, staple, clip, strand, patch, graft, sheet, tube, pin, or screws. The graft may be selected from the list consisting of skin implant, uterine lining, neural tissue implant, bladder wall, intestinal tissue, esophageal lining, stomach lining, hair follicle embed skin, and retina tissue.

The 3D cell-containing matrix may be from about 1 micrometer (μm) to about 10 centimeters (cm). The 3D cell-containing matrix may be from at least about 5 μm to about 10 cm or more. The 3D cell-containing matrix may be from at least about 10 μm to about 10 cm or more. The 3D cell-containing matrix may be from at least about 100 μm to about 10 cm or more. The 3D cell-containing matrix may be from at least about 500 μm to about 10 cm or more. The 3D cell-containing matrix may be from at least about 1000 μm to about 10 cm or more. The 3D cell-containing matrix may be from at least about 1 cm to about 10 cm or more. The 3D cell-containing matrix may be from about at least 5 to about 10 cm or more.

The 3D cell-containing matrix may be about 1 μm to about 1,000 μm. The 3D cell-containing matrix may be at least about 1 μm. The 3D cell-containing matrix may be at most about 1,000 μm. The 3D cell-containing matrix may be about 1 µm to about 5 µm, about 1 µm to about 10 µm, about 1 µm to about 100 µm, about 1 µm to about 1,000 µm, about 5 µm to about 10 µm, about 5 µm to about 100 µm, about 5 µm to about 1,000 µm, about 10 µm to about 100 µm, about 10 µm to about 1,000 µm, or about 100 µm to about 1,000 µm. The 3D cell-containing matrix may be about 1 µm, about 5 µm, about 10 µm, about 100 µm, or about 1,000 µm.

The 3D cell-containing matrix may be about 0.5 cm to about 10 cm. The 3D cell-containing matrix may be at least about 0.5 cm. The 3D cell-containing matrix may be at most about 10 cm. The 3D cell-containing matrix may be about 0.5 cm to about 1 cm, about 0.5 cm to about 2 cm, about 0.5 cm to about 3 cm, about 0.5 cm to about 4 cm, about 0.5 cm to about 5 cm, about 0.5 cm to about 6 cm, about 0.5 cm to about 7 cm, about 0.5 cm to about 8 cm, about 0.5 cm to about 9 cm, about 0.5 cm to about 10 cm, about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 5 cm to about 6 cm, about 5 cm to about 7 cm, about 5 cm to about 8 cm, about 5 cm to about 9 cm, about 5 cm to about 10 cm, about 6 cm to about 7 cm, about 6 cm to about 8 cm, about 6 cm to about 9 cm, about 6 cm to about 10 cm, about 7 cm to about 8 cm, about 7 cm to about 9 cm, about 7 cm to about 10 cm, about 8 cm to about 9 cm, about 8 cm to about 10 cm, or about 9 cm to about 10 cm. The 3D cell-containing matrix may be about 0.5 cm, about 1 cm, about 2 cm, about 3 cm, about 4 cm, about 5 cm, about 6 cm, about 7 cm, about 8 cm, about 9 cm, or about 10 cm.

The 3D cell-containing matrix may be at least about 1 µm or more. The 3D cell-containing matrix may be at least about 5 µm or more. The 3D cell-containing matrix may be at least about 10 µm or more. The 3D cell-containing matrix may be at least about 50 µm or more. The 3D cell-containing matrix may be at least about 100 µm or more. The 3D cell-containing matrix may be at least about 1000 µm or more. The 3D cell-containing matrix may be at least about 0.5 cm or more. The 3D cell-containing matrix may be at least about 1 cm or more. The 3D cell-containing matrix may be at least about 5 cm or more. The 3D cell-containing matrix may be at least about 10 cm or more.

The 3D cell-containing matrix may comprise an agent to promote growth of vasculature or nerves. The agent may be selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

Another aspect of the present disclosure provides a system for producing one or more immunological proteins, comprising a media chamber configured to contain a first medium comprising a first plurality of cells and a first plurality of polymer precursors. The system may comprise at least one energy source configured to direct at least one energy beam to the media chamber. The system may comprise one or more computer processors operatively coupled to the at least one energy source. The one or more computer processors may be individually or collectively programmed to receive computer instructions for printing a three-dimensional (3D) lymphoid organoid from computer memory. The one or more computer processors may be individually or collectively programmed to direct the at least one energy source to direct the at least one energy beam to the first medium in the media chamber along at least one energy beam path in accordance with the computer instruction, to subject at least a portion of the first polymer precursors to form at least a portion of the 3D lymphoid organoid. The one or more computer processors may be individually or collectively programmed to direct the at least one energy source to direct the at least one energy beam to a second medium in the media chamber along at least one energy beam path in accordance with the computer instructions, to subject at least a portion of the second medium in the media chamber to form at least a second portion of the 3D lymphoid organoid. The second medium may comprise a second plurality of cells and a second plurality of polymeric precursors. The second plurality of cells may be of a different type than the first plurality of cell. The one or more computer processors may be individually or collectively programmed to subject the first and second portions of the 3D lymphoid organoid to conditions sufficient to stimulate production of the one or more immunological proteins. The one or more computer processors may be individually or collectively further programmed to extract the one or more immunological proteins from the first and second portions of the 3D lymphoid organoid.

Figure 24:
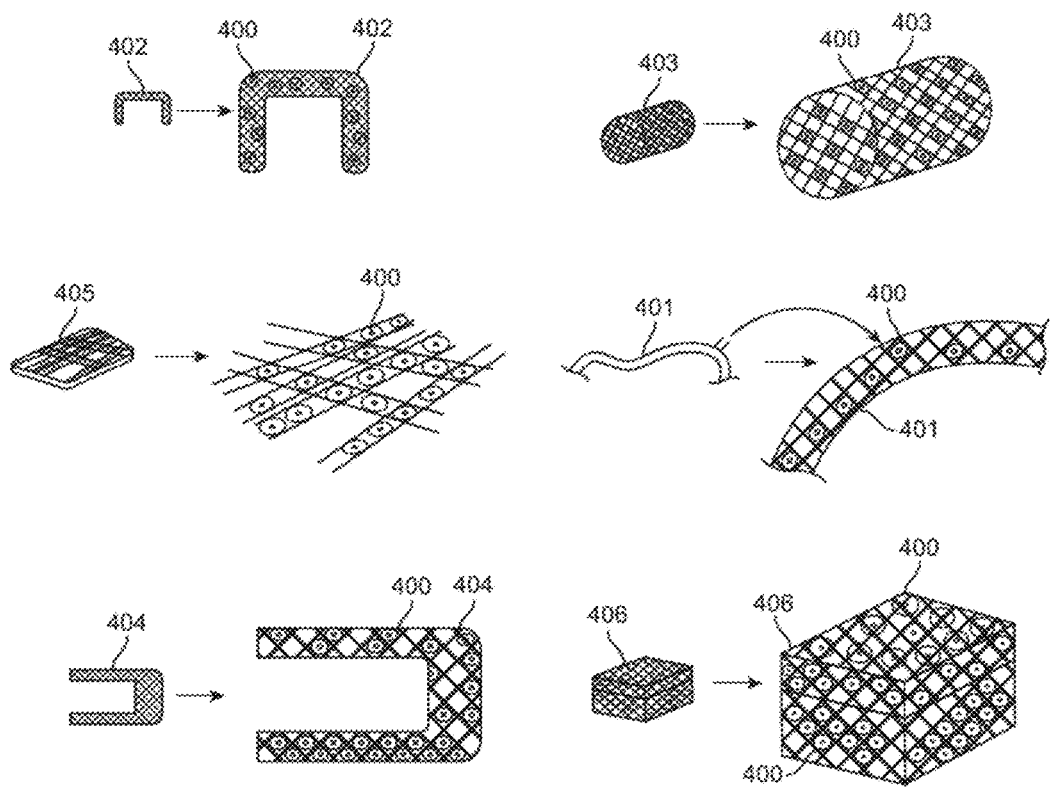
FIG. 24 illustrates examples of staples, sutures, stents and clips that contain cells for both dissolution and incorporation into tissue or promotion of tissue healing.

FIG. 24 illustrates devices and materials that may include cells 400 embedded within the materials that comprise the devices. Materials that may be used to print 3D cell-containing matrices or devices include degradable polymers, non-degradable polymers, biocompatible polymers, extracellular matrix components, bioabsorbable polymers, hydrogels, or any combination thereof. Non-limiting examples of bioasborbable polymers include polyesters, polyamino acids, polyanhydrides, polyorthoesters, polyurethanes, and polycarbonates. Non-limiting examples of biocompatible polymers include collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or a combination thereof. The biocompatible polymer may comprise an extracellular matrix component. Non-limiting examples of extracellular matrix components may include proteoglycans such as heparan sulfate, chondroitin sulfate, and keratan sulfate, non-proteoglycan polysaccharide such as hyaluronic acid, collagen, and elastin, fibronectin, laminin, nidogen, or any combination thereof. These extracellular matrix components may be functionalized with acrylate, diacrylate, methacrylate, cinnamoyl, coumarin, thymine, or other side-group or chemically reactive moiety to facilitate cross-linking induced directly by multi-photon excitation or by multi-photon excitation of one or more chemical doping agents. In some cases, photopolymerizable macromers and/or photopolymerizable monomers may be used in conjunction with the extracellular matrix components to create cell-containing structures. Non-limiting examples of photopolymerizable macromers may include polyethylene glycol (PEG) acrylate derivatives, PEG methacrylate derivatives, and polyvinyl alcohol (PVA) derivatives. In some instances, collagen used to create cell containing structure may be fibrillar collagen such as type I, II, III, V, and XI collagen, facit collagen such as type IX, XII, and XIV collagen, short chain collagen such as type VIII and X collagen, basement membrane collagen such as type IV collagen, type VI collagen, type VII collagen, type XIII collagen, or any combination thereof.

The biocompatible polymer may comprise other polymerizable monomers that are synthesized and not native to mammalian tissues, comprising a hybrid of biologic and synthetic materials. The biocompatible polymer may comprise a photoinitiator. Non-limiting examples of photoinitiators may include azobisisobutyronitrile (AIBN), benzoin derivatives, benziketals, hydroxyalkylphenones, acetophenone derivatives, trimethylolpropane triacrylate (TPT), acryloyl chloride, benzoyl peroxide, camphorquinone, benzophenone, thioxanthones, and 2-hydroxy-1-[4-(hydroxyethoxy)phenyl]-2-methyl-1-propanone. Hydroxyalkylphenones may include 4-(2-hydroxyethylethoxy)-phenyl-(2-hydroxy-2-methyl propyl) ketone (Irgacure® 295), 1-hidroxycyclohexyl-1-phenyl ketone (Irgacure® 184) and 2,2-dimethoxy-2-phenylacetophenone (Irgacure® 651). Acetophenone derivatives may include 2,2-dimethoxy-2-phenylacetophenone (DMPA). Thioxanthones may include isopropyl thioxanthone.

Once in place, the device may bring two pieces of tissue together, the cells may migrate within or out of the device, interact with other cells locally to promote healing and tissue remodeling around or within the cell containing bio-resorbable device. The cell-containing, bio-resorbable medical devices may be sutures 401 of any length or width, staples 402, stents 403 of any length or width, clips 404 which may be locking or compressible, patches and grafts 405 of arbitrary shapes and sizes, and/or similar structures intended to be used in a living subject. Single or multi-layered patches and grafts of arbitrary shape and size 406 can be created out of multiple different cells types to promote tissue development, augment tissue function, and/or healing. Patches and grafts may be made out of printed scaffolds that are porous or tubular in structure to allow for delivery of adequate nutrition for embedded cells via perfusion. Mesh patches can be used to improve elasticity and structural support for lymphatics, vasculature, and nerves, and thereby improving functionality of grafted tissue. Grafts may include but are not limited to: skin implant, uterine lining, neural tissue implant, bladder wall, intestinal tissue, esophageal lining, stomach lining, hair follicle embedded skin, retina tissue, or any combination thereof. Devices may be printed using synthetic or biological materials that may or may not mimic natural extracellular matrix scaffolding. Materials include but are not limited to polyethylene glycol diacrylate, collagen, gelatin laminin, fibrin, and/or alginate.

Figure 25:
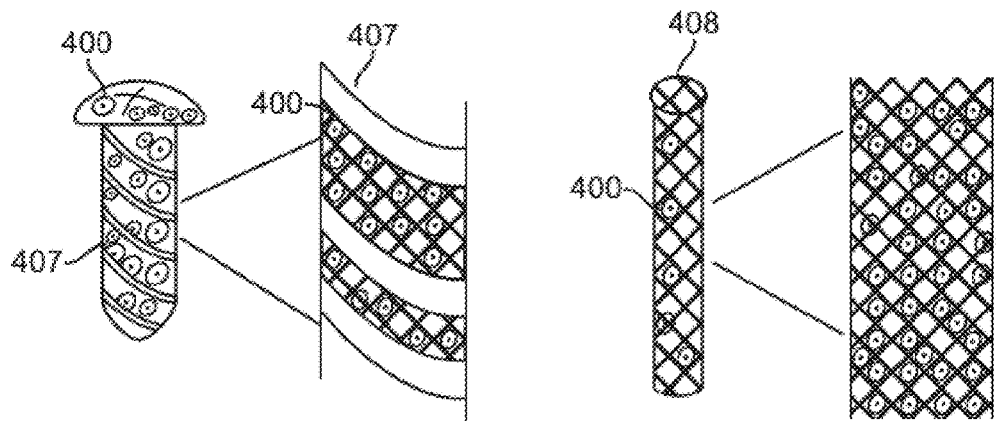
FIG. 25 illustrates examples of 3D printed bone-resorbable screws, pins, and grafts that may comprise cells.
Figure 26:
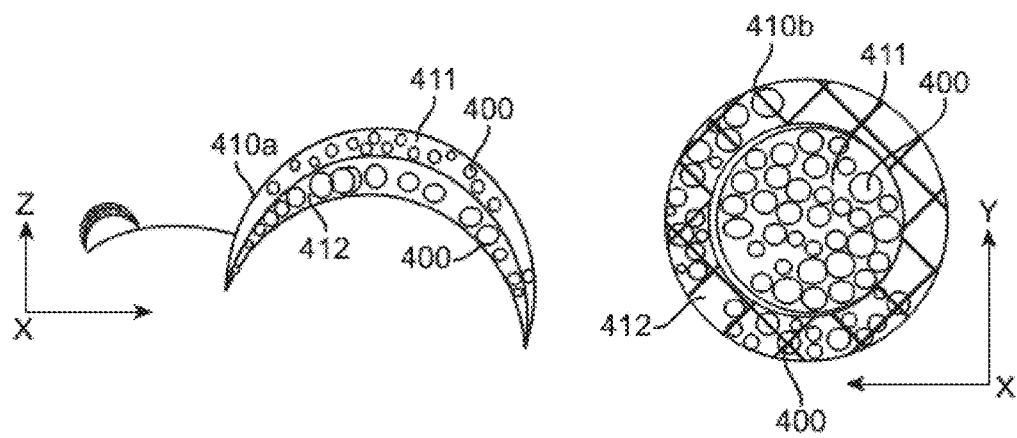
FIG. 26 illustrates examples of functional tissue implants that serve a functional augmentation by means of interaction with the cells and cellular systems closest to the implanted cell sites.

FIG. 25 illustrates bone-resorbable screws 407, pins 408, and other size or shape grafts with the purpose of holding tissue together, wound healing, while remaining implanted in the body. The examples illustrated in FIG. 25 may comprise cells. The holographically printed grafts and/or patches may comprise a variety of shapes, such as but not limited to oblong, rectangular, oval, any other polygonal shape, or any amorphous shape required to repair or reinforce the site of injury or disease. FIG. 26 illustrates a first mixed cell-seeded, holographically printed patch 410a and a second mixed cell-seeded, holographically printed patch 410b. The first and second mixed cell-seeded, holographically printed patches (i.e., 410a and 410b, respectively) may comprise cardiomyocytes 411 and/or stem cells 412, as shown in FIG. 26. The cell-seeded printed patches may comprise accessory cells including, but not limited to monocytes, fibroblasts, endothelial cells of various differentiation states, or any combination thereof.

To enhance the structural integrity of some devices three-dimensionally printed materials may be thicker or denser and may or may not contain cells at all sites. These cells when printed are trapped in any size aperture to keep cells in place, or allow them to move from the site in which they were originally printed and interact with other cells within their own layer, cells in subsequently or previously printed layers, or with cells in the native tissue that they are eventually implanted in. Cells encapsulated (FIG. 27), embedded, trapped, or contained 400 within a mesh net, lattice, matrix 414, framework of any aperture size 413 or density that allow cells to move through the apertures during the developmental process or be trapped in place. This makes up the base components of a larger structural architecture.

Three-dimensional lithography may be used to generate functional partial organs or organoids that may serve an augmenting or independent physiologic function not necessarily dependent upon site of implantation. Such three-dimensional lithography can be achieved by holographic projection of light through use of a two light modulating systems in series, as disclosed in commonly invented U.S. Provisional Patent Appl. No. 62/469,948, entitled MULTI-PHOTON TISSUE PRINTING, which is incorporated herein by reference Non-limiting examples of tissues for augmentation or replacement of function include kidney or generative models of kidney tissues, lung tissue or partial or full lung lobes and generative models therein, neural tissues, pancreatic tissues, insulin producing beta islets and associated tissues, thyroid tissues, splenic tissues, liver tissues, skin tissues, and tissues of the intestinal tract. All tissues listed necessarily include all structural components and accessory cells necessary to impart functional capabilities, included but not limited to, vasculature large and small as well as lymphatic drainage systems and all associated hollow structures, and nerve and, or immune cells necessary to impart functional capabilities.

In some embodiments, a printed kidney generative model is generated by the methods disclosed herein. The basic structural component of a kidney, including but not limited to: urine collecting ducts, vascularized and dense tissue surrounding urine collecting ducts, and kidney capsule may be separated into separate computer-aided design (CAD) files and printed sequentially, but in any order necessary, with automated computer control programs 1101. Printing may be achieved by signaling computer files to the laser printing system 110, and the structure that mimics the CAD files may be deposited sequentially, but in an order necessary, into the biogel and media chamber 122.

Three-dimensionally printed structures for implantation may be on the order of 1 micron to tens of centimeters or greater in volume. The surface area of complex tissue structures such as the lung take up several square meters and thus the external size of a large printed organ will be necessarily different from the surface area of the functional units. Therefore, the methods and systems provided herein may be designed to cover all structural components within the physiologic range of functional sizes and surface to volume ratios.

Laser-based holography may be used to near-instantaneously polymerize biomatrix materials in set patterns projected from computer aided design (CAD) files by a spatial light modulator or digital mirror device. Multiple print steps and positions may be required to build a full generative model.

Cells may be in any state of genetic or phenotypic differentiation, including undifferentiated, partially differentiated, fully differentiated. Examples of differentiation states include, but are not limited to pluripotent stem cells, totipotent stem cells. Cells may be autologous cells, sourced from a matched donor, cord blood, cell and tissue banks, or an established cell line. Multiple cell types at the same and/or different differentiation state may be used within a single print layer and/or multiple iterative print layers. Cells may be genetically manipulated prior to, during, and, or after the printing process via optical switch technology, clustered regularly interspaced short palindromic repeats (CRISPR) technology, introduction of virus, or other means of genetic manipulation. Genetic manipulation is not limited to nuclear DNA and may include mitochondrial DNA or free-floating plasmids or viral DNA not intended for incorporation into nuclear DNA.

Printed structures may comprise cells at high density or variable, including lop-sided cell densities or controlled densities of cells to promote cellular expansion or niche development in specific sites of the device. High or low cell density may be used depending on tissue product needs. Low cell density may be as low as 10,000 cells per cubic centimeter of printed material and as high as 1 Billion cells per cubic centimeter of printed materials. Cells may be of one type or mixed and printing may be performed in multiple layers.

Bioprinting materials may contain agents intended to promote growth of vasculature, including microvasculature, and nerves into the printed structure or into the surrounding native architecture. Additionally, printed biomaterials may contain agents intended promote differentiation of a stem or progenitor cell down a specified lineage. Such agents include but are not limited to: growth factors, cytokines, chemokines, antibiotics, anticoagulants, anti-inflammatory agents, opioid or non-opioid pain-relieving agents, immune-suppressing agents, immune-inducing agents, monoclonal antibodies, and/or stem cell proliferating agents.

Computer Systems

Figure 11:
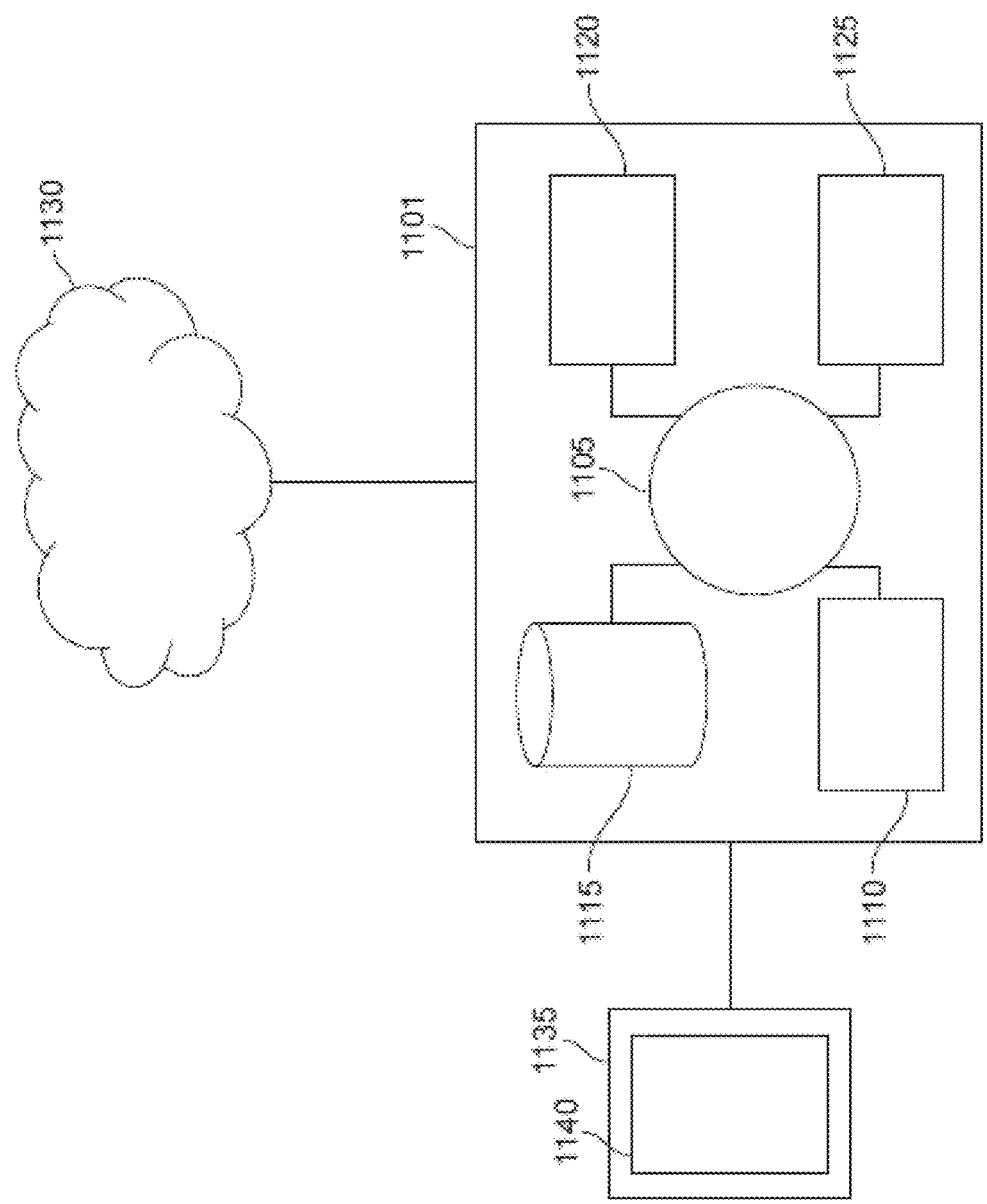
FIG. 11 shows a computer control system that is programmed or otherwise configured to implement methods provided herein.

The present disclosure provides computer control systems that are programmed to implement methods of the disclosure. FIG. 11 shows a computer system 1101 that is programmed or otherwise configured to receive a computer model of the 3D lymphoid organoid and/or 3D cell-containing matrix in computer memory; generate a point-cloud representation or lines-based representation of the computer model of the 3D lymphoid organoid and/or 3D cell-containing matrix in computer memory; and direct the at least one energy source to direct the energy beam to the medium in the media chamber along at least one energy beam path in accordance with the computer model of the 3D lymphoid organoid and/or 3D cell-containing matrix, and to subject at least a portion of the polymer precursors to form at least a portion of the 3D lymphoid organoid and/or 3D cell-containing matrix. The computer system 1101 can regulate various aspects of computer model generation and design, image generation, holographic projection, and light modulation of the present disclosure, such as, for example, receiving or generating a computer-aided-design (CAD) model of a desired three-dimensional (3D) biological material structure to be printed, such as a 3D lymphoid organoid and/or a 3D cell-containing matrix. The computer system 1101 can convert the CAD model or any other type of computer model such as a point-cloud model or a lines-based model into an image of the desired 3D lymphoid organoid and/or 3D cell-containing matrix to be printed. The computer system 1101 can project the image of the desired 3D lymphoid organoid and/or 3D cell-containing matrix holographically. The computer system 1101 can modulate a light source, an energy source, or an energy beam such that a light path or an energy beam path is created by the computer system 1101. The computer system 1101 can direct the light source, the energy source, or the energy beam along the light path or the energy beam path. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), cloud based computing services (e.g. Amazon Web Services), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, status of the printing process (e.g. displaying an illustration of the 3D lymphoid organoid and/or 3D cell-containing matrix representing the 3D tissue portions printed prior to completion of the process), manual controls of the energy beams (e.g. emergency stop buttons controlling the on/off states of the energy beam), and display indicators designed to e.g., display a remote oxygen concentration, a carbon dioxide concentration, a humidity measurement, and/or a temperature measurement within the media chamber. Examples of UI's include, without limitation, a graphical user interface (GUI) and web-based user interface.

PREFERRED EMBODIMENTS

In an aspect, the present disclosure provides a method for producing one or more immunological proteins, comprising: (a) providing a media chamber comprising a medium comprising (i) a plurality of cells and (ii) one or more polymer precursors; (b) directing at least one energy beam to said medium in said media chamber along at least one energy beam path that is patterned into a three-dimensional (3D) projection in accordance with computer instructions for printing a 3D lymphoid organoid in computer memory, to form at least a portion of said 3D lymphoid organoid comprising (i) at least a subset of said plurality of cells, and (ii) a polymer formed from said one or more polymer precursors; and (c) subjecting said at least said portion of said 3D lymphoid organoid to conditions sufficient to stimulate production of said one or more immunological proteins.

In some embodiments, the conditions comprise exposing said at least said portion of said 3D lymphoid organoid to an antigen in order to stimulate production of said one or more immunological proteins. In some embodiments, the antigen is selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. In some embodiments, the method further comprises: (d) extracting one or more immunological proteins from said at least portion of said 3D lymphoid organoid. In some embodiments, the one or more immunological proteins are human immunological proteins. In some embodiments, the immunological proteins are selected from the list consisting of antibodies, T-cell receptors and cancer immunotherapeutics. In some embodiments, the antibodies are IgG antibodies. In some embodiments, the IgG antibodies are human IgG antibodies. In some embodiments, the plurality of cells is from a subject. In some embodiments, the plurality of cells is selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. The T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of the 3D lymphoid organoid is selected from the list consisting of spherical, oval, ovate, ovoid, square, rectangular, cuboid, any polygonal shape, free-form, and tear-drop shape. In some embodiments, the 3D lymphoid organoid is a tear-drop shape. In some embodiments, the polymer of the at least of one portion of 3D lymphoid organoid forms a network. In some embodiments, the network is reticular, amorphous or a net. In some embodiments, the net is an organized net. In some embodiments, the organized net comprises a repeated pattern. In some embodiments, the amorphous network is designed to facilitate cellular interactions. In some embodiments, the cellular interactions are B cell to T cell conjugate formation, B cell to B cell interactions, B cell to macrophage, T cell to dendritic cell interactions, stromal cell interactions with T cells, stromal cell interactions with B cells or stromal cell interactions with dendritic cells. In some embodiments, the amorphous network is designed to facilitate movement between or within cellular niches.

In another aspect, the present disclosure provides a method for producing one or more immunological proteins, comprising (i) printing a three-dimensional (3D) lymphoid organoid comprising a matrix containing a plurality of cells, and (ii) treating said 3D lymphoid organoid to produce said one or more immunological proteins.

In some embodiments, the immunological proteins are selected from the list consisting of antibodies, T-cell receptors and cancer immunotherapeutics. In some embodiments, the antibodies are IgG antibodies. In some embodiments, the IgG antibodies are human IgG antibodies. In some embodiments, the plurality of cells is from said subject. In some embodiments, the plurality of cells is selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ.

In another aspect, the present disclosure provides a method for producing one or more immunological proteins, comprising: (a) providing a media chamber comprising a first medium, wherein said first medium comprises a first plurality of cells and a first polymeric precursor; (b) directing at least one energy beam to said first medium in said media chamber along at least one energy beam path in accordance with computer instructions for printing a three-dimensional (3D) lymphoid organoid in computer memory, to subject at least a portion of said first medium in said media chamber to form a first portion of said 3D lymphoid organoid; (c) providing a second medium in said media chamber, wherein said second medium comprises a second plurality of cells and a second polymeric precursor, wherein said second plurality of cells is of a different type than said first plurality of cells; (d) directing at least one energy beam to said second medium in said media chamber along at least one energy beam path in accordance with said computer instructions, to subject at least a portion of said second medium in said media chamber to form a second portion of said 3D lymphoid organoid; and (e) subjecting said first and second portions of said 3D lymphoid organoid to conditions sufficient to stimulate production of said one or more immunological proteins.

In some embodiments, the conditions comprise exposing said first and second portions of said 3D lymphoid organoid to an antigen in order to stimulate production of said one or more immunological proteins. In some embodiments, the antigen is selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. In some embodiments, the method further comprises: (f) extracting one or more immunological proteins from said first and second portions of said 3D lymphoid organoid. In some embodiments, the one or more immunological proteins are human immunological proteins. In some embodiments, the immunological proteins are selected from antibodies, T-cell receptors and cancer immunotherapeutics. In some embodiments, the antibodies are IgG antibodies. In some embodiments, the IgG antibodies are human IgG antibodies. In some embodiments, the first plurality of cells and said second plurality of cells are from a subject. In some embodiments, the first plurality of cells and said second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of said 3D lymphoid organoid is selected from the list consisting of spherical, oval, ovate, ovoid, square, rectangular, cuboid, any polygonal shape, free-form, and tear-drop shape. In some embodiments, the shape of said 3D lymphoid organoid is a tear-drop shape. In some embodiments, the polymer of said at least of said portion of 3D lymphoid organoid forms a network. In some embodiments, the network is reticular, amorphous or a net. In some embodiments, the net is an organized net. In some embodiments, the organized net comprises a repeated pattern. In some embodiments, the amorphous network is designed to facilitate cellular interactions. In some embodiments, the cellular interactions are B cell to T cell conjugate formation, B cell to B cell interactions, B cell to macrophage, T cell to dendritic cell interactions, stromal cell interactions with T cells, stromal cell interactions with B cells or stromal cell interactions with dendritic cells. In some embodiments, the amorphous network is designed to facilitate movement between or within cellular niches.

In another aspect, the present disclosure provides a method of producing one or more immunological proteins, comprising (i) printing a three-dimensional (3D) lymphoid organoid comprising a matrix containing a first plurality of cells and a second plurality of cells, and (ii) treating said 3D lymphoid organoid to produce said one or more immunological proteins.

In some embodiments, the immunological proteins are selected from the list consisting of antibodies, T-cell receptors and cancer immunotherapeutics. In some embodiments, the antibodies are IgG antibodies. In some embodiments, the IgG antibodies are human IgG antibodies. In some embodiments, the first and said second plurality of cells are from said subject. In some embodiments, the first and said second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ.

In another aspect, the present disclosure provides a method for using a three-dimensional (3D) cell-containing matrix, comprising: (a) providing a media chamber comprising a medium comprising (i) a plurality of cells and (ii) one or more polymer precursors; (b) directing at least one energy beam to said medium in said media chamber along at least one energy beam path that is patterned into a three-dimensional (3D) projection in accordance with computer instructions for printing said 3D cell-containing medical device in computer memory, to form at least a portion of said 3D cell-containing matrix comprising (i) at least a subset of said plurality of cells, and (ii) a polymer formed from said one or more polymer precursors; and (c) positioning said 3D cell-containing matrix in a subject.

In some embodiments, the plurality of cells is from said subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D cell-containing matrix forms suture, stent, staple, clip, strand, patch, graft, sheet, tube, pin, or screws. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 μm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a method of using a three-dimensional (3D) cell-containing matrix, comprising (i) printing the 3D cell-containing matrix comprising a plurality of cells, and (ii) positioning said 3D cell-containing matrix in a subject.

In some embodiments, the plurality of cells is from said subject. In some embodiments, the follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a method for using a three-dimensional (3D) cell-containing matrix, comprising: (a) providing a media chamber comprising a first medium, wherein said first medium comprises a first plurality of cells and a first polymeric precursor; (b) directing at least one energy beam to said first medium in said media chamber along at least one energy beam path in accordance with computer instructions for printing said 3D cell-containing matrix in computer memory, to subject at least a portion of said first medium in said media chamber to form a first portion of said 3D cell-containing matrix; (c) providing a second medium in said media chamber, wherein said second medium comprises a second plurality of cells and a second polymeric precursor, wherein said second plurality of cells is of a different type than said first plurality of cells; (d) directing at least one energy beam to said second medium in said media chamber along at least one energy beam path in accordance with said computer instructions, to subject at least a portion of said second medium in said media chamber to form a second portion of said 3D cell-containing matrix; and (e) positioning said first and second portions of said 3D cell-containing matrix in a subject.

In some embodiments, the first and said second plurality of cells is from said subject. In some embodiments, the first and said second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In an aspect, the present disclosure provides a method of using a three-dimensional (3D) cell-containing matrix, comprising (i) printing the 3D cell-containing matrix comprising a first plurality of cells and a second plurality of cells, wherein said first plurality of cells is different from said second plurality of cells, and (ii) positioning said 3D cell-containing matrix in a subject.

In some embodiments, the first and second plurality of cells are from said subject. In some embodiments, the first and second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D cell-containing matrix forms a suture, stent, staple, clip, strand, patch, graft, sheet, tube, pin, or a screw. In some embodiments, the graft is selected from the list consisting of skin implant, uterine lining, neural tissue implant, bladder wall, intestinal tissue, esophageal lining, stomach lining, hair follicle embed skin and retina tissue. In some embodiments, the 3D cell-containing matrix is from about 1 µm to about 10 cm. In some embodiments, the 3D cell-containing matrix further comprises an agent to promote growth of vasculature or nerves. In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents.

In another aspect, the present disclosure provides a system for producing one or more immunological proteins, comprising: (a) a media chamber configured to contain a medium comprising a plurality of cells and one or more polymer precursors; (b) at least one energy source configured to direct at least one energy beam to said media chamber; and (c) one or more computer processors operatively coupled to said at least one energy source, wherein said one or more computer processors are individually or collectively programmed to (i) receive computer instructions for printing a three-dimensional (3D) lymphoid organoid from computer memory; (ii) direct said at least one energy source to direct said at least one energy beam to said medium in said media chamber along at least one energy beam path in accordance with said computer instructions, to subject at least a portion of said polymer precursors to form at least a portion of said 3D lymphoid organoid, and (iii) subject said at least portion of said 3D lymphoid organoid to conditions sufficient to stimulate production of said one or more immunological proteins.

In some embodiments, the conditions sufficient to stimulate production of said one or more immunological proteins comprises exposing said at least said portion of said 3D lymphoid organoid to an antigen in order to stimulate production of said one or more immunological proteins. In some embodiments, the antigen is selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. In some embodiments, the one or more computer processors are individually or collectively further programmed to extract one or more immunological proteins from said at least portion of said 3D lymphoid organoid. In some embodiments, the one or more immunological proteins are human immunological proteins. In some embodiments, the immunological proteins are selected from the list consisting of antibodies, T-cell receptors and cancer immunotherapeutics. In some embodiments, the antibodies are IgG antibodies. In some embodiments, the IgG antibodies are human IgG antibodies. In some embodiments, the plurality of cells is from a subject. In some embodiments, the plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of said 3D lymphoid organoid is selected from the list consisting of spherical, oval, ovate, ovoid, square, rectangular, cuboid, any polygonal shape, free-form, and tear-drop shape. In some embodiments, the shape of said 3D lymphoid organoid is a tear-drop shape. In some embodiments, the polymer of said at least of said portion of 3D lymphoid organoid forms a network. In some embodiments, the network is reticular, amorphous or a net. In some embodiments, the net is an organized net. In some embodiments, the organized net comprises a repeated pattern. In some embodiments, the amorphous network is designed to facilitate cellular interactions. In some embodiments, the cellular interactions are B cell to T cell conjugate formation, B cell to B cell interactions, B cell to macrophage, T cell to dendritic cell interactions, stromal cell interactions with T cells, stromal cell interactions with B cells or stromal cell interactions with dendritic cells. In some embodiments, the amorphous network is designed to facilitate movement between or within cellular niches.

In another aspect, the present disclosure provides a system for producing one or more immunological proteins, comprising: (a) a media chamber configured to contain a first medium comprising a first plurality of cells and a first plurality of polymer precursors; (b) at least one energy source configured to direct at least one energy beam to said media chamber; and (c) one or more computer processors operatively coupled to said at least one energy source, wherein said one or more computer processors are individually or collectively programmed to (i) receive computer instructions for printing a three-dimensional (3D) lymphoid organoid from computer memory, (ii) direct said at least one energy source to direct said at least one energy beam to said first medium in said media chamber along at least one energy beam path in accordance with said computer instruction, to subject at least a portion of said first polymer precursors to form at least a portion of said 3D lymphoid organoid; (iii) direct said at least one energy source to direct said at least one energy beam to a second medium in said media chamber along at least one energy beam path in accordance with said computer instructions, to subject at least a portion of said second medium in said media chamber to form at least a second portion of said 3D lymphoid organoid, wherein said second medium comprises a second plurality of cells and a second plurality of polymeric precursors, wherein said second plurality of cells is of a different type than said first plurality of cell; and (iv) subject said first and second portions of said 3D lymphoid organoid to conditions sufficient to stimulate production of said one or more immunological proteins.

In some embodiments, the conditions sufficient to stimulate production of said one or more immunological proteins comprises exposing said first and second portions of said 3D lymphoid organoid to an antigen in order to stimulate production of said one or more immunological proteins. In some embodiments, the antigen is selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. In some embodiments, the one or more computer processors are individually or collectively further programmed to extract said one or more immunological proteins from said first and second portions of said 3D lymphoid organoid. In some embodiments, the one or more immunological proteins are human immunological proteins. In some embodiments, the one or more immunological proteins are selected from antibodies, T-cell receptors and cancer immunotherapeutics. In some embodiments, the antibodies are IgG antibodies. In some embodiments, the IgG antibodies are human IgG antibodies. In some embodiments, the first plurality of cells and said second plurality of cells are from a subject. In some embodiments, the first plurality of cells and said second plurality of cells are selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. In some embodiments, the B cells are selected from the list consisting of naïve B cells, mature B cells, plasma B cells, B1 B cells and B2 B cells. In some embodiments, the T cells are selected from the list consisting of CD8+ and CD4+. In some embodiments, the 3D lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of said 3D lymphoid organoid is selected from the list consisting of spherical, oval, ovate, ovoid, square, rectangular, cuboid, any polygonal shape, free-form, and tear-drop shape. In some embodiments, the shape of said 3D lymphoid organoid is a tear-drop shape. In some embodiments, the polymer of said at least of said portion of 3D lymphoid organoid forms a network. In some embodiments, the network is reticular, amorphous or a net. In some embodiments, the net is an organized net. In some embodiments, the organized net comprises a repeated pattern. In some embodiments, the amorphous network is designed to facilitate cellular interactions. In some embodiments, the cellular interactions are B cell to T cell conjugate formation, B cell to B cell interactions, B cell to macrophage, T cell to dendritic cell interactions, stromal cell interactions with T cells, stromal cell interactions with B cells or stromal cell interactions with dendritic cells. In some embodiments, the amorphous network is designed to facilitate movement between or within cellular niches.

In another aspect, the present disclosure provides a method of producing a population of human immunological proteins, comprising: using a multi-photon laser bio-printing system to bio-print a three-dimensional lymphoid organoid; exposing said three-dimensional lymphoid organoid to an antigen in order to stimulate production of said population of human immunological proteins; and extracting said population of human immunological proteins from said three-dimensional lymphoid organoid.

In some embodiments, the antigen is selected from the list consisting of whole peptides, partial peptides, glycopeptides, whole proteins or protein subunits, carbohydrates, nucleic acids, live virus, heat-killed virus, viral particles, membrane bound or stabilized proteins, phage displayed antigens and whole cells. In some embodiments, the population of human immunological proteins is selected from the list consisting of antibodies, T-cell receptors and cancer immunotherapeutics. In some embodiments, the antibodies are IgG antibodies. In some embodiments, the three-dimensional lymphoid organoid is selected from the list consisting of a B cell germinal center, a thymic-like development niches, a lymph node, an islet of Langerhans, a hair follicle, a tumor, tumor spheroid, a neural bundle or support cells, a nephron, a liver organoid, an intestinal crypt, a primary lymphoid organ and a secondary lymphoid organ. In some embodiments, the shape of said three-dimensional lymphoid organoid is selected from the list consisting of spherical, oval, ovate, ovoid, square, rectangular, cuboid, any polygonal shape, free-form, and tear-drop shape. In some embodiments, the shape of said three-dimensional lymphoid organoid is tear-drop shape.

EXAMPLES

The following examples are provided for illustrative purposes. These examples are not intended to be limiting.

Example 1

Zika Virus Antibody Generation in Printed Lymph Organoids

In an example, an in vitro study was conducted to generate antibodies targeting the Zika virus using printed lymph organoids, as described in the methods disclosed herein. A total of 50 lymph node organoids were used to generate Zika virus antibodies. Hybridoma cell lines were generated within 6 weeks.

Figure 22:
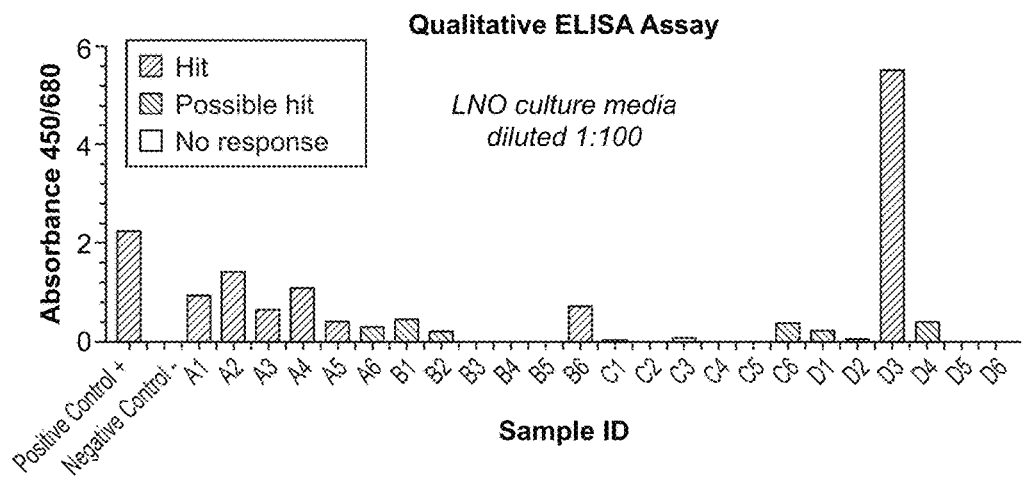
FIG. 22 shows enzyme-linked immunosorbent assay (ELISA) results of a Zika antibody generation study in a printed lymph organoid.

As shown in FIG. 22, 24 different antibodies (samples A1-A6, B1-B6, C1-C6, and D1-D6) were exposed to an ELISA plate and their absorbance at 450 nm and 680 nm wavelengths was measured. Samples A1-A6, B1, B2, B6, C6, D1, D3, and D4 exhibited higher absorbance values than the negative control. Sample D3 exhibited a higher absorbance value than the positive control. This study demonstrated the lymph node organoids produced by the methods described herein are capable of successful high-throughput generation of antibody libraries that bypass the use of animals in antibody generation.

Example 2

Zika Virus Antibody In Vivo Study

In another example, a murine, in vivo study is conducted to assess the infectious virus neutralization capabilities of antibodies produced by lymph node organoids produced by the methods disclosed herein. First, a library of antibodies is produced in printed lymph node organoids. The best antibody candidates are selected via ELISA testing (i.e. samples with the highest absorbance values). Genetic sequencing of the best antibody candidates is performed. Additionally, the antibody affinities for whole Zika virus are determined via surface plasmon resonance (SPR) (Biacore™ 8 K, GE Healthcare). The antibody that shows the best binding affinity to the Zika virus is tested in mice infected with the Zika virus and shows a potent neutralizing activity.

Example 3

Figure 28C:
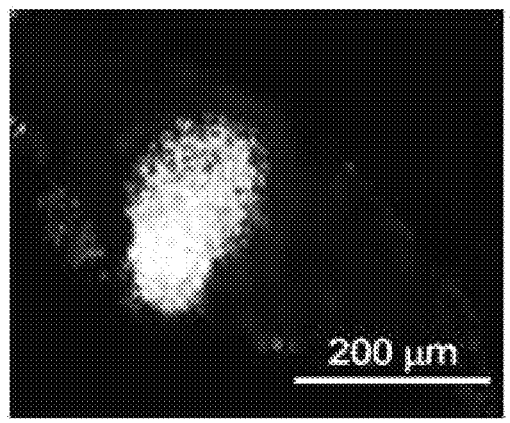
Figure 28D:
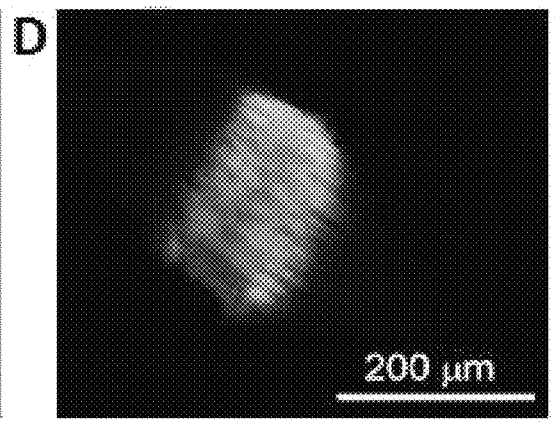
Figure 28E:
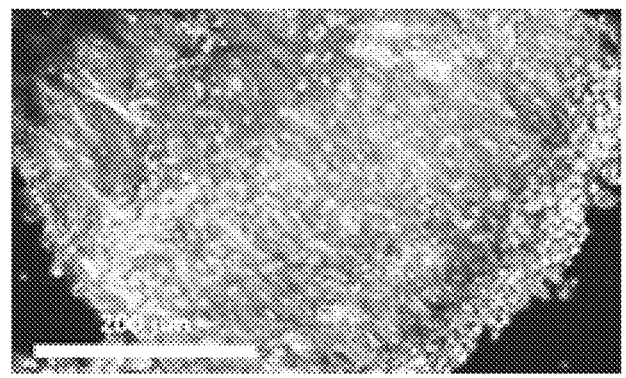

Clusters of Encapsulated Human Pluripotent Stem Cell-Derived Insulin-Producing Cells In another example, clusters of human derived insulin producing cells were encapsulated with the holographic printing methods described herein. The 3D printed clusters of human-derived insulin-producing cells may be used for the purpose of endocrine cell delivery or for implantation. FIG. 28A shows a cluster of about 1,500 human pluripotent stem cell (PSC)-derived, insulin-producing cells expressing enhanced green fluorescent protein (eGFP) under the insulin promoter. The human PSC-derived, insulin-producing cells were encapsulated and recovered using the three-dimensional holographic printing methods and systems provided. Encapsulated cells are shown in bright field microscopy images on the left panels of FIG. 28A. Encapsulated cells are shown in fluorescent microscopy images (green-channel fluorescence) on the right panels of FIG. 28A, where both the structure and the cells emitted some fluorescence indicating encapsulation. Cells were encapsulated 5 days prior to imaging and demonstrated robust eGFP fluorescence. As shown in FIG. 28B, the amount of human C-peptide (in nanomoles per milliliters) in encapsulated cells five days post-encapsulation was measured in the media containing an average of 10 encapsulated insulin producing elements. C-peptide is normally produced by β cells alongside insulin. FIGS. 28C and 28D show fluorescent microscopy images of encapsulated cells five days after encapsulation. The encapsulated cells expressed eGFP fluorescence under the insulin promoter demonstrating that encapsulation is still intact in after 5 days. FIG. 28E shows a high resolution fluorescent microscopy image of the encapsulating structure for the delivery and maintenance of cells. Scale bars are 200 µm.

Example 4

3D, Holographically Printed Biocompatible Micro-stent

Figure 29A:
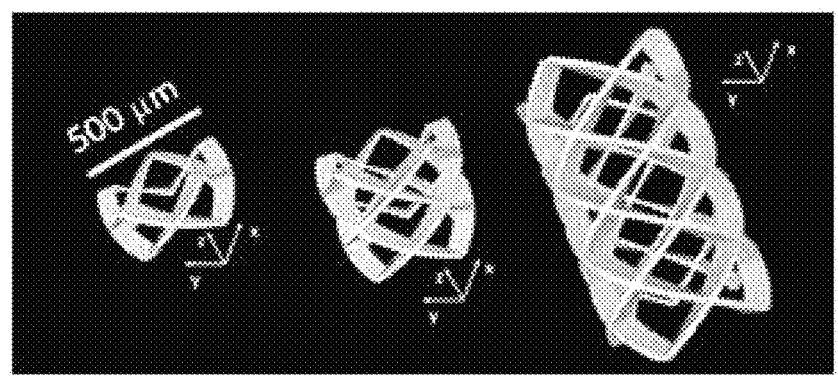
FIGS. 29A-29C show a biocompatible micro-stent structure generated by holographic printing.
Figure 29B:
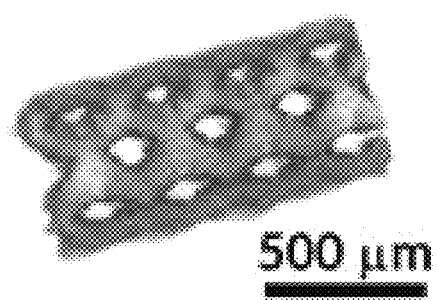
Figure 29C:
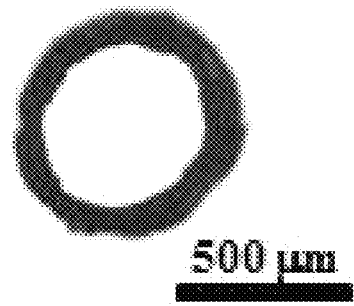

In another example, a biocompatible micro-stent was printed using the methods and systems described herein. FIG. 29A shows a representative, 3D rendering of a stackable stent structure that can be used to print small biocompatible stent structures of varied lengths. FIG. 29B is a microscopy image showing a side view of a 1 millimeter (mm) long, flexible, and porous stent structure printed using the methods and systems provided herein. Scale bar is 500 µm. FIG. 29C is a microscopy image showing a cross-section of the flexible stent structure demonstrating circular integrity and a hollow design. The image was taken looking through the center of the hollow interior of the stent structure. Scale bar is 500 µm.

Example 5

3D, Holographically Printed Micro-Stent Compressibility and Resilience Tests

In another example, a biocompatible micro-stent, printed using the methods and systems described herein, was tested for its compressibility and resilience. FIG. 30A shows a series of five still images from a video depicting repeated compression of the 500 microns (µm) diameter stent against a solid surface. Scale bar is 200 µm. FIG. 30A shows the same series of five still images from FIG. 30A; however, bars have been added to the images to demonstrate the degree of compression and resilience of the stent. The stent was compressed to varying degrees ranging from at least about 200 microns. As shown in FIGS. 30A and 30B, the stent structure returned to its original dimensions (i.e., diameter) after compression with no observed structural defects. Scale bars are 200 micrometers (µm).

Example 6

3D, Holographically Printed Micromesh

Figure 31A:
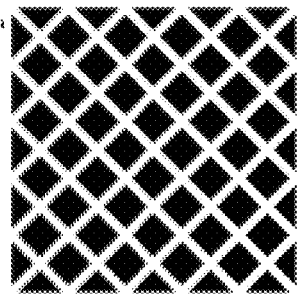
FIGS. 31A-31E show a three-dimensional, holographically printed micromesh network.
Figure 31B:
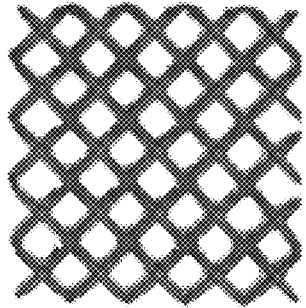
Figure 31C:
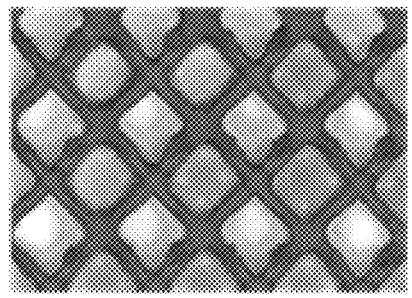
Figure 31D:
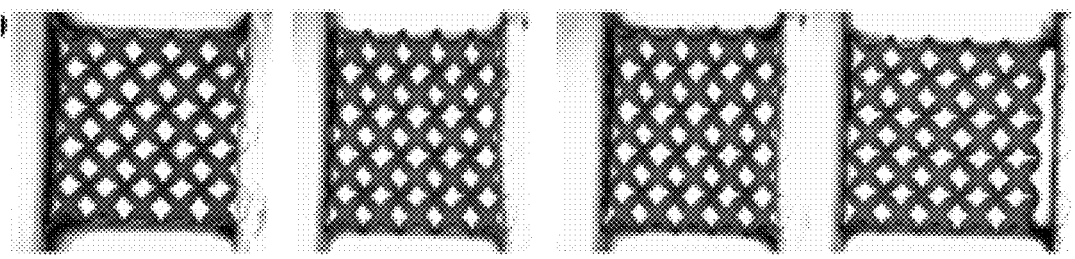
Figure 31E:
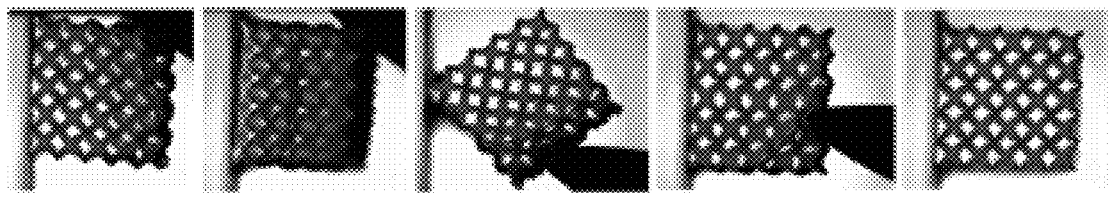

In another example, a micromesh was printed using the methods and systems described herein. FIG. 31A shows a computer-generated image of a micromesh network to be printed holographically. FIG. 31B shows a holographically printed mesh network. Scale bar is 500 µm. FIG. 31C shows a close up image of the mesh network shown in FIG. 31B. Scale bar is 250 µm. FIG. 31D shows a series of still images from a video where the micromesh was subjected to lateral compression. FIG. 31D thus demonstrates the flexibility and resiliency of the micromesh. FIG. 31E shows a series of still images from a video showing the micromesh as it is handled with tweezers. FIG. 31E demonstrates the flexibility and resiliency of the micromesh.

Example 7

Compartmentalized Antigen-Responsive Human Immune Tissue: Lymph Node Organoid

Figure 32A:
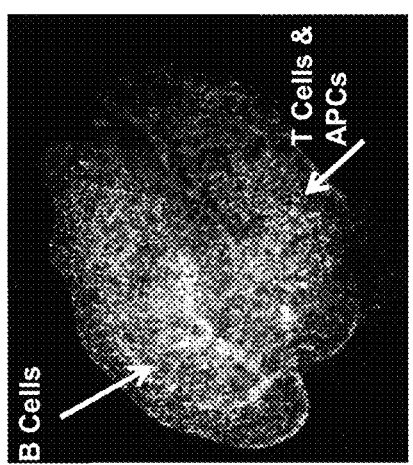
FIGS. 32A-32H show images of printed lymph node organoids (LNO) and characterization of their function.
Figure 32B:
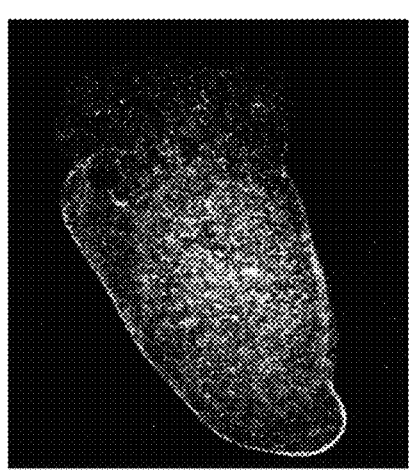
Figure 32C:
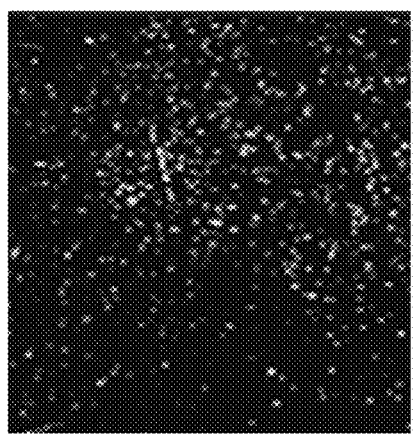
Figure 32D:
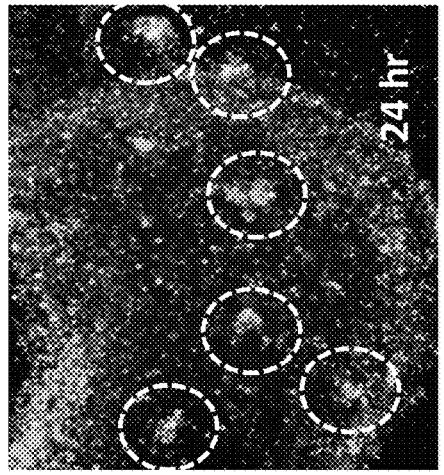
Figure 32E:
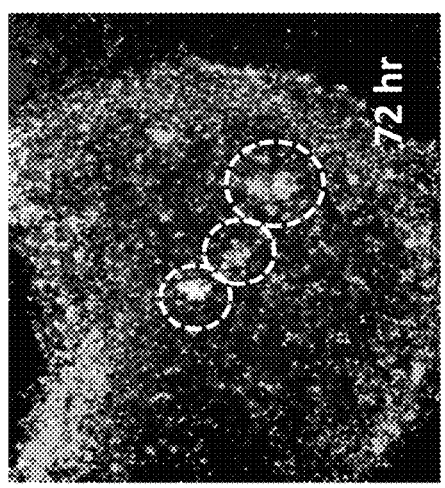
Figure 32F:
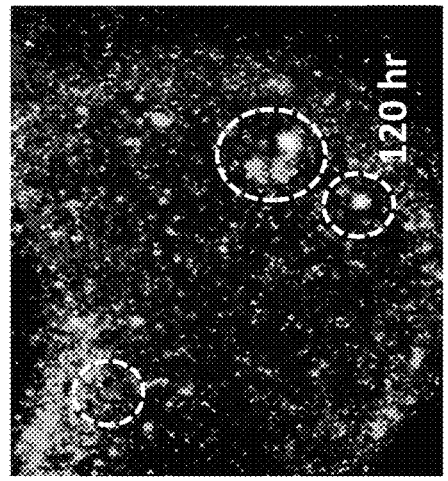
Figure 32G:
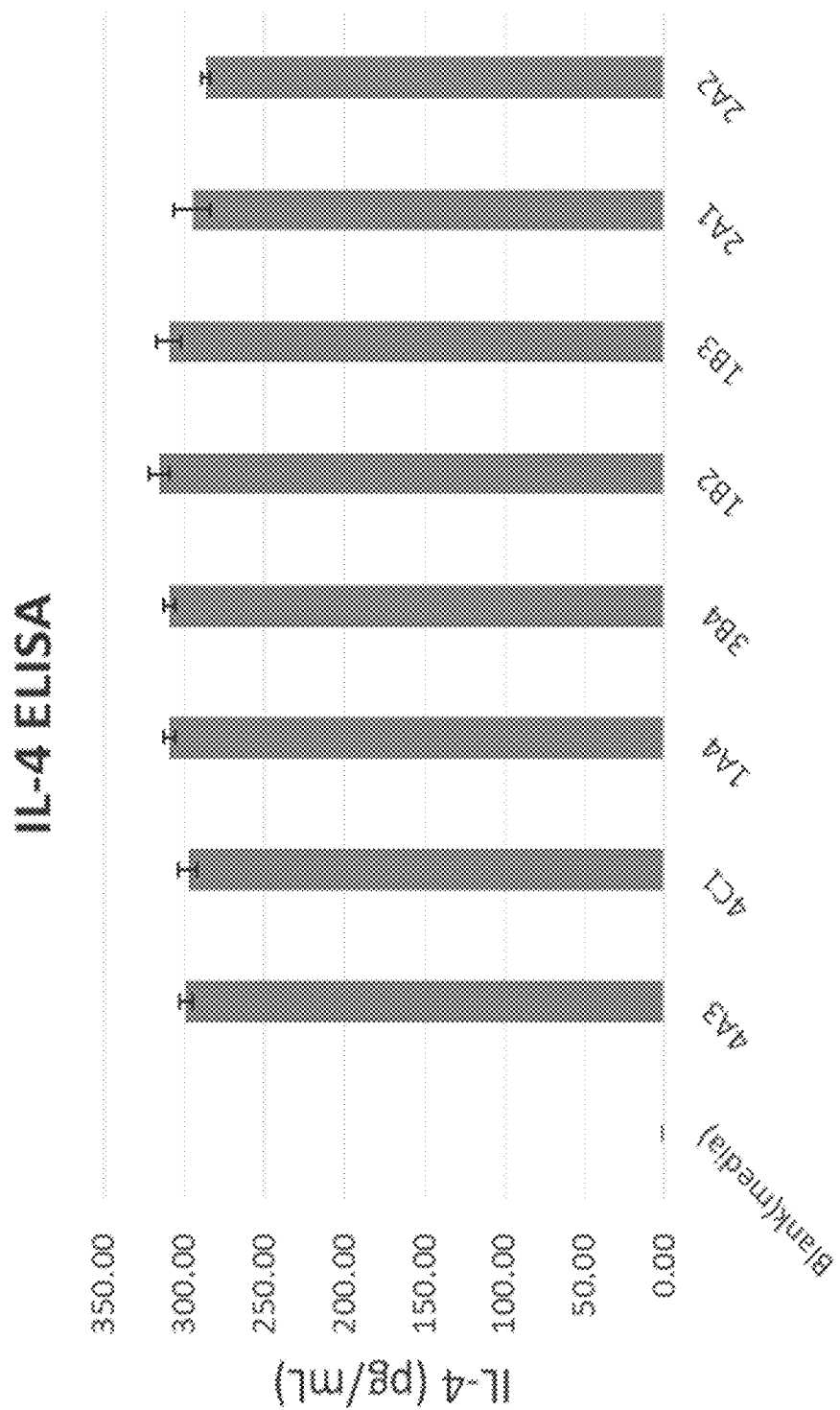
Figure 32H:
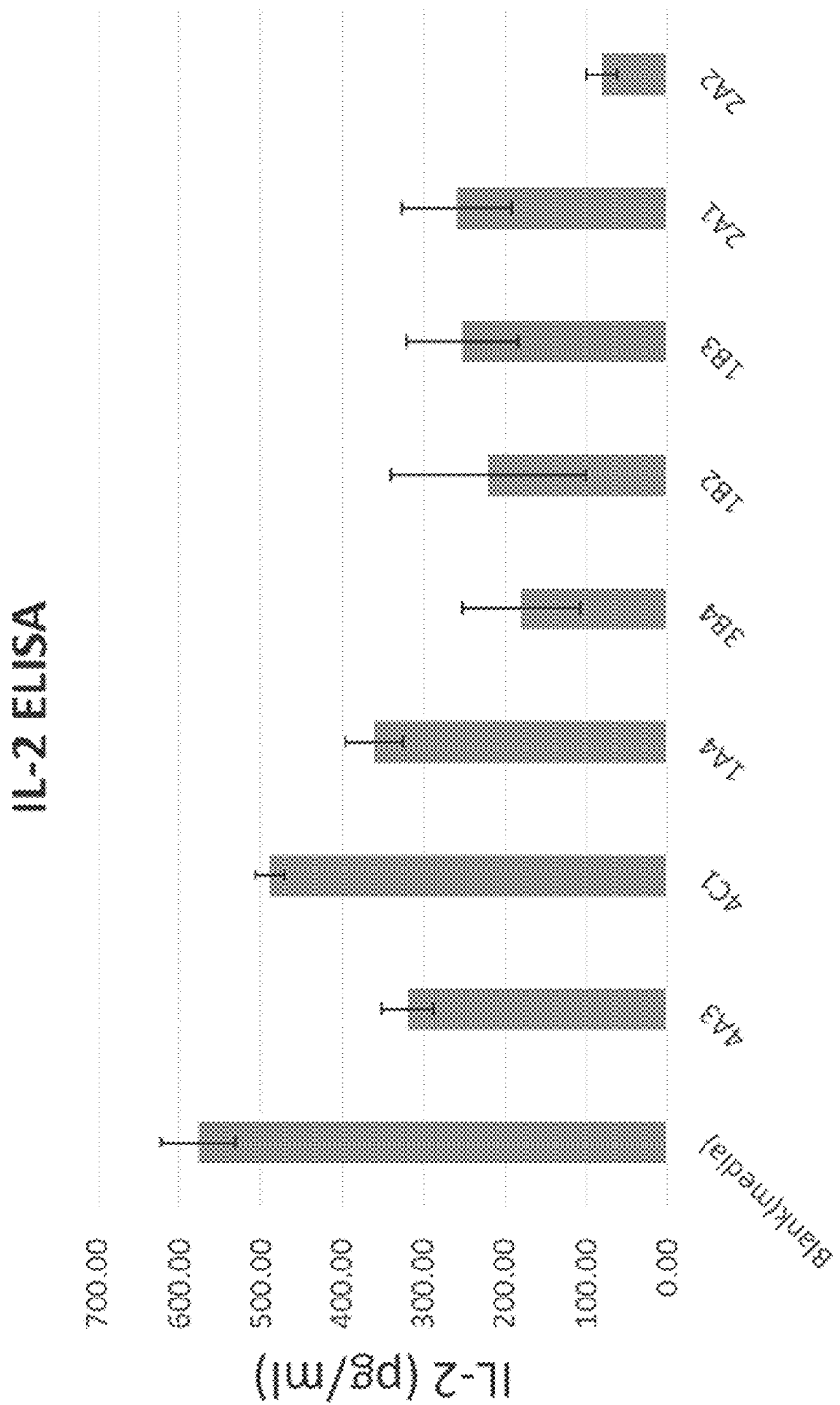

In another example, a lymph node organoid using the methods and systems provided herein and its function was assessed. FIG. 32A shows a fluorescent microscopy image of segregated immune cells at a density of 20 million cells per milliliter in a polymerized 1.5 mg/mL collagen matrix. A mixture of antigen presenting cells (APCs) and T cells was printed in a way that interfaces with a printed collagen matrix containing B cells from the same donor. FIG. 32B shows a fluorescent microscopy image representing the mixed cell population in the printed collagen matrix. The mixed cell population comprised B cells and T cells, and the collagen matrix was printed with a 1.5 mg/mL collagen concentration. FIG. 32C shows a fluorescent microscopy image of the population of mixed cells in a tissue culture well. This population of mixed cells was not printed in a matrix of collagen or other material; thus, demonstrating a lower concentration of cells and a mixed distribution. FIG. 32D shows a fluorescent microscopy image of lymph node organoids and clusters of cells 24 hours after the addition of antigen to the lymph node organoids. Clusters of cells from both the T and B cell zone, represented by different colors, formed, indicating interactions and direct cell-cell contact occurs within the lymph node organoid (cell clusters are circled in FIG. 32D). FIG. 32E shows a fluorescent microscopy image of the printed lymph node organoids and cells clusters 72 hours after a single antigen pulse. FIG. 32F shows a fluorescent microscopy image of the printed lymph node organoids and cells clusters 120 hours after a single antigen pulse. The cell clusters remained formed and shifted locations after both 72 and 120 hours post-antigen addition, indicating dynamic and motile cells within the organoid (cell clusters are circled in FIGS. 32E-32F). FIG. 32G shows a graph representing the production of interleukin-4 (IL-4) in picograms per milliliter (pg/mL) as measured by an enzyme-linked immunosorbent assay (ELISA). Cytokine IL-4 was measured in media surrounding the organoid five days after the antigen challenge. IL-4 can be produced by B cells, T cells, and dendritic cells during their proliferation and in the course of response to an antigen. Media alone used to culture the organoid is the blank, control reading. Sample names 4A3, 4C1, 1A4, 3B4, 1B2, 1B3, 2A1, and 2A2 refer to different sampling locations (i.e., different wells of a tissue culture plate) in both FIGS. 32G and 32H. FIG. 32H shows a graph representing the production of IL-2 in pg/mL in media surrounding the organoid five days after the antigen challenge. Cell culture media supplemented with IL-2 was used to culture the printed lymph node organoids on day 0 of the antigen challenge. Results showed varied IL-2 amounts per well. The variation in the amounts of IL-2 may represent both consumption of IL-2 and production of IL-2 during the course of the antigen response. Media was not changed or added to the printed lymph node organoids throughout the five days after the antigen challenge (i.e., when production of IL-4 and IL-2 was measured).

Example 8

Figure 33A:
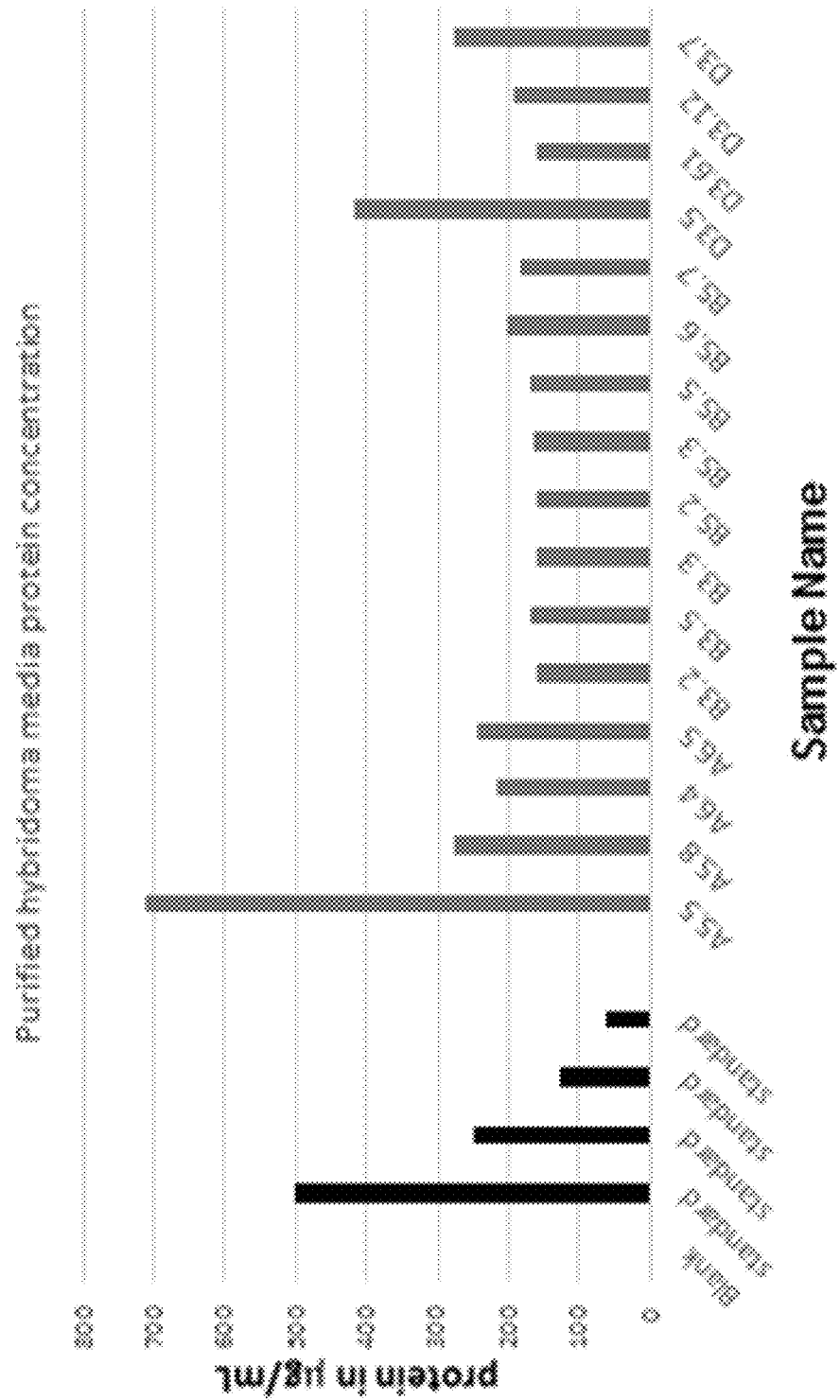
FIGS. 33A-33C show human immunoglobulin (IgG) purified from printed LNO.

Production of Human IgG by Human Lymph Node Organoids in Response to an Antigen Challenge In another example, lymph node organoids were printed and cultured in vitro. Human immunoglobulin (IgG) was purified from the lymph node organoid media and tested for the presence of protein. FIG. 33A shows a graph representing the concentration of protein in micrograms per milliliter (µg/mL) for the controls (i.e., blank and standards) and the various samples. High amounts of protein indicated the presence of secreted human IgG antibody; thus, indicating a functional immune response. Examples of purified (FIG.

Figure 33B:
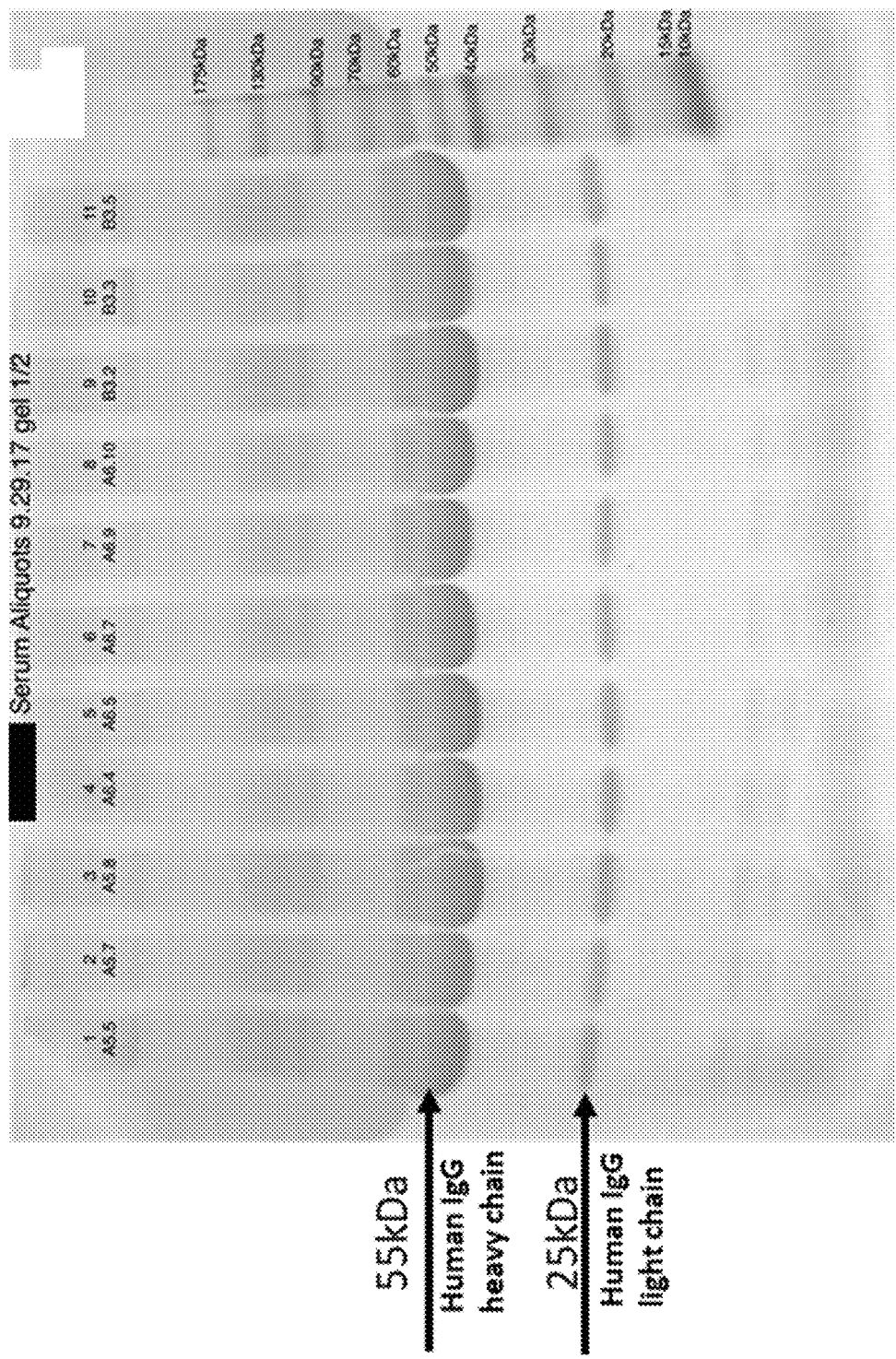
Figure 33C:
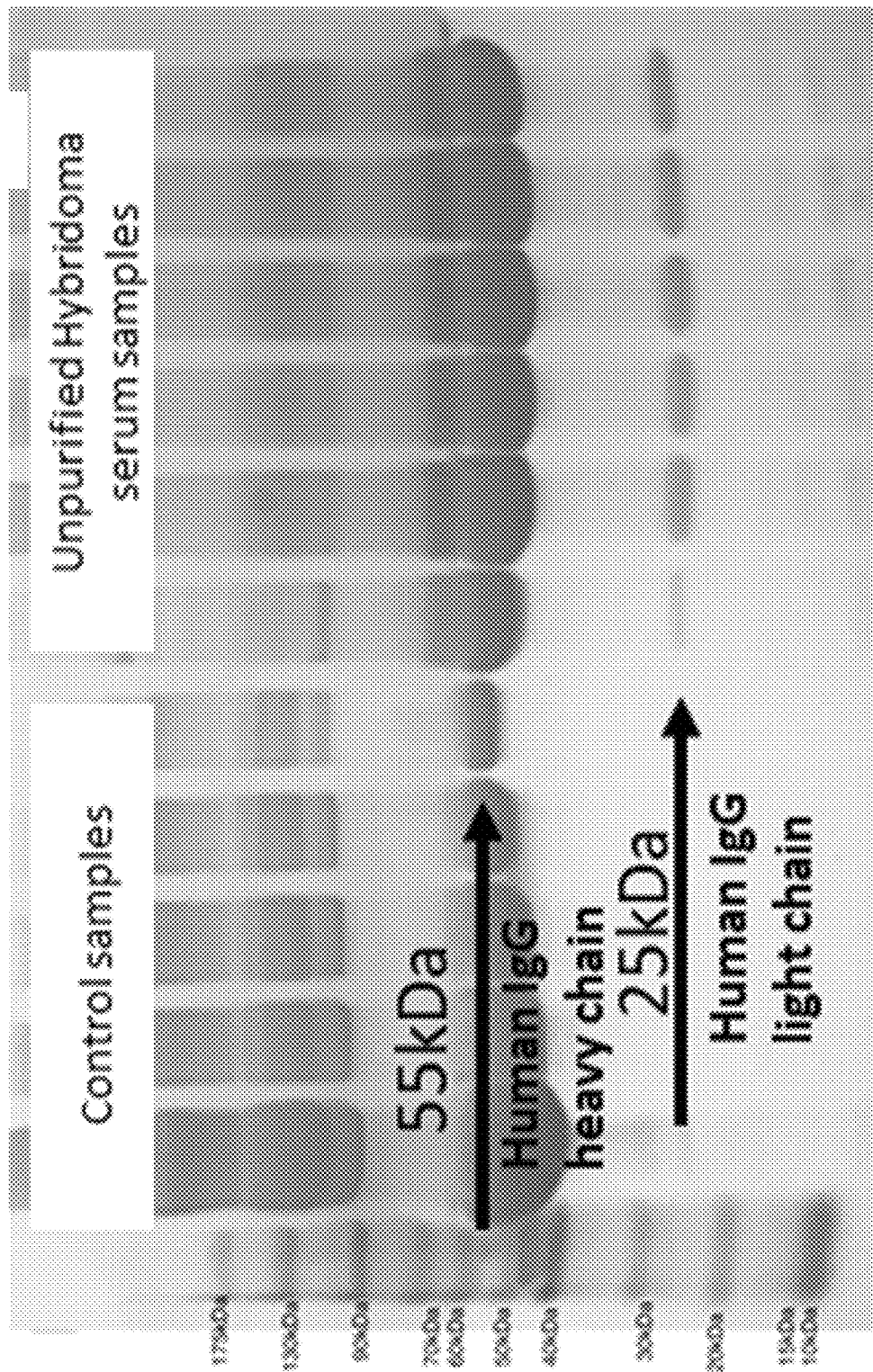

33B) and unpurified (FIG. 33C) human IgG isolated from the printed lymph node organoid media was run on a polyacrylamide gel using sodium dodecyl sulfate polyacrylamide gel electrophoresis (SDS-PAGE) for protein separation. FIG. 33B and FIG. 33C show images of gels containing purified human IgG (FIG. 33B) and purified human IgG (FIG. 33C) isolated from the printed lymph node organoid media. The images demonstrated clear bands at the expected molecular weights of about 25 kiloDaltons (kDa) for human IgG light chain and about 55 kDa for human IgG heavy chain.

Example 9

Validation of Antigen Specific Binding of Human IgG

Figure 34A:
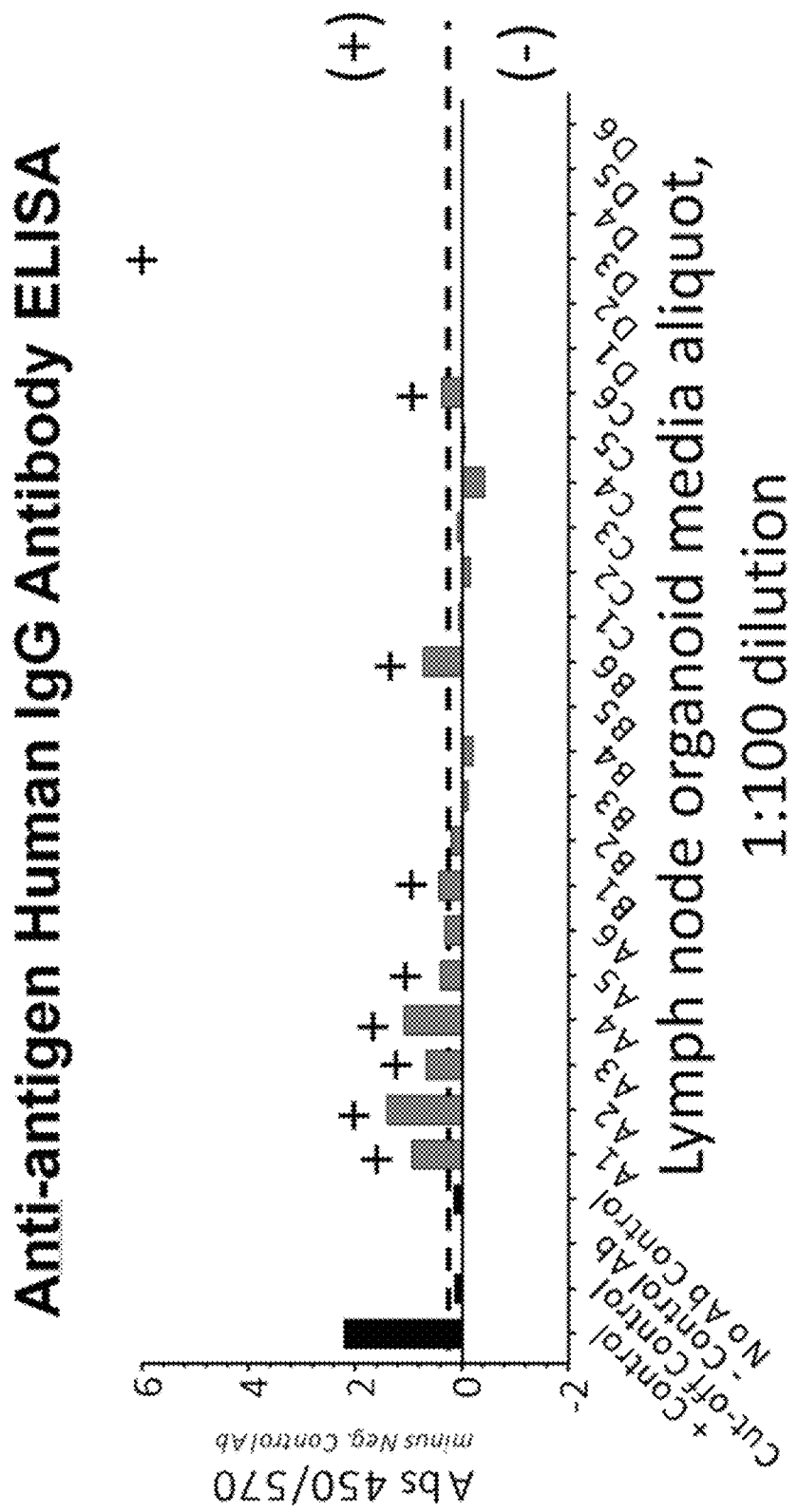
FIGS. 34A-34B show printed LNO culture media aliquots tested for reactivity of human IgG with the antigen used in an antigen challenge.
Figure 34B:
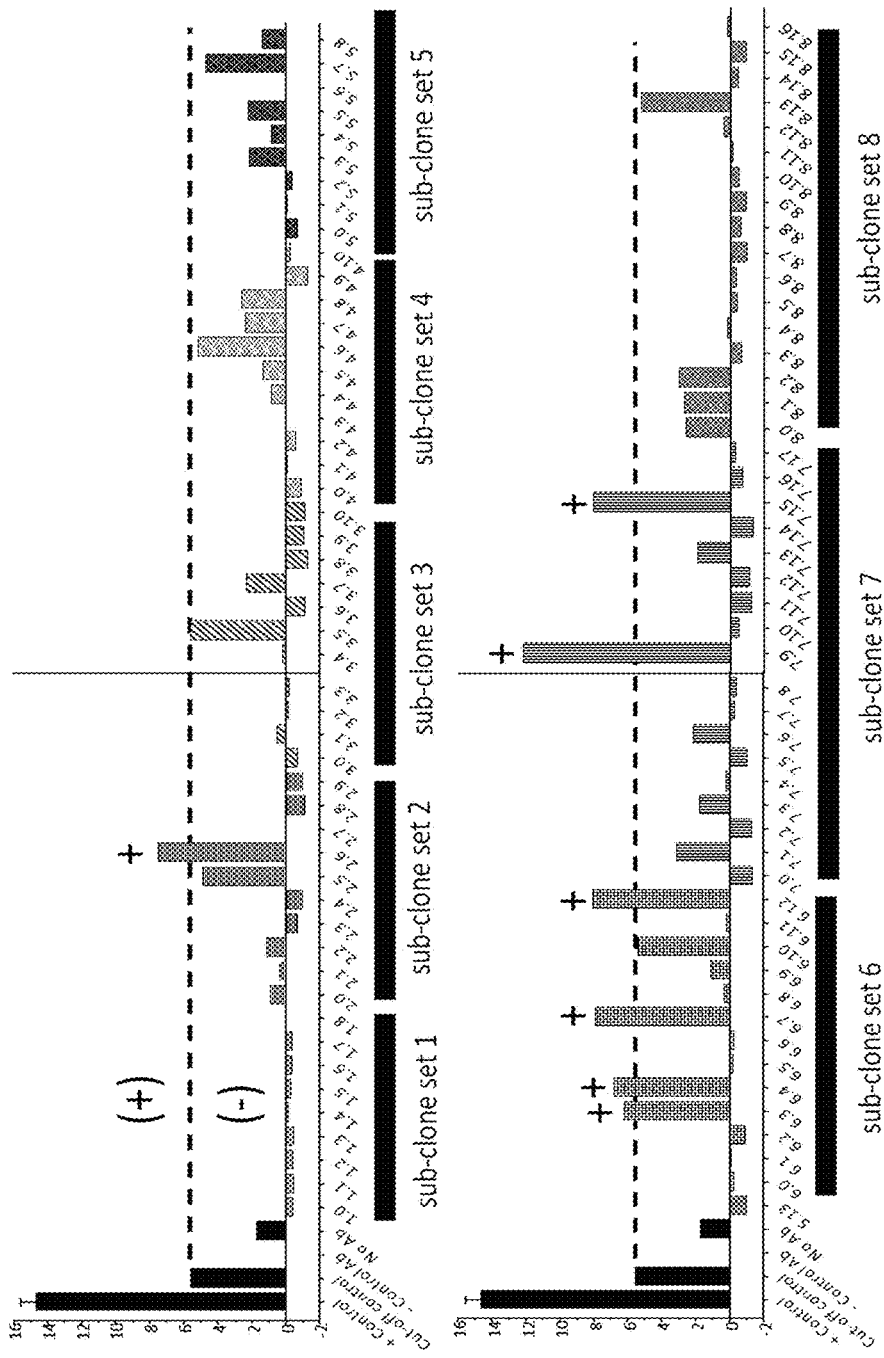

In another example, printed lymph node organoid culture media aliquots were tested for reactivity of human IgG with the antigen used in the antigen challenge described in Example 7. An enzyme-linked immunosorbent assay (ELISA) was used to detect class-switched Human IgG that was reactive to the specific antigen used to challenge the lymph node organoids. FIG. 34A shows a graph representing the absorbance (i.e., the optical density) at 450 nanometers (nm) and 570 nm of the samples tested using an ELISA. A high absorbance indicated the sample containing the human IgG was highly reactive to the specific antigen used in the antigen challenge. The ELISA was run with controls and samples that were direct aliquots of the printed lymph node organoid media, obtained 21 days after the initial antigen challenge. Organoids from positive antibody containing wells were then selected for creation of hybridomas. Dotted line represents cut-off for a positive antibody reading as denoted by the commercial kit. Plus symbols (+) denote unique antigen-specific positive wells in FIG. 34A. FIG. 34B shows two graphs representing sub-cloned unique hybridomas that were further assayed for the presence of specific antigen-reactive human IgG. Several positive clones were identified, such as Sub-Clone Set 2, Sub-Clone Set 6, and Sub-Clone Set 7. The dotted line represents a cut-off for a positive antibody reading as denoted by the commercial kit used. Plus symbols (+) denote unique antigen-specific IgG positive sub-cloned hybridomas in FIG. 34B.

Example 10

Printed Cell-Containing Mesh Patches to Improve Engineered Skin Grafts

In another example, a printed mesh network of patches is used to support highly stratified and multilayered skin tissue, including an avascular stratified epidermal layer and a vascularized dermal layer. Layers of cell-containing collagen (type 1) mesh networks are used to engineer a dermal layer. Cells seeded in the mesh networks include, but are not limited to fibroblasts, keratinocytes, and epidermal cells. Mesh networks comprise porous and tubular structures that allow for delivery of nutrients to the dermal layer via perfusion. Structures are incorporated into the mesh network supports vascular systems, nerve bundles and lymphatics, allowing for generation of functional and viable dermis that supports a stratified epidermal layer. On the upper most layers, structures are incorporated in order to support hair follicle and sebaceous gland micro niches that are populated with epidermal stem cells. Keratinocytes are cultured on top of dermal mesh patches and are induced to proliferate by established protocols. Proliferation of keratinocytes is induced by addition of exogenous factors, which include but are not limited to calcium, serum, and phorbol esters. Keratinocytes are grown at an air-liquid interface to induce the differentiation of fully stratified epidermis including basal, spinous, granular, and cornified skin layers containing hair follicle and sebaceous gland micro niches. Extra-cellular matrix components, growth factors and epithelial cells are placed in desired locations within or on the printed mesh patches in a highly reproducible manner (e.g., via 3D holographic patterning and printing). In addition, networks of blood vessels are printed within the mesh patches. Inclusion of printed networks of blood vessels improves the long term survival of the skin graft.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for printing an organoid, comprising:
   (a) providing a media chamber comprising a medium comprising (i) a plurality of cells and (ii) one or more polymer precursors; and
   (b) using at least one energy beam to generate a patterned three-dimensional (3D) holographic projection in said medium in said media chamber along at least one energy beam path that is patterned into a three-dimensional (3D) projection in accordance with computer instructions for printing a 3D organoid in computer memory, to form at least a portion of said 3D organoid comprising (i) at least a subset of said plurality of cells, and (ii) a polymer formed from said one or more polymer precursors.

2. The method of claim 1, wherein said plurality of cells are selected from the group consisting of stromal endothelial cells, endothelial cells, follicular reticular cells or precursors thereof, naïve B cells or other immature B cells, memory B cells, plasma B cells, helper T cells and subsets of the same, effector T cells and subsets of the same, CD8+T cells, CD4+T cells, regulatory T cells, natural killer T cells, naive T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same, macrophages and subsets of the same, and leukocytes and subsets of the same.

3. The method of claim 1, wherein said 3D organoid is selected from the group consisting of a B cell germinal center, a thymic-like development niche, a lymph node, an islet of Langerhans, a hair follicle, a tumor, a tumor spheroid, a neural bundle or support cells, a nephron, a liver organoid, an intestinal crypt, a primary lymphoid organ and, a secondary lymphoid organ.

4. The method of claim 1, wherein a shape of said 3D organoid is selected from the group consisting of spherical, oval, ovate, ovoid, square, rectangular, cuboid, any polygonal shape, free-form, and tear-drop shape.

5. The method of claim 1, wherein said polymer of said at least said portion of said 3D organoid forms a network.

6. The method of claim 5, wherein said network is reticular, amorphous, or a net.

7. The method of claim 6, wherein said amorphous network is designed to facilitate cellular interactions or movement between or within cellular niches.

8. The method of claim 7, wherein said amorphous network comprises a framework of an aperture size or a density that facilitates movement of said at least said subset of said plurality of cells between or within said cellular niches.

9. A method for printing an organoid, comprising:
(a) providing a media chamber comprising a first medium, wherein said first medium comprises a first plurality of cells and a first polymeric precursor;
(b) using at least one energy beam to generate a patterned three-dimensional (3D) holographic projection in said first medium in said media chamber along at least one energy beam path in accordance with computer instructions for printing a three-dimensional (3D) organoid in computer memory, to subject at least a portion of said first medium in said media chamber to form a first portion of said 3D organoid;
(c) providing a second medium in said media chamber, wherein said second medium comprises a second plurality of cells and a second polymeric precursor, wherein said second plurality of cells is of a different type than said first plurality of cells; and
(d) using at least one energy beam to generate a patterned three-dimensional (3D) holographic projection in said second medium in said media chamber along at least one energy beam path in accordance with said computer instructions, to subject at least a portion of said second medium in said media chamber to form a second portion of said 3D organoid.

10. The method of claim 9, wherein said first plurality of cells and said second plurality of cells are from a subject.

11. The method of claim 9, wherein said first plurality of cells and said second plurality of cells are selected from the group consisting of stromal endothelial cells, endothelial cells, follicular reticular cells or precursors thereof, naïve B cells or other immature B cells, memory B cells, plasma B cells, helper T cells and subsets of the same, effector T cells and subsets of the same, CD8+T cells, CD4+T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same, macrophages and subsets of the same, and leukocytes and subsets of the same.

12. The method of claim 9, wherein said 3D organoid is selected from the group consisting of a B cell germinal center, a thymic-like development niche, and a lymph node.

13. The method of claim 12, wherein said 3D organoid is a functional subunit of an organ, a semi-functional aggregation of immune cells, or a semi-functional partial structure of said 3D organoid.

14. The method of claim 9, wherein said 3D organoid comprises a desired physiological function.

15. The method of claim 9, wherein said polymer of said at least said portion of said 3D organoid forms a network.

16. The method of claim 15, wherein said network is reticular, amorphous, or a net.

17. The method of claim 16, wherein said amorphous network is designed to facilitate cellular interactions or movement between or within cellular niches.

18. The method of claim 17, wherein said amorphous network comprises a framework of an aperture size or a density that facilitates movement of said first and second plurality of cells between or within said cellular niches.

19. The method of claim 9, wherein said 3D organoid is a 3D lymphoid organoid.

20. The method of claim 19, further comprising (e) subjecting said first and second portions of said 3D lymphoid organoid to conditions sufficient to stimulate production of one or more immunological proteins.

21. The method of claim 20, wherein in (e), said conditions comprise exposing said first and second portions of said 3D lymphoid organoid to an antigen in order to stimulate production of said one or more immunological proteins.

22. The method of claim 20, wherein said method further comprises:
(f) extracting one or more immunological proteins or fragments thereof from said first and second portions of said 3D lymphoid organoid.

23. The method of claim 20, wherein said one or more immunological proteins or fragments thereof are selected from the group consisting of antibodies, T-cell receptors, and cancer immunotherapeutics.

24. The method of claim 1, wherein said 3D organoid is a 3D lymphoid organoid.

25. The method of claim 24, further comprising (c) subjecting said at least said portion of said 3D lymphoid organoid to conditions sufficient to stimulate production of one or more immunological proteins.

26. The method of claim 25 wherein in (c), said conditions comprise exposing said at least said portion of said 3D lymphoid organoid to an antigen in order to stimulate production of said one or more immunological proteins.

27. The method of claim 25, wherein in (c), said conditions further comprise exposing said at least said portion of said 3D lymphoid organoid to an adjuvant.

28. The method of claim 25, wherein said method further comprises:
(d) extracting one or more immunological proteins or fragments thereof from said at least said portion of said 3D lymphoid organoid.

29. The method of claim 28, wherein said one or more immunological proteins or fragments thereof are selected from the group consisting of antibodies, T-cell receptors, and cancer immunotherapeutics.

* * * * *